(12) United States Patent
Zeitlin et al.

(10) Patent No.: US 8,828,376 B2
(45) Date of Patent: Sep. 9, 2014

(54) TREATMENT OF STROKE USING ISOLATED PLACENTAL CELLS

(75) Inventors: Andy Zeitlin, Basking Ridge, NJ (US); Ajai Pal, Bridgewater, NJ (US)

(73) Assignee: Anthrogenesis Corporation, Warren, NJ (US)

( * ) Notice: Subject to any disclaimer, the term of this patent is extended or adjusted under 35 U.S.C. 154(b) by 902 days.

(21) Appl. No.: 12/545,029

(22) Filed: Aug. 20, 2009

(65) Prior Publication Data

US 2010/0047351 A1 Feb. 25, 2010

Related U.S. Application Data

(60) Provisional application No. 61/090,565, filed on Aug. 20, 2008.

(51) Int. Cl.
*A01N 63/00* (2006.01)
*A61K 35/50* (2006.01)
*C12N 5/073* (2010.01)
*A61K 35/12* (2006.01)

(52) U.S. Cl.
CPC ............... *C12N 5/0605* (2013.01); *A61K 35/12* (2013.01); *A61K 35/50* (2013.01)
USPC ........... 424/93.1; 435/325; 435/366; 435/372

(58) Field of Classification Search
None
See application file for complete search history.

(56) References Cited

U.S. PATENT DOCUMENTS

| | | |
|---|---|---|
| 3,862,002 A | 1/1975 | Sanders |
| 4,829,000 A | 5/1989 | Kleinman et al. |
| 5,004,681 A | 4/1991 | Boyse et al. |
| 5,192,553 A | 3/1993 | Boyse et al. |
| 5,197,985 A | 3/1993 | Caplan et al. |
| 5,226,914 A | 7/1993 | Caplan et al. |
| 5,272,071 A | 12/1993 | Chappel |
| 5,284,766 A | 2/1994 | Okano et al. |
| 5,372,581 A | 12/1994 | Anderson |
| 5,415,665 A | 5/1995 | Hessel et al. |
| 5,437,994 A | 8/1995 | Emerson et al. |
| 5,443,950 A | 8/1995 | Naughton et al. |
| 5,460,964 A | 10/1995 | McGlave et al. |
| 5,464,764 A | 11/1995 | Capecchi et al. |
| 5,486,359 A | 1/1996 | Caplan et al. |
| 5,487,992 A | 1/1996 | Capecchi et al. |
| 5,516,532 A | 5/1996 | Atala et al. |
| 5,580,777 A | 12/1996 | Bernard |
| 5,591,625 A | 1/1997 | Gerson et al. |
| 5,605,822 A | 2/1997 | Emerson et al. |
| 5,627,059 A | 5/1997 | Capecchi et al. |
| 5,635,386 A | 6/1997 | Palsson et al. |
| 5,643,741 A | 7/1997 | Tsukamoto et al. |
| 5,646,043 A | 7/1997 | Emerson et al. |
| 5,654,186 A | 8/1997 | Cerami et al. |
| 5,654,381 A | 8/1997 | Hrkach et al. |
| 5,665,557 A | 9/1997 | Murray et al. |
| 5,668,104 A | 9/1997 | Nakahata et al. |
| 5,670,147 A | 9/1997 | Emerson et al. |
| 5,670,351 A | 9/1997 | Emerson et al. |
| 5,672,346 A | 9/1997 | Srour et al. |
| 5,709,854 A | 1/1998 | Griffith-Cima et al. |
| 5,716,616 A | 2/1998 | Prockop et al. |
| 5,716,794 A | 2/1998 | Tjota et al. |
| 5,716,827 A | 2/1998 | Tsukamoto |
| 5,733,541 A | 3/1998 | Taichman et al. |
| 5,733,542 A | 3/1998 | Haynesworth et al. |
| 5,736,396 A | 4/1998 | Bruder et al. |
| 5,744,361 A | 4/1998 | Hoffman et al. |
| 5,750,397 A | 5/1998 | Tsukamoto et al. |
| 5,763,197 A | 6/1998 | Tsukamoto et al. |
| 5,763,266 A | 6/1998 | Palsson et al. |
| 5,807,686 A | 9/1998 | Wagner et al. |
| 5,811,094 A | 9/1998 | Caplan et al. |
| 5,827,735 A | 10/1998 | Young et al. |
| 5,827,740 A | 10/1998 | Pittenger |
| 5,827,742 A | 10/1998 | Scadden |
| 5,837,539 A | 11/1998 | Caplan et al. |
| 5,849,553 A | 12/1998 | Anderson et al. |
| 5,855,619 A | 1/1999 | Caplan et al. |
| 5,858,782 A | 1/1999 | Long et al. |
| 5,866,414 A | 2/1999 | Badylak et al. |
| 5,874,301 A | 2/1999 | Keller et al. |
| 5,877,299 A | 3/1999 | Thomas et al. |
| 5,879,318 A | 3/1999 | Van Der Heiden et al. |
| 5,879,940 A | 3/1999 | Torok-Storb et al. |
| 5,902,741 A | 5/1999 | Purchio et al. |
| 5,905,041 A | 5/1999 | Beug et al. |
| 5,906,934 A | 5/1999 | Grande et al. |
| 5,908,782 A | 6/1999 | Marshak et al. |

(Continued)

FOREIGN PATENT DOCUMENTS

| | | |
|---|---|---|
| CN | 1407088 | 4/2003 |
| CN | 1548529 | 5/2003 |

(Continued)

OTHER PUBLICATIONS

Lapchak et al. Expert Opin Emerging Drugs 2007;12:389-406.*
Seyfried et al. J Neurosurg 2006;104:313-8.*
Battula et al. Differentiation 2007;75:279-91.*
Delorme et al. Blood 2008;111:2631-5, Online Dec. 17, 2007.*
U.S. Appl. No. 09/659,904, filed Sep. 12, 2000, Hariri.
U.S. Appl. No. 11/580,588, filed Oct. 13, 2006, Paludan et al.
U.S. Appl. No. 11/580,625, filed Oct. 13, 2006, Heidaran et al.
U.S. Appl. No. 11/648,802, filed Dec. 28, 2006, Heidaran et al.

(Continued)

*Primary Examiner* — Janice Li

(74) *Attorney, Agent, or Firm* — Jones Day

(57) ABSTRACT

Provided herein are methods for the treatment of stroke comprising administering to a stroke victim placental stem cells, populations of cells comprising placental stem cells, and/or compositions comprising placental stem cells.

45 Claims, 9 Drawing Sheets

(56) References Cited

U.S. PATENT DOCUMENTS

Figure 1:
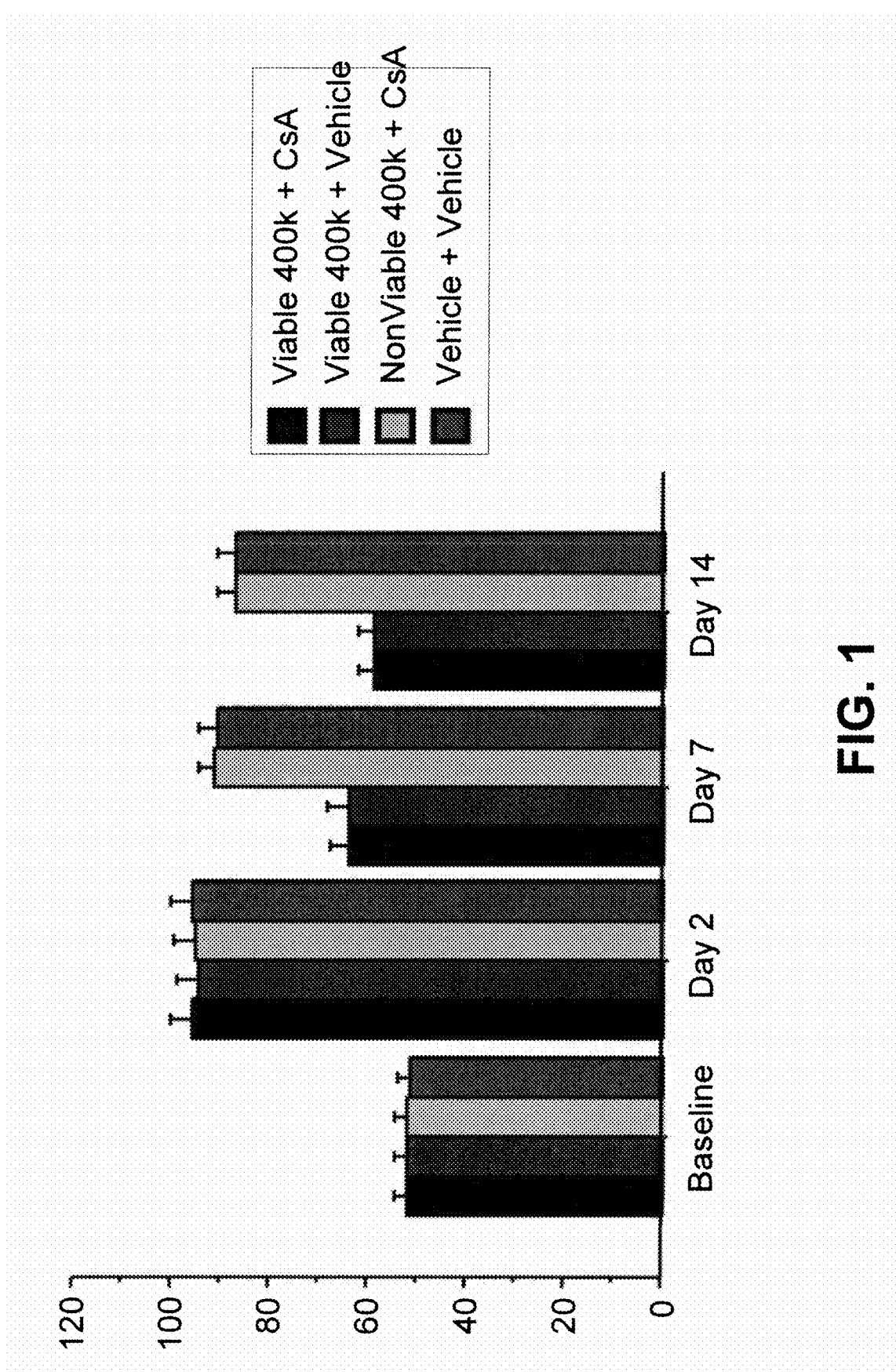

| Patent No. | Date | Inventor |
|---|---|---|
| 5,908,784 A | 6/1999 | Johnstone et al. |
| 5,914,108 A | 6/1999 | Tsukamoto et al. |
| 5,914,268 A | 6/1999 | Keller et al. |
| 5,916,202 A | 6/1999 | Haswell |
| 5,919,176 A | 7/1999 | Kuypers et al. |
| 5,919,702 A | 7/1999 | Purchio et al. |
| 5,922,597 A | 7/1999 | Verfaille et al. |
| 5,925,567 A | 7/1999 | Kraus et al. |
| 5,928,214 A | 7/1999 | Rubinstein et al. |
| 5,928,947 A | 7/1999 | Anderson et al. |
| 5,942,225 A | 8/1999 | Bruder et al. |
| 5,942,496 A | 8/1999 | Bonadio et al. |
| 5,958,767 A | 9/1999 | Snyder et al. |
| 5,962,325 A | 10/1999 | Naughton et al. |
| 5,968,820 A | 10/1999 | Zborowski et al. |
| 5,968,829 A | 10/1999 | Carpenter |
| 5,969,105 A | 10/1999 | Feng et al. |
| 5,993,429 A | 11/1999 | Kuypers et al. |
| 5,997,860 A | 12/1999 | Bauer et al. |
| 6,001,654 A | 12/1999 | Anderson et al. |
| 6,010,696 A | 1/2000 | Caplan et al. |
| 6,011,000 A | 1/2000 | Faller et al. |
| 6,020,469 A | 2/2000 | Hershenson |
| 6,022,540 A | 2/2000 | Bruder et al. |
| 6,022,848 A | 2/2000 | Kozlov et al. |
| 6,030,836 A | 2/2000 | Thiede |
| 6,057,123 A | 5/2000 | Craig et al. |
| 6,059,968 A | 5/2000 | Wolf, Jr. |
| 6,077,708 A | 6/2000 | Collins et al. |
| 6,087,113 A | 7/2000 | Caplan et al. |
| 6,093,531 A | 7/2000 | Bjornson et al. |
| 6,110,739 A | 8/2000 | Keller et al. |
| 6,127,135 A | 10/2000 | Hill et al. |
| 6,146,888 A | 11/2000 | Smith et al. |
| 6,174,333 B1 | 1/2001 | Kadiyala et al. |
| 6,179,819 B1 | 1/2001 | Haswel |
| 6,184,035 B1 | 2/2001 | Csete et al. |
| 6,190,368 B1 | 2/2001 | Kuypers et al. |
| 6,214,369 B1 | 4/2001 | Grande et al. |
| 6,224,860 B1 | 5/2001 | Brown |
| 6,225,119 B1 | 5/2001 | Qasba et al. |
| 6,227,202 B1 | 5/2001 | Mataparkar |
| 6,231,880 B1 | 5/2001 | Perrine |
| 6,239,157 B1 | 5/2001 | Mbalaviele et al. |
| 6,248,587 B1 | 6/2001 | Rodgers et al. |
| 6,251,383 B1 | 6/2001 | Upadhyay et al. |
| 6,255,112 B1 | 7/2001 | Thiede et al. |
| 6,280,718 B1 | 8/2001 | Kaufman et al. |
| 6,281,012 B1 | 8/2001 | McIntosh et al. |
| 6,291,240 B1 | 9/2001 | Mansbridge |
| 6,300,314 B1 | 10/2001 | Wallner et al. |
| 6,306,575 B1 | 10/2001 | Thomas et al. |
| 6,312,950 B1 | 11/2001 | Ohmura et al. |
| 6,322,784 B1 | 11/2001 | Pittenger et al. |
| 6,326,019 B1 | 12/2001 | Tseng |
| 6,326,198 B1 | 12/2001 | Emerson et al. |
| 6,328,765 B1 | 12/2001 | Hardwick et al. |
| 6,328,960 B1 | 12/2001 | McIntosh et al. |
| 6,333,029 B1 | 12/2001 | Vyakamam et al. |
| 6,335,195 B1 | 1/2002 | Rodgers et al. |
| 6,337,387 B1 | 1/2002 | Sakano et al. |
| 6,338,942 B2 | 1/2002 | Kraus et al. |
| 6,355,239 B1 | 3/2002 | Bruder et al. |
| 6,368,636 B1 | 4/2002 | McIntosh et al. |
| 6,387,367 B1 | 5/2002 | Davis-Sproul et al. |
| 6,387,369 B1 | 5/2002 | Pittenger et al. |
| 6,461,645 B1 | 10/2002 | Boyse et al. |
| 6,467,630 B1 | 10/2002 | Zborowski et al. |
| 6,497,875 B1 | 12/2002 | Sorrell et al. |
| 6,534,084 B1 | 3/2003 | Vyakamam et al. |
| 6,541,024 B1 | 4/2003 | Kadiyala et al. |
| 6,645,731 B2 | 11/2003 | Terstappen et al. |
| 6,685,936 B2 | 2/2004 | McIntosh et al. |
| 6,709,864 B1 | 3/2004 | Pittenger et al. |
| 6,797,269 B2 | 9/2004 | Mosca et al. |
| 6,835,377 B2 | 12/2004 | Goldberg et al. |
| 6,863,900 B2 | 3/2005 | Kadiyala et al. |
| 6,875,430 B2 | 4/2005 | McIntosh et al. |
| 6,916,655 B2 | 7/2005 | Yasumoto |
| 7,029,666 B2 | 4/2006 | Bruder et al. |
| 7,045,148 B2 | 5/2006 | Hariri |
| 7,147,626 B2 | 12/2006 | Goodman et al. |
| 7,153,500 B2 | 12/2006 | Qasba et al. |
| 7,255,879 B2 | 8/2007 | Hariri |
| 7,311,904 B2 | 12/2007 | Hariri |
| 7,311,905 B2 | 12/2007 | Hariri |
| 7,468,276 B2 | 12/2008 | Hariri |
| 7,498,171 B2 | 3/2009 | Hariri et al. |
| 7,976,836 B2 * | 7/2011 | Hariri .................. 424/93.1 |
| 2001/0005591 A1 | 6/2001 | Qasba et al. |
| 2001/0038836 A1 | 11/2001 | During et al. |
| 2002/0102239 A1 | 8/2002 | Koopmans |
| 2002/0132343 A1 | 9/2002 | Lum |
| 2003/0007954 A1 | 1/2003 | Naughton et al. |
| 2003/0032179 A1 | 2/2003 | Hariri |
| 2003/0044977 A1 | 3/2003 | Sakuragawa et al. |
| 2003/0045552 A1 | 3/2003 | Robarge et al. |
| 2003/0096841 A1 | 5/2003 | Robarge et al. |
| 2003/0161818 A1 | 8/2003 | Weiss et al. |
| 2003/0235563 A1 | 12/2003 | Strom et al. |
| 2004/0018617 A1 | 1/2004 | Hwang |
| 2004/0028660 A1 | 2/2004 | Hariri et al. |
| 2004/0048796 A1 | 3/2004 | Hariri et al. |
| 2004/0107453 A1 | 6/2004 | Furcht et al. |
| 2004/0136967 A1 | 7/2004 | Weiss et al. |
| 2004/0161419 A1 | 8/2004 | Strom et al. |
| 2004/0171147 A1 | 9/2004 | Hariri |
| 2004/0180040 A1 | 9/2004 | Phillips et al. |
| 2004/0219136 A1 | 11/2004 | Hariri |
| 2004/0229351 A1 | 11/2004 | Rodriguez |
| 2004/0241144 A1 | 12/2004 | Kaps et al. |
| 2005/0019865 A1 | 1/2005 | Kihm et al. |
| 2005/0019908 A1 | 1/2005 | Hariri |
| 2005/0032209 A1 | 2/2005 | Messina et al. |
| 2005/0037491 A1 | 2/2005 | Mistry et al. |
| 2005/0042595 A1 | 2/2005 | Haas |
| 2005/0054093 A1 | 3/2005 | Haas |
| 2005/0054098 A1 | 3/2005 | Mistry et al. |
| 2005/0058629 A1 | 3/2005 | Harmon et al. |
| 2005/0058630 A1 | 3/2005 | Harris et al. |
| 2005/0058631 A1 | 3/2005 | Kihm et al. |
| 2005/0085543 A1 | 4/2005 | Wallimann et al. |
| 2005/0089513 A1 | 4/2005 | Sakuragawa et al. |
| 2005/0112104 A1 | 5/2005 | Pittenger et al. |
| 2005/0118712 A1 | 6/2005 | Tsai et al. |
| 2005/0118715 A1 | 6/2005 | Hariri et al. |
| 2005/0124003 A1 | 6/2005 | Atala et al. |
| 2005/0143420 A1 | 6/2005 | Moutouh-de Parseval et al. |
| 2005/0148034 A1 | 7/2005 | Hariri et al. |
| 2005/0148074 A1 | 7/2005 | Davies et al. |
| 2005/0176139 A1 | 8/2005 | Chen et al. |
| 2005/0181502 A1 | 8/2005 | Furcht et al. |
| 2005/0186182 A1 | 8/2005 | Deisher et al. |
| 2005/0233452 A1 | 10/2005 | Ho et al. |
| 2005/0239897 A1 | 10/2005 | Pittenger et al. |
| 2005/0272148 A1 | 12/2005 | Hariri |
| 2005/0276792 A1 | 12/2005 | Kaminski et al. |
| 2005/0282272 A1 | 12/2005 | Bhatia et al. |
| 2005/0283844 A1 | 12/2005 | Furcht et al. |
| 2006/0008450 A1 | 1/2006 | Verfaillie et al. |
| 2006/0030041 A1 | 2/2006 | Furcht et al. |
| 2006/0078993 A1 | 4/2006 | Phan et al. |
| 2006/0153816 A1 | 7/2006 | Brown et al. |
| 2006/0153817 A1 | 7/2006 | Kihm et al. |
| 2006/0153818 A1 | 7/2006 | Dhanaraj et al. |
| 2006/0154366 A1 | 7/2006 | Brown et al. |
| 2006/0154367 A1 | 7/2006 | Kihm et al. |
| 2006/0166361 A1 | 7/2006 | Seyda et al. |
| 2006/0171930 A1 | 8/2006 | Seyda et al. |
| 2006/0188983 A1 | 8/2006 | Harris et al. |
| 2006/0222634 A1 | 10/2006 | Clarke et al. |
| 2006/0223177 A1 | 10/2006 | Harris et al. |
| 2006/0233765 A1 | 10/2006 | Messina et al. |
| 2006/0233766 A1 | 10/2006 | Messina et al. |

(56) References Cited

U.S. PATENT DOCUMENTS

| | | |
|---|---|---|
| 2006/0234376 A1 | 10/2006 | Mistry et al. |
| 2006/0263337 A1 | 11/2006 | Maziarz et al. |
| 2006/0281178 A1 | 12/2006 | Sakuragawa et al. |
| 2007/0009494 A1 | 1/2007 | Mistry et al. |
| 2007/0014771 A1 | 1/2007 | Mistry et al. |
| 2007/0020225 A1 | 1/2007 | Abramson et al. |
| 2007/0021704 A1 | 1/2007 | Hariri et al. |
| 2007/0021762 A1 | 1/2007 | Liu et al. |
| 2007/0031384 A1 | 2/2007 | Atala et al. |
| 2007/0036767 A1 | 2/2007 | Mistry et al. |
| 2007/0038298 A1 | 2/2007 | Sulner et al. |
| 2007/0043328 A1 | 2/2007 | Goodman et al. |
| 2007/0053888 A1 | 3/2007 | Hariri |
| 2007/0092497 A1 | 4/2007 | Hariri |
| 2007/0092967 A1 | 4/2007 | Han et al. |
| 2007/0134210 A1 | 6/2007 | Heidaran |
| 2007/0141700 A1 | 6/2007 | Harmon |
| 2007/0160588 A1 | 7/2007 | Kihm |
| 2007/0190034 A1 | 8/2007 | Paludan et al. |
| 2007/0190042 A1 | 8/2007 | Edinger et al. |
| 2007/0264269 A1 | 11/2007 | Harmon et al. |
| 2007/0275362 A1 | 11/2007 | Edinger et al. |
| 2007/0292399 A1 | 12/2007 | Heidaran et al. |
| 2007/0292910 A1 | 12/2007 | Heidaran et al. |
| 2008/0032401 A1 | 2/2008 | Edinger et al. |
| 2008/0044848 A1 | 2/2008 | Heidaran |
| 2008/0069895 A1 | 3/2008 | Liu et al. |
| 2008/0131410 A1 | 6/2008 | Hariri |
| 2008/0131522 A1 | 6/2008 | Liu et al. |
| 2008/0131966 A1 | 6/2008 | Hariri |
| 2008/0145934 A1 | 6/2008 | Harris et al. |
| 2008/0152624 A1 | 6/2008 | Paludan et al. |
| 2008/0152629 A1 | 6/2008 | Edinger et al. |
| 2008/0166328 A1 | 7/2008 | Harmon et al. |
| 2008/0175824 A1 | 7/2008 | Heidaran et al. |
| 2008/0181935 A1 | 7/2008 | Bhatia et al. |
| 2008/0181967 A1 | 7/2008 | Liu et al. |
| 2008/0206343 A1 | 8/2008 | Edinger et al. |
| 2008/0208158 A1 | 8/2008 | Goodman et al. |
| 2008/0213227 A1 | 9/2008 | Aggarwal et al. |
| 2008/0213228 A1 | 9/2008 | Edinger et al. |
| 2008/0226595 A1 | 9/2008 | Edinger et al. |
| 2009/0053805 A1 | 2/2009 | Hariri |
| 2009/0104164 A1 | 4/2009 | Zhang et al. |
| 2009/0142831 A1 | 6/2009 | Hariri |
| 2009/0226406 A1 | 9/2009 | Hariri |
| 2009/0252710 A1 | 10/2009 | Zhang et al. |
| 2011/0217271 A1* | 9/2011 | Hariri ........................ 424/93.7 |

FOREIGN PATENT DOCUMENTS

| | | |
|---|---|---|
| CN | 1786154 | 6/2006 |
| EP | 0333328 | 9/1989 |
| EP | 0529751 | 3/1993 |
| EP | 0552380 | 7/1993 |
| EP | 1264877 | 12/2002 |
| EP | 1405649 | 4/2004 |
| JP | 2003235549 | 12/2002 |
| JP | 2005151907 | 11/2003 |
| WO | WO 90/11354 | 10/1990 |
| WO | WO 91/01140 | 2/1991 |
| WO | WO 91/06667 | 5/1991 |
| WO | WO 93/04169 | 3/1993 |
| WO | WO 95/22611 | 8/1995 |
| WO | WO 96/34035 | 10/1996 |
| WO | WO 96/39101 | 12/1996 |
| WO | WO 98/37903 | 9/1998 |
| WO | WO 99/03973 | 1/1999 |
| WO | WO 99/64566 | 12/1999 |
| WO | WO 00/17325 | 3/2000 |
| WO | WO 00/27999 | 5/2000 |
| WO | WO 00/38762 | 7/2000 |
| WO | WO 00/73421 | 12/2000 |
| WO | WO 01/93909 | 12/2001 |
| WO | WO 03/102151 | 12/2003 |
| WO | WO 2004/087896 | 10/2004 |
| WO | WO 2005/042703 | 5/2005 |
| WO | WO 2005/105992 | 11/2005 |
| WO | WO 2006/015214 | 2/2006 |
| WO | WO 2006/111706 | 10/2006 |
| WO | WO 2007/047468 | 4/2007 |
| WO | WO 2007/073552 | 6/2007 |
| WO | WO 2007/087293 | 8/2007 |
| WO | WO 2008/060541 | 5/2008 |

OTHER PUBLICATIONS

U.S. Appl. No. 11/648,804, filed Dec. 28. 2006, Edinger et al.
U.S. Appl. No. 11/648,812, filed Dec. 28, 2006, Heidaran et al.
U.S. Appl. No. 11/648,813, filed Dec. 28, 2006, Edinger et al.
U.S. Appl. No. 11/648,824, filed Dec. 28, 2006, Heidaran et al.
U.S. Appl. No. 12/396,397, filed Mar. 2, 2009, Hariri et al.
U.S. Appl. No. 12/618,664, filed Nov. 13, 2009, Hariri.
U.S. Appl. No. 12/624,359, filed Nov. 23, 2009, Hariri.
U.S. Appl. No. 12/687,851, filed Jan. 10, 2010, Paludan et al.
Addison, et al., "Metabolism of Prednisolone by the Isolated Perfused Human Placental Lobule," J. Ster. Biochem. Mol. Biol., 39(1):83-90 (1991).
Aggarwal, et al., "Human Mesenchymal Stem Cells Modulate Allogeneic Immune Cell Responses," Blood 105(4):1815-22 (2005).
Anker In't P, et al., "Isolation of Mesenchymal Stem Cells of Fetal or Maternal Origin from Human Placenta," Stem Cells, 2004; 22:1338-45.
Ashihara, et al., "Successful Peripheral Blood Stem Cell Transplantation for Myelodysplastic Syndrome," Bone Marrow Transplantation 24(12): 1343-1345 (1999).
Bailo, et al., "Engraftment Potential of Human Amnion and Chorion Cells Derived from Term Placenta," Transplantation 78:1439-1448 (2004).
Ballin, et al., "Autologous Umbilical Cord Blood Transfusion," Arch. Dis. Child Fetal Neonatal. Ed. 73(3):F181-F183 (1995).
Barry et al., "The Monoclonal Antibody SH-2, Raised Against Human Mesenchymal Stem Cells, Recognizes an Epitope on Endoglin (CD105)," Osiris Therapeutics Inc., 2001 Aliceanna Street, Baltimore, MD 21231, Biochemical and Biophysical Research Communications 265:134-139 (1999).
Barry, "Where do all the placentas go?" Canadian Journal of Infection Control 9(1):8-10 (1994).
Belvedere, et al., "Increased Blood Volume and CD34(+)CD38(−) Progenitor Cell Recovery Using a Novel Umbilical Cord Blood Collection System," Stem Cells 18(4):245-251 (2000).
Campagnoli, et al., "Identification of Mesenchymal Stem/Progenitor Cells in Human First-Trimester Fetal Blood, Liver, and Bone Marrow." Blood 98(8):2396-402 (2001).
Carter, et al., "Characterization of MSC Potential to Treat GVHD Using Molecular Markers Linked to MSC-Mediated Immunosuppression in Vitro," Blood, 106(11) part 2, Abstract No. 4322,160B (2005).
Chao, et al., "Stem Cell Transplantation (Cord Blood Transplants)." American Society of Hematology p. 354-371 (2004).
Chen, et al. "Intravaneous Administration of Human Umbilical Cord Reduces Behavioral Deficits after Stroke in Rats," Stroke 32(11): 2682-2688 (2001).
Chen, et al., "The Potential for the Use of Mononuclear Cells from Human Umbilical Cord Blood in the Treatment of Amyotrophic Lateral Sclerosis is SOD1 Mice," J. Med. 31(1-2):21-30 (2000).
Chen, et al., "Therapeutic Benefit of Intravenous Administration of Bone Marrow Stromal Cells after Cerebral Ischemia in Rats," Stroke, 32(4):1005-11 (2001).
Chin, et al., "Enhanced Interferon Production and Lymphokine-Activated Cytotoxicity of Human Placental Cells," Cellular Immunology 113:1-9 (1988).
Clark, et al., "Placental Trophoblast from Successful Human Pregnancies Expresses the Tolerance Signaling Molecule, CD200 (OX-2)" Am. J. Reprod. Immunol., 50(3):187-195 (2003).
Cosma, et al., "Use and Application of Stem Cells in Toxicology," SOT 2003 Annual Meeting, p. 4, Abstract 19.

(56) References Cited

OTHER PUBLICATIONS

Czarneski, et al., "Effects of Cord Blood Transfer on the Hematopoietic Recovery Following Sublethal Irradiation in MRL lpr/lpr Mice," Proc. Soc. Exp. Biol. Med. 220(2):79-87 (1999).
Database WPI Week 200357 Derwent Publications Ltd., London, GB, AN 2003-59905 & CN 1 407 888 A (Zhou S) Apr. 2, 2003.
Davani, et al., "Mesenchymal Progenitor Cells Differentiate into an Endothelial Phenotype, Enhance Vascular Density, and Improve Heart Function in a Rat Cellular Cardiomyoplasty Model," Circulation 108[suppl II]:II-253-II-258 (2003).
Davies, et al. "Thalidomide and Immunomodulatory Derivatives Augment Natural Killer Cell Cytotoxicity in Multiple Myeloma," Blood 98(1):210-216 (2001).
Davies, et al., "Engraftment and Survival After Unrelated-Donor Bone Marrow Transplantation: A Report from the National Marrow Donor Program," Blood, 2000; 96(13): 4096-4102.
Davila, et al., "Use and Application of Stem Cells in Toxicology," Toxicological Sciences 79:214-223 (2004).
De Coppi,, et al., "Amniotic Fluid and Chorionic Villi Derived Human Stem Cells for the Engineering of Tissues in Vivo." The Journal of Urology, vol. 171, No. 4, Supplement, Saturday, May 8, 2004, p. 21, Abstract 81.
De Coppi, et al., "Human Embryonic and Fetal Stem-Cell Isolation from Amniotic Fluid and Placenta for Tissue Reconstruction." Urology and Reproductive Surgery, vol. 195, No. 3S, Sep. 2002, p. S93.
De Coppi, et al., "Human fetal stem cell isolation from amniotic fluid for tissue reconstruction," J. Urology 167(4 Supp.) 85 (Abstract 338) (2002).
De Coppi, et al., "Pluripotent Stem Cells Derived from Human Chorionic Villi and Amniotic Fluid for Tissue Engineering Applications." Experimental Biology/IUPS 2005: Meeting Abstracts, A1366, Abstract 781.7.
De Wynter, et al., "CD34+AC133+ Cells Isolated from Cord Blood are Highly Enriched in Long-Term Culture-Initiating Cells, NOD/SCID-Repopulating Cells and Dendritic Cell Progenitors," Stem Cells 16(6):387-396 (1998).
Drake, et al., "Human Placental Cytotrophoblasts Attract Monocytes and CD56 (Bright) Natural Killer Cells Via the Actions of Monocyte Inflammatory Protein 1Alpha," J. Exp. Med. 193(10):1199-1212 (2001).
Elchalal, et al., "Postpartum Umbilical Cord Blood Collection for Transplantation: a Comparison of Three Methods," Am. J. of Obstetrics & Gyn. 182(1 Pt 1):227-232 (2000).
Ende, "Berashis Cells in Human Umbilical Cord Blood Vs. Embryonic Stem Cells," J. Med. 33(1-4):167-171 (2002).
Ende, "Collection of Umbilical Cord Blood for Transplantation," Blood 80(6):1623-1624 (1992).
Ende, "The Feasibility of Using Blood Bank Stored (4° C.) Cord Blood, Unmatched for HLA for Marrow Transplantation," Am. J. Clin. Pathol. 111:773-781 (1999).
Ende, et al., "Human Umbilical Cord Blood Cells Amerliorate Alzheimer's Disease in Transgenic Mice, " J. Med. 32(3-4):241-7 (2001).
Ende, et al., "Human Umbilical Cord Blood Cells Ameliorate Huntington's Disease in Transgenic Mice," J. Med. 32(3-4):231-240 (2001).
Ende, et al., "Human Umbilical Cord Blood Effect on SOD Mice (Amyotrophic Lateral Sclerosis)," Life Sci. 67(1):53-59 (2001).
Ende, et al., "Parkinson's Disease Mice and Human Umbilical Cord Blood," Journal of Medicine 33(1-4):173-180 (2002).
Ende, et al., "Pooled Umbilical Cord Blood as a Possible Universal Donor for Marrow Reconstitution and Use in Nuclear Accidents," Life Sci. 69:1531-1539 (2001).
Ende, et al., "The Effect of Human Cord Blood on SJL/J Mice After Chemoablation and Irradiation and its Possible Clinical Significance," Immunol. Invest. 24(6):999-1012 (1995).
Erices, et al., "Mesenchymal Progenitor Cells in Human Umbilical Cord Blood," Br. J. Haemotol. 109(1):235-242 Abstract (2000).
Fasouliotis, et al., "Human umbilical cord blood banking and transplantation: a state of the art," Eur. J. Obstet. Gynecol. Reprod. Biol. 90(1):13-25 (2000).
Frank H G, et al., "Cell culture models of human trophoblast: primary culture of trophoblast—a workshop report." Placent APR 2001, vol. 22 Suppl A, Apr. 2001, pp. S107-S109, XP002443188 ISSN: 0143-4004.
Gluckman, et al., "Cord Blood Heamatopoietic Stem Cells: Biology and Transplantation," In: Hematology, American Society of Hematology Education Program Book (1998) p. 1-14.
Gluckman, et al., "Results of Unrelated Umbilical Cord Blood Hematipoeietic Stem Cell Transplant," Transfusion Cinique et Biologique 8(3):146-154 (2001).
Hadjantonakis, et al., "The Stem Cells of Early Embryos," Differentiation 68:159-166 (2001).
Hamada, et al., "Mesenchymal Stem Cells (MSC) as Therapeutic Cytoreagents for Gene Therapy," Cancer Sci 96:149-156 (2005).
Harbacheuski, et al., "Placenta Derived Adherent Cells (PDACs) Supress Tumor Cells of Diverse Origin." Blood 108(11):288 (2006).
Hatzopoulos, et al. "Isolation and characterization of endothelial progenitor cells from mouse embryos," Development. 125(8):1457-68 (1998).
Herrera, et al., "Mesenchymal Stem Cells Contribute to the Renal Repair of Acute Tubular Epithelial Injury,"• Int. J. Mol. Med., 2004: 14(6):1035-41.
Himori, et al., Chemotherapeutic susceptibility of human bone marrow progenitor cells and human myelogenous leukemia cells (HL-60) in co-culture: preliminary report. Int J Cell Cloning. 2(4):254-62 (1984).
Hirashima, et al. "Maturation of embryonic stem cells into endothelial cells in an in vitro model of vasculogenesis," Blood. 93(4):1253-63 (1999).
Hoek R M, et al., "Down-regulation of the macrophage lineage though interaction with OX2 (CD200)" Science, American Association for the ADvancement of Science, US, vol. 290, No. 5497, Dec. 1, 2000, pp. 1768-1771, XP002263649 ISSN:0036-8075.
Hows, "Status of Umbilical Cord Blood Transplantation in the Year 2001," J Clin Pathol 54(6):428-434 (2001).
Hoynowski, et al., "Characterization and Differentiation of Equine Umbilical Cord-Derived Matrix Cells,"• Biochemical and Biophysical Research Communications, 2007; 362:347-53.
Huss, "Isolation of Primary and Immortalized CD34-Hematopoietic and Mesenchymal Stem Cells from Various Sources," Stem Cells 18:1-9 (2000).
Huss, "Perspectives on the Morphology and Biology of CD34-Negative Stem Cells," J. Hematother. Stem. Cell Res. 9(6):783-793 (2000).
IGURA, et al., "Isolation and Characterization of Mesencymal Progenitor Cells from Chorionic Villi of Human Placenta," Cytotherapy 6(6): 543-553 (2004).
International Preliminary Report on Patentability from PCT/US2006/049491 dated Jan. 14, 2008.
Iwasaki, "Recent Advances in the Treatment of Graft-Versus-Host Disease,"• Clin. Med. Res., 2004; 2(4):243-52.
Jaiswal, et al., "Osteogenic Differentiation of Purified, Culture-Expanded Human Mesenchymal Stem Cells in vitro," J. Cell Biochem. 64(2):295-312 (1997).
Jones, et al., "Isolation and Characterization of Bone Marrow Multipotential Mesenchymal Progenitor Cells," Arthritis Rheum. 46(12):3349-3360 (2002).
Kawata, et al., "Transcriptional Control of HLA-A,B,C Antigen in Human Placental Cytotrophoblast Isolated Using Trophoblast- and HLA-Specific Monoclonal Antibodies and the Fluorescence-Activated Cell Sorter," J. Exp. Med. 160(3):633-51 (1984).
Koc, et al., "Rapid Hematopoietic Recovery After Coinfusion of Autologous-Blood Stem Cells and Culture-Expanded Marrow Mesenchymal Stem Cells in Advanced Breast Cancer Patients Receiving High-Dose Chemotherapy," J Clin Oncol 18:307-316 (2000).
Koh, et al., "Parthenolgenetically Derived Stem Cells for Urologic Reconstruction." The Journal of Urology, vol. 171, No. 4, Supplement, Saturday, May 8, 2004, p. 21, Abstract 81.

(56) References Cited

OTHER PUBLICATIONS

Korbling, et al., "Hepatocytes and Epithelial Cells of Donor Origin in Recipients of Peripheral-Blood Stem Cells," N. Engl. J. Med. 346(10):738-746 (2002).
Kurtzberg, "Placental Bood as a Surce of Hmatopoietic Sem Cells for Transplantation into Unrelated Recipients," N. Engl. J. Med. 335:157-166 (1996).
Law, E., et al., Stem Cell Symposium, State of New Jersey Commission on Science & Technology 2005 (Abstract).
Lazarus, et al., "Cotransplantation of HLA-Identical Sibling Culture-Expanded Mesenchymal Stem Cells and Hematopoietic Stem Cells in Hematologic Malignancy Patients," Biol Blood Marrow Transplant, 11(5):389-398 (2005).
Le Blanc, et al., "Treatment of Severe Acute Graft-Versus-Host Disease With Third Party Haploidentical Mesenchvmal Stem Cells,"• Lancet, 2004; 363(9419):1439-41.
Lebkowski, et al., "Serum and Plasma Levels of FGF-2 and VEGF in Healthy Blood Donors," Cancer J. 7(Suppl 2):S83-S93 (2001).
Leonard, et al., "The Role of ABC Transporters in Clinical Practice," Oncologist. 8:411-424 (2003).
Li, et al., "Mesenchymal Stem Cells Derived from Human Placenta Suppress Allogenic Umbilical Cord Blood Lymphocyte Proliferation." Cell Res. 15: 539-547 (2005).
Lin, et al. "Murine CD200(+)CK7(+) trophoblasts in a poly (I:C)-induced embryo resorption model." Reproduction (Cambridge), vol. 130, No. 4, Oct. 2005, pp. 529-537, XP002443406 ISSN: 1470-1626.
Lorkowski, et al., "ABCG Subfamily of Human ATP-Binding Cassette Proteins," Pure Appl. Chem. 74(11):2057-2081 (2002).
Lowy, et al. "Isolation of transforming DNA: cloning the hamster aprt gene," Cell. 22(3):817-23 (1980).
Ma, et al., "Development of an in vitro Human Placenta Model by the Cultivation of Human Trophoblasts in a Fiber-Based Bioreactor System," Tissue Engineering 5, 91-102 (1999).
Ma, et al., "Human Umbilical Cord Wharton's Jelly-Derived Mesenchymal Stem Cells Differentiation into Nerve-Like Cells," Chinese Med. Jour., 118(23):1987-93 (2005).
Mackay, et al., "Chondrogenic Differentiation of Cultured Human Mesenchymal Stem Cells from Marrow," Tissue Engineering, 1998; 4(4):415-28.
McMaster et al, "Human Placental HLA-G Expression is Restricted to Differentiated Cytotrophoblasts," J. Immunol. 154(8):3771-3778 (1995).
Melnik, et al., "Evaluation of Eluants from Batch Separations of CD34(+) Cells from Human Cord Blood Using a Commercial, Immunomagnetic Cell Separation System," Biotechnol. Prog. 17(5):907-916 (2001).
Miki, et al., "Isolation of Multipotent Stem Cells from Placenta." AASLD Abstracts, Hepatology, Oct. 2003, Abstract 279, p. 290A.
Miki, et al., "Production of Hepatocytes from Human Amniotic Stem Cells." Hepatology, Abstract 20, vol. 36, No. 4, Pt. 2, 2002.
Miki, et al., "Stem Cell Characteristics of Amniotic Epithelial Cells." Stem Cells Express, published online Aug. 9, 2005; doi:10. 1634/stemcells.2004-0357.
Moreau et al., "Myofibroblastic Stromal Cells Isolated From Human Bone Marrow Indue the Proliferation of Both Early Myeloid and B-Lymphoid Cells," Blood 82:2396-2405 (1993).
Morigi, et al., "Mesenchymal Stem Cells are Renotropic, Helping to Repair the Kidney and Improve Function in Acute Renal Failure," J. Am. Soc. Nephrol., 2004; 15(7):1794-1804.
Morishima, et al., "The Clinical Significance of Human Leukocyte Antigen (HLA) Allele Compatibility in Patients Receiving a Marrow Transplant from Serologically HLA-A, HLA-B, and HLA-DR Matched Unrelated Donors," Blood, 2002; 99(11):4200-06.
Ninichuk, et al., "Multipotent Mesenchymal Stem Cells Reduce Interstitial Fibrosis but do not Delay Progression of Chronic Kidney Disease in Collagen4a3-Deficient Mice," Kidney Int., 2006; 70(1):121-29.
Nishishita, et al., "A Potential Pro-Angiogenic Cell Therapy with Human Placenta-Derived Mesenchymal Cells," Biochem. Biophys. Res. Commun. 325(1):24-31 (2004).

Noort, et al., "Mesenchymal Stem Cells Promote Engraftment of Human Umbilical Cord Blood-Derived CD34+ Cells in NOD/SCID Mice," Experimental Hematology 30(8):870-878 (2002).
Paludan, et al., "Immune Suppression by Placenta Derived Adherent Cells (PDAC) Correlate with Monocyte Chemoattractant Protein-1 and 1 L-2 Secretion," Blood 108 (2006) (abstract only).
Panepucci, et al., "Comparison of Gene Expression of Umbilical Cord Vein and Bone Marrow-Derived Mesenchvmal Stem Cells," Stem Cells, 2004; 22(7):1263-78.
Papaioannou, et al., "Stem Cells from Early Mammalian Embryos" Stem Cells Handbook:19-31 (2004).
Pera, et al., "Human Embryonic Stem Cells," J. Cell. Sci. 113:5-10 (2000).
Pountos, et al., "Mesenchymal Stem Cell Tissue Engineering: Techniques for Isolation, Expansion and Application," Injury Int. J. Care Injured, 2007; 38(Supp. 4):S23-33.
Reyes, et al. Origin of endothelial progenitors in human postnatal bone marrow.J Clin Invest. 109(3):337-46 (2002).
Reyes, et at., "Purification and ex vivo Expansion of Postnatal Human Marrow Mesodermanl Progenitor Cells," Blood 98(9):2615-2625 (2001).
Rossant, "Stem Cells from the Mammalian Blastocyst," Stem Cell 19:477-482 (2001).
Roth, et al., "Human Placental Cytotrophoblats Produce the Immunosuppressive Cytokine Interliukin 10," J. Exp. Med. 184(2):539-548 (1996).
Rubinstein, et al., "Processing and Cryopreservation of Placental/Umbilical Cord Blood for Unrelated Bone Marrow Reconstitution," Proc. Natl. Acad. Sci. USA 92:10119-10122 (1995).
Russo, "Fighting Darwin's Battles. Symposium Marks Evolutionist Victory, Anti-Evolution Growth" The Scientist 15:6 (2001).
Sakuragawa, et al., "Expression of markers for both neuronal and glial cells in human amniotic epithelial cells," Neuroscience Letters 209:9-12 (1996).
Sakuragawa, et al., "Human amniotic epithelial cells are promising transgene carriers for allogeneic cell transplantation into liver," J. Hum. Genet. 45:171-176 (2000).
Schutz, et al., "Isolation and Cultivation of Endothelial Cells Derived from Human Placenta," Eur. J. Cell Biol. 395-401 (1996).
Shamblott, et al., "Derivation of Pluripotent Stem Cells from Cultured Human Primordial Germ Cells," Proc. Natl. Acad. Sci. USA 95(23):13726-13731 (1998).
Shuto, et al., "Dexamethasone Stimulates Osteoclast-Like Cell Formation by Inhibiting Granulocyte-Macrophage Colony-Stimulating Factor Production in Mouse Bone Marrow Cultures," Endocrinology 134:1121-1126 (1994).
Sirchia, et al., "Placental/Umbilical Cord Blood Transplantation," Haematologica 84:738-747 (1999).
Slager, Transforming growth factor-beta in the early mouse embryo: implications for the regulation of muscle formation and implantation. Dev Genet. 14(3):212-24 (1993).
Stanworth, et al., "Stem Cells: Progress in Research and Edging towards the Clinical Setting," Clin. Med. 1(5):378-382 (2001).
Thomson, et al., Embryonic stem cell lines derived from human blastocysts. Science. 282 (5391): 1145-7(1998).
Toma, et al., "Human Mesenchymal Stem Cells Differentiate to a Cardiomyocyte Phenotype in the Adult Murine Heart," Circulation, 2002; 105:93-98.
Turner, et al., "A modified Harvest Technique for Cord Blood Hematopoietic Stem Cells," Bone Marrow Transplantation 10:89-91 (1992).
Ulloa-Montoya, et al., "Culture Systems for Pluripotent Stem Cells," Journal of Bioscience and Bioengineering, 2005; 100(1):12-27.
Viacord, Umblicical cord blood can save lives (Informational brochure), Boston: ViaCell Centr-Bro R1 10/01 (2001).
Wang, et al., "Mesenchymal Stem/Progenitor Cells in Human Cord Blood as Support for Ex Vivo Expansion of CD34+ Hematopoietic Stem Cells and for Chondrogenic Differentiation," Haematologica 89(7):837-844 (2004).
Watanabe, et al, "Multilineage Potential of Human Placenta-Derived Mesenchymal Cells," Blood 100(11):517a, Abstract 2022 (2002).

(56) References Cited

OTHER PUBLICATIONS

Woods, et al., "Osomometric and permeability characteristics of human placental/umbilical cord blood CD34+ cells and their application to cryopreservation," J. Hematother. Stem Cell Res. 9(2):161-173 (2000).
Yen, B. Linju et al, "Isolation of multipotent cells from human term placenta" Stem Cells (Dayton, Ohio) 2005, vol. 23, No. 1, Jan. 2005, pp. 3-9, XP002443187 ISSN: 1065-5099.
Young, et al., "Human Pluripotent and Progenitor Cells Display Cell Surface Cluster Differentiation Markers CD10, CD13, CD56, and MHC class-I," Proc Soc Exp Biol Med. 221(1):63-71 (1999).
Zhang, et al., "Comparison of Mesenchymal Stem Cells from Human Placenta and Bone Marrow," Chinese Medical Journal, 117(6):882-87 (2004).
Zhang, et al., "Efficient Adena-Associated Virus-Mediated Gene Expression in Human Placenta-Derived Mesenchvmal Cells," Microbiol. Immunol., 2003; 47(1):109-16.
Zhang, et al., "Human Placenta-Derived Mesenchymal Progenitor Cells Support Culture Expansion of Long-Term Culture-Initiating Cells from Cord Blood CD34+ Cells." Exp. Hematol. 32: 657-664 (2004).
Notice of Allowance dated Sep. 15, 2005 in U.S. Appl. No. 10/004,942, now US Patent No. 7,045,148.
Office Action dated Dec. 16, 2004 in U.S. Appl. No. 10/004,942, now US Patent No. 7,045,148.
Office Action dated Dec. 5, 2003 in U.S. Appl. No. 10/004,942, now US Patent No. 7,045,148.
Office Action dated Jun. 15, 2004 in U.S. Appl. No. 10/004,942, now US Patent No. 7,045,148.
Office Action dated Jun. 20, 2005 in U.S. Appl. No. 10/004,942, now US Patent No. 7,045,148.
Office Action dated May 7, 2003 in U.S. Appl. No. 10/004,942, now US Patent No. 7,045,148.
Notice of Allowance dated Aug. 16, 2007 in U.S. Appl. No. 10/074,976, now US Patent No. 7,311,904.
Office Action dated Jan. 5, 2006 in U.S. Appl. No. 10/074,976, now US Patent No. 7,311,904.
Office Action dated Mar. 27, 2007 in U.S. Appl. No. 10/074,976, now US Patent No. 7,311,904.
Office Action dated Sep. 20, 2006 in U.S. Appl. No. 10/074,976, now US Patent No. 7,311,904.
Office Action dated Sep. 23, 2004 in U.S. Appl. No. 10/074,976, now US Patent No. 7,311,904.
Notice of Allowance dated Sep. 10, 2007 in U.S. Appl. No. 10/366,671, now US Patent No. 7,311,905.
Office Action dated Jan. 19, 2006 in U.S. Appl. No. 10/366,671, now US Patent No. 7,311,905.
Office Action dated May 14, 2007 in U.S. Appl. No. 10/366,671, now US Patent No. 7,311,905.
Office Action dated Oct. 10, 2006 in U.S. Appl. No. 10/366,671, now US Patent No. 7,311,905.
Notice of Allowance dated Oct. 30, 2008 in U.S. Appl. No. 10/411,655, now US Patent No. 7,498,171.
Office Action dated Feb. 28, 2008 in U.S. Appl. No. 10/411,655, now US Patent No. 7,498,171.
Office Action dated Jul. 11, 2007 in U.S. Appl. No. 10/411,655, now US Patent No. 7,498,171.
Office Action dated May 18, 2006 in U.S. Appl. No. 10/411,655, now US Patent No. 7,498,171.
Office Action dated Nov. 20, 2006 in U.S. Appl. No. 10/411,655, now US Patent No. 7,498,171.
Office Action dated Apr. 26, 2007 in U.S. Appl. No. 10/449,248.
Office Action dated Aug. 29, 2006 in U.S. Appl. No. 10/449,248.
Notice of Allowance May 21, 2007 in U.S. Appl. No. 10/640,428, now US Patent No. 7,255,879.
Office Action dated Jan. 19, 2006 in U.S. Appl. No. 10/640,428, now US Patent No. 7,255,879.
Office Action dated Oct. 18, 2006 in U.S. Appl. No. 10/640,428, now US Patent No. 7,255,879.
Office Action dated Dec. 28, 2006 in U.S. Appl. No. 10/721,144.
Office Action dated Feb. 5, 2008 in U.S. Appl. No. 10/721,144.
Office Action dated Jan. 11, 2006 in U.S. Appl. No. 10/721,144.
Office Action dated Jun. 14, 2006 in U.S. Appl. No. 10/721,144.
Office Action dated Jun. 27, 2007 in U.S. Appl. No. 10/721,144.
Office Action dated Oct. 4, 2005 in U.S. Appl. No. 10/721,144.
Office Action dated Apr. 6, 2007 in U.S. Appl. No. 10/874,828, now US Patent No. 7,468,276.
Office Action dated Dec. 13, 2007 in U.S. Appl. No. 10/874,828, now US Patent No. 7,468,276.
Office Action dated Jun. 12, 2006 in U.S. Appl. No. 10/874,828, now US Patent No. 7,468,276.
Office Action dated Apr. 20, 2007 in U.S. Appl. No. 11/187,400.
Office Action dated Feb. 20, 2009 in U.S. Appl. No. 11/187,400.
Office Action dated Jan. 4, 2008 in U.S. Appl. No. 11/187,400.
Non-Final Office Action dated Oct. 21, 2009 in U.S. Appl. No. 11/648,804.
Office Action dated Jan. 26, 2009 in U.S. Appl. No. 11/648,813.
Final Office Action dated Oct. 27, 2009 in U.S. Appl. No. 11/648,813.
Steemers et al., "Whole-genome genotyping with the single-base extension assay," 2006, Nat. Methods 3(1):31-33.

\* cited by examiner

TREATMENT OF STROKE USING ISOLATED PLACENTAL CELLS

The present application claims benefit of U.S. Provisional Patent application No. 61/090,565, filed Aug. 20, 2008, which is incorporated herein by reference in its entirety.

1. FIELD

Provided herein are methods of using isolated placental cells, e.g., placental multipotent cells, populations of such isolated placental cells, and/or compositions comprising the cells in the treatment of an individual having hypoxic injury or a disruption in the flow of blood in or around the brain, e.g., a symptom of or a defect, e.g., a neurological deficit attributable to a disruption in the flow of blood in or around the brain.

2. BACKGROUND

A stroke, also known as a "brain attack," cerebrovascular accident (CVA) or acute ischemic cerebrovascular syndrome, is a loss of brain function(s), usually rapidly developing, that is due to a disturbance in the blood vessels supplying blood to the brain or brainstem. The disturbance can be ischemia (lack of blood) caused by, e.g., thrombosis or embolism, or can be due to a hemorrhage. According to the World Health Organization, stroke is a "neurological deficit of cerebrovascular cause that persists beyond 24 hours or is interrupted by death within 24 hours." Persistence of symptoms beyond 24 hours separates stroke from Transient Ischemic Attack (TIA), in which symptoms persist for less than 24 hours.

Currently, treatment of ischemic stroke typically includes antiplatelet medication such as aspirin, clopidogrel, dipyridamole, or anticoagulant medication, such as warfarin, to reduce or relieve blockage causing the ischemia. In addition, blood sugar levels are brought to as normal as possible, and the stroke patient is provided adequate oxygen and intravenous fluids. Treatment of hemorrhagic stroke generally comprises one or more of administration of a blood pressure-lowering drug, administration of a pain medication other than a non-steroidal anti-inflammatory drug (NSAID), administration of a calcium channel blocker (e.g., Nimodipine), and surgery, if indicated, to repair the vessel ruptures responsible for hemorrhage.

However, such treatments only attempt to mitigate ongoing neurological damage, and do nothing to restore lost function. Numerous non-cellular neuroprotective agents have been tested for efficacy in treatment of stroke, and have failed, including N-methyl-D-aspartate receptor antagonists, nalmefene, lubeluzole, clomethiazole, calcium channel blockers (including a-amino-3-hydroxy-5-methylisoxazole-4-proprionic acid antagonists, serotonin agonists (e.g., repinotan), and transmembrane potassium channel modulators), tirilazad, anti-ICAM-1 antibody, human antileukocytic antibody (Hu23F2G), antiplatelet antibody (e.g., abciximab), citicoline (an exogenous form of cytidine-5'-diphosphocholine), and basic fibroblast growth factor.

There are no effective treatments for stroke. Thus, a need exists for therapies that not only mitigate neurological damage arising from either condition, but improve neural function and prognosis.

3. SUMMARY

Provided herein, in one aspect, are methods for the use of isolated placental cells, populations of isolated placental cells, populations of cells comprising isolated placental stem cells and compositions comprising the isolated placental cells in the treatment of an individual having a disruption of the flow of blood in or around the individual's central nervous system (CNS), e.g. brain or spinal cord. The methods comprise, e.g., treatment of a symptom or neurological deficit in an individual attributable to a disruption of the flow of blood in or around the individual's brain, such as hypoxic injury, anoxic injury, stroke (e.g., ischemic or hemorrhagic stroke), non-stroke hemorrhage or TIA. As contemplated herein, treatment of a symptom or neurological deficit in an individual attributable to a disruption of the flow of blood in or around the individual's brain includes treatment of symptoms or neurological deficits attributable to reperfusion injury that may accompany such a disruption of flow of blood in or around the individual's brain. Successful treatment of ischemic stroke, e.g., anoxic injury or hypoxic injury, has been demonstrated herein in an accepted animal stroke model. See Example 1 and Example 2.

In one aspect, provided herein is a method of treating an individual who has a disruption of the flow of blood in or around the individual's brain, e.g., who has a symptom or neurological deficit attributable to a disruption of the flow of blood in or around the individual's brain or central nervous system (CNS), comprising administering to said individual a therapeutically effective amount of isolated tissue culture plastic-adherent human placental cells, wherein said isolated placental cells have characteristics of multipotent cells or stem cells. In certain embodiments, the disruption of flow of blood results in anoxic injury or hypoxic injury to the individual's brain or CNS.

In certain embodiments, the isolated placental cells are isolated placental stem cells. In certain other embodiments, the isolated placental cells are isolated placental multipotent cells. In a specific embodiment, the isolated placental cells are $CD34^-$, $CD10^+$ and $CD105^+$ as detected by flow cytometry. In a more specific embodiment, the isolated $CD34^-$, $CD10^+$, $CD105^+$ placental cells are placental stem cells. In another more specific embodiment, the isolated $CD34^-$, $CD10^+$, $CD105^+$ placental cells are multipotent placental cells. In another specific embodiment, the isolated $CD34^-$, $CD10^+$, $CD105^+$ placental cells have the potential to differentiate into cells of an osteogenic phenotype, or cells of a chondrogenic phenotype. In another embodiment, the isolated $CD34^-$, $CD10^+$, $CD105^+$ placental cells have the potential to differentiate into cells of a neural phenotype. In a more specific embodiment, the isolated $CD34^-$, $CD10^+$, $CD105^+$ placental cells are additionally $CD200^+$. In another more specific embodiment, the isolated $CD34^-$, $CD10^+$, $CD105^+$ placental cells are additionally $CD90^+$ or $CD45^-$, as detected by flow cytometry. In another more specific embodiment, the isolated $CD34^-$, $CD10^+$, $CD105^+$ placental cells are additionally $CD90^+$ or $CD45^-$, as detected by flow cytometry. In a more specific embodiment, the $CD34^-$, $CD10^+$, $CD105^+$, $CD200^+$ placental cells are additionally $CD90^+$ or $CD45^-$, as detected by flow cytometry. In another more specific embodiment, the $CD34^-$, $CD10^+$, $CD105^+$, $CD200^+$ cells are additionally $CD90^+$ and $CD45^-$, as detected by flow cytometry. In another more specific embodiment, the $CD34^-$, $CD10^+$, $CD105^+$, $CD200^+$, $CD90^+$, $CD45^-$ cells are additionally $CD80^-$ and $CD86^-$, as detected by flow cytometry.

In a more specific embodiment, the $CD34^-$, $CD10^+$, $CD105^+$ cells are additionally one or more of $CD29^+$, $CD38^-$, $CD44^+$, $CD54^+$, $CD80^-$, $CD86^-$, $SH3^+$ or $SH4^+$. In another more specific embodiment, the cells are additionally $CD44^+$. In another specific embodiment, the $CD34^-$, $CD10^+$, $CD105^+$ placental cells are additionally one or more of $CD13^+$, $CD29^+$, $CD33^+$, $CD38^-$, $CD44^+$, $CD45^-$, $CD54^+$, $CD62E^-$, CD62L⁻, CD62P⁻, SH3⁺ (CD73⁺), SH4⁺ (CD73⁺), CD80⁻, CD86⁻, CD90⁺, SH2⁺ (CD105⁺), CD106/VCAM⁺, CD117⁻, CD144/VE-cadherin$^{low}$, CD184/CXCR4⁻, CD200⁺, CD133⁻, OCT-4⁺, SSEA3⁻, SSEA4⁻, ABC-p⁺, KDR⁻ (VEGFR2⁻), HLA-A,B,C⁺, HLA-DP,DQ,DR⁻, HLA-G⁺, or Programmed Death-1 Ligand (PDL1)⁺, or any combination thereof. In a more specific embodiment, the CD34⁻, CD10⁺, CD105⁺ placental cells are additionally CD13⁺, CD29⁺, CD33⁺, CD38⁻, CD44⁺, CD45⁻, CD54/ICAM⁺, CD62E⁻, CD62L⁻, CD62P⁻, SH3⁺ (CD73⁺), SH4+(CD73⁺), CD80⁻, CD86⁻, CD90⁺, SH2⁺ (CD105⁺), CD106/VCAM⁺, CD117⁻, CD144/VE-cadherin$^{low}$, CD184/CXCR4⁻, CD200⁺, CD133⁻, OCT-4⁺, SSEA3⁻, SSEA4⁻, ABC-p⁺, KDR⁻ (VEGFR2⁻), HLA-A,B,C⁺, HLA-DP,DQ,DR⁻, HLA-G⁺, and Programmed Death-1 Ligand (PDL1)⁺.

In other embodiments, the isolated placental cells are CD200⁺ and HLA-G⁺; CD73⁺, CD105⁺, and CD200⁺; CD200⁺ and OCT-4⁺; CD73⁺, CD105⁺ and HLA-G⁺; CD73⁺ and CD105⁺ and facilitate the formation of one or more embryoid-like bodies in a population of placental cells comprising said isolated placental cells when said population is cultured under conditions that allow the formation of an embryoid-like body; or OCT-4⁺ and facilitate the formation of one or more embryoid-like bodies in a population of placental cells comprising the isolated placental cells when said population is cultured under conditions that allow formation of embryoid-like bodies; or any combination thereof. In other embodiments, the isolated placental cells are CD34⁻, CD10⁺, CD105⁺, and additionally are CD200⁺ and HLA-G⁺; CD73⁺, CD105⁺, and CD200⁺; CD200⁺ and OCT-4⁺; CD73⁺, CD105⁺ and HLA-G⁺; CD73⁺ and CD105⁺ and facilitate the formation of one or more embryoid-like bodies in a population of placental cells comprising said isolated placental cells when said population is cultured under conditions that allow the formation of an embryoid-like body; or OCT-4⁺ and facilitate the formation of one or more embryoid-like bodies in a population of placental cells comprising the isolated placental cells when said population is cultured under conditions that allow formation of embryoid-like bodies; or any combination thereof.

In a specific embodiment, said CD200⁺, HLA-G⁺ placental cells are CD34⁻, CD38⁻, CD45⁻, CD73⁺ and CD105⁺. In another specific embodiment, said isolated CD73⁺, CD105⁺, and CD200⁺ placental cells are CD34⁻, CD38⁻, CD45⁻, and HLA-G⁺. In another specific embodiment, said CD200⁺, OCT-4⁺ stem cells are CD34⁻, CD38⁻, CD45⁻, CD73⁺, CD105⁺ and HLA-G⁺. In another specific embodiment, said isolated CD73⁺, CD105⁺ and HLA-G⁺ placental cells are CD34⁻, CD45⁻, OCT-4⁺ and CD200⁺. In another specific embodiment, said isolated CD73⁺ and CD105⁺ placental cells are OCT-4⁺, CD34⁻, CD38⁻ and CD45⁻. In another specific embodiment, said cells are CD73⁺, CD105⁺, CD200⁺, CD34⁻, CD38⁻, and CD45⁻.

In certain embodiments, the isolated placental cells are one or more of CD10⁺, CD29⁺, CD34⁻, CD38⁻, CD44⁺, CD45⁻, CD54⁺, CD90⁺, SH2⁺, SH3⁺, SH4⁺, SSEA3⁻, SSEA4⁻, OCT-4⁺, MHC-I⁺ or ABC-p⁺, where ABC-p is a placenta-specific ABC transporter protein (also known as breast cancer resistance protein (BCRP) and as mitoxantrone resistance protein (MXR)). In a specific embodiment, the isolated placental cells are CD10⁺, CD29⁺, CD34⁻, CD38⁻, CD44⁺, CD45⁻, CD54⁺, CD90⁺, SH2⁺, SH3⁺, SH4⁺, SSEA3⁻, SSEA4⁻, and OCT-4⁺. In another embodiment, the isolated placental cells are CD10⁺, CD29⁺, CD34⁻, CD38⁻, CD45⁻, CD54⁺, SH2⁺, SH3⁺, and SH4⁺. In another embodiment, the isolated placental cells are CD10⁺, CD29⁺, CD34, CD38⁻, CD45⁻, CD54⁺, SH2⁺, SH3⁺, SH4⁺ and OCT-4⁺. In another embodiment, the isolated placental cells are CD10⁺, CD29⁺, CD34⁻, CD38⁻, CD44⁺, CD45⁻, CD54⁺, CD90⁺, HLA-1⁺, SH2⁺, SH3⁺, SH4⁺. In another embodiment, the isolated placental cells are OCT-4⁺ and ABC-p⁺. In another embodiment, the isolated placental cells are SH2⁺, SH3⁺, SH4⁺ and OCT-4⁺. In another embodiment, the isolated placental cells are OCT-4⁺, CD34⁻, SSEA3⁻, and SSEA4⁻. In a specific embodiment, said OCT-4⁺, CD34⁻, SSEA3⁻, and SSEA4⁻ cells are additionally CD10⁺, CD29⁺, CD34⁻, CD44⁺, CD45⁻, CD54⁻, CD90⁺, SH2⁺, SH3⁺, and SH4⁺. In another embodiment, the isolated placental cells are OCT-4⁺ and CD34⁻, and either SH3⁺ or SH4⁺. In another embodiment, the isolated placental cells are CD34⁻ and either CD10⁺, CD29⁺, CD44⁺, CD54⁺, CD90⁺, or OCT-4⁺. In certain embodiments, the isolated placental cells are CD10⁺, CD34⁻, CD105⁺ and CD200⁺.

In another embodiment, the isolated placental cells useful in the methods of treatment described herein are one or more of CD10⁺, CD29⁻, CD44⁺, CD45⁻, CD54/ICAM⁻, CD62-E⁻, CD62-L⁻, CD62-P⁻, CD80⁻, CD86⁻, CD103⁻, CD104⁻, CD105⁺, CD06/VCAM⁺, CD144VE-cadherin$^{low}$, CD184/CXCR4⁻, β2-microglobulin$^{low}$, HLA-I$^{low}$, HLA-II⁻, HLA-G$^{low}$, and/or PDL1$^{low}$. In a specific embodiment, the isolated placental cells are at least CD29⁻ and CD54⁻. In another specific embodiment, the isolated placental cells are at least CD44⁺ and CD106⁺. In another specific embodiment, the isolated placental cells are at least CD29⁺.

In another specific embodiment, said isolated placental cells express one or more genes at a detectably higher level than an equivalent number of bone marrow-derived mesenchymal stem cells, wherein said one or more genes are one or more of ACTG2, ADARB1, AMIGO2, ARTS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, ICAM1, IER3, IGFBP7, IL1A, IL6, IL18, KRT18, KRT8, LIPG, LRAP, MATN2, MEST, NFE2L3, NUAK1, PCDH7, PDLIM3, PKP2, RTN1, SERPINB9, ST3GAL6, ST6GALNAC5, SLC12A8, TCF21, TGFB2, VTN, and ZC3H12A, and wherein said bone marrow-derived mesenchymal stem cells have undergone a number of passages in culture equivalent to the number of passages said isolated placental cells have undergone. In a more specific embodiment, said isolated placental cells express said one or more genes when cultured for about 3 to about 35 population doublings in a medium comprising 60% DMEM-LG (e.g., from Gibco) and 40% MCDB-201 (e.g., from Sigma); 2% fetal calf serum (e.g., from Hyclone Labs.); 1× insulin-transferrin-selenium (ITS); 1× linoleic acid-bovine serum albumin (LA-BSA); 10⁻⁹ M dexamethasone (e.g., from Sigma); 10⁻⁴ M ascorbic acid 2-phosphate (e.g., from Sigma); epidermal growth factor 10 ng/mL (e.g., from R&D Systems); and platelet-derived growth factor (PDGF-BB) 10 ng/mL (e.g., from R&D Systems). In a more specific embodiment, said isolated placental cells express said one or more genes when cultured for from about 3 to about 35 population doublings in a medium comprising 60% DMEM-LG (e.g., from Gibco) and 40% MCDB-201 (e.g., from Sigma); 2% fetal calf serum (e.g., from Hyclone Labs.); 1× insulin-transferrin-selenium (ITS); 1× linoleic acid-bovine serum albumin (LA-BSA); 10⁻⁹ M dexamethasone (e.g., from Sigma); 10⁻⁴ M ascorbic acid 2-phosphate (Sigma); epidermal growth factor 10 ng/mL (e.g., from R&D Systems); and platelet-derived growth factor (PDGF-BB) 10 ng/mL (e.g., from R&D Systems).

In another specific embodiment of the method of treatment, said placental stem cells express the neurotrophic growth factors glial cell derived neurotrophic factor (GDNF), brain-derived neurotrophic factor (BDNF), hepatocyte growth factor (HGF), placental growth factor (PGF) and vascular endothelial growth factor (VEGF).

In another specific embodiment, said isolated placental cells are contained within a population of cells, at least 50% of the cells of which are said isolated placental cells. In another specific embodiment, said isolated placental cells are contained within a population of cells, at least 70% of the cells of which are said isolated placental cells. In another specific embodiment, said isolated placental cells are contained within a population of cells, at least 80% of the cells of which are said isolated placental cells. In another specific embodiment, said isolated placental cells are contained within a population of cells, at least 90% of the cells of which are said isolated placental cells. In certain other embodiments, the placental cells in said population of cells are substantially free of cells having a maternal genotype; e.g., at least 40%, 45%, 50%, 55%, 60%, 65%, 70%, 75%, 80%, 85%, 90%, 95%, 98% or 99% of the placental cells in said population have a fetal genotype, i.e., are fetal in origin. In certain other embodiments, the population of cells comprising said placental cells are substantially free of cells having a maternal genotype; e.g., at least 40%, 45%, 50%, 55%, 60%, 65%, 70%, 75%, 80%, 85%, 90%, 95%, 98% or 99% of the cells in said population have a fetal genotype, i.e., are fetal in origin.

In certain embodiments, any of the placental cells, e.g., placental stem cells or placental multipotent cells described herein, are autologous to a recipient, e.g., an individual who has had a stroke, or has a symptom of a stroke. In certain other embodiments, any of the placental cells, e.g., placental stem cells or placental multipotent cells described herein, are heterologous to a recipient, e.g., an individual who has had a stroke, or has a symptom of a stroke.

In another specific embodiment of the method of treatment, said isolated placental cells are cryopreserved prior to said administering. In another specific embodiment, said isolated placental cells are obtained from a placental stem cell bank.

In any of the above embodiments of isolated placental cells, the isolated placental cells generally do not differentiate during culturing in growth medium, i.e., medium formulated to promote proliferation, e.g., during proliferation in growth medium. In another specific embodiment, said isolated placental cells do not require a feeder layer in order to proliferate. In another specific embodiment, said isolated placental cells do not differentiate in culture as the result of culture in the absence of a feeder cell layer.

In another more specific embodiment, said isolated placental cells are obtained by perfusion of a postpartum placenta that has been drained of blood and perfused to remove residual blood; drained of blood but not perfused to remove residual blood; or neither drained of blood nor perfused to remove residual blood. In another more specific embodiment, said isolated placental cells are obtained by physical and/or enzymatic disruption of placental tissue.

Cell surface, molecular and genetic markers of placental cells, useful in the methods provided herein, are described in detail in Section 5.4.2, below.

In another specific embodiment, said disruption of flow of blood is a stroke. In a more specific embodiment, said stroke is an ischemic stroke. In another more specific embodiment, said stroke is a hemorrhagic stroke, e.g., an intracranial cerebral hemorrhage or spontaneous subarachnoid hemorrhage. In another specific embodiment, said disruption is a hematoma. In more specific embodiments, the hematoma is a dural hematoma, a subdural hematoma or a subarachnoid hematoma. In another specific embodiment, said hematoma is caused by external force on the skull, e.g., a head injury. In another specific embodiment, said disruption is a Transient Ischemic Attack (TIA), e.g., recurrent TIA. In another specific embodiment, said disruption is a vasospasm, e.g., a vasospasm following a hemorrhagic stroke.

In another specific embodiment of the method, said therapeutically effective amount is a number of isolated placental cells that results in elimination of, a detectable improvement in, lessening of the severity of, or slowing of the progression of one or more symptoms of, or neurological deficits attributable to, a disruption of the flow of blood in or around the brain or CNS exhibited by said individual, e.g., anoxic injury or hypoxic injury. In another specific embodiment, said therapeutically effective amount of isolated placental cells is administered to said individual prophylactically, e.g., to reduce or eliminate neurological damage caused by a second or subsequent disruption of flow of blood in or around the brain or CNS following said disruption of flow of blood.

In another specific embodiment, said symptom of disruption of blood flow in or around the brain, e.g., stroke, anoxic injury or hypoxic injury, is one or more of hemiplegia (paralysis of one side of the body); hemiparesis (weakness on one side of the body); muscle weakness of the face; numbness; reduction in sensation; altered sense of smell, sense of taste, hearing, or vision; loss of smell, taste, hearing, or vision; drooping of an eyelid (ptosis); detectable weakness of an ocular muscle; decreased gag reflex; decreased ability to swallow; decreased pupil reactivity to light; decreased sensation of the face; decreased balance; nystagmus; altered breathing rate; altered heart rate; weakness in sternocleidomastoid muscle with decreased ability or inability to turn the head to one side; weakness in the tongue; aphasia (inability to speak or understand language); apraxia (altered voluntary movements); a visual field defect; a memory deficit; hemineglect or hemispatial neglect (deficit in attention to the space on the side of the visual field opposite the lesion); disorganized thinking; confusion; development of hypersexual gestures; anosognosia (persistent denial of the existence of a deficit); difficulty walking; altered movement coordination; vertigo; disequilibrium; loss of consciousness; headache; and/or vomiting.

In another specific embodiment of the methods of treatment described above, said isolated placental cells are administered by bolus injection. In another specific embodiment, said isolated placental cells are administered by intravenous infusion. In a specific embodiment, said intravenous infusion is intravenous infusion over about 1 to about 8 hours. In another specific embodiment, said isolated placental cells are administered intracranially. In another specific embodiment, said isolated placental cells are administered intraperitoneally. In another specific embodiment, said isolated placental cells are administered intra-arterially. In a more specific embodiment, said isolated placental cells are administered within an area of ischemia. In another more specific embodiment, said isolated placental cells are administered to an area peripheral to an ischemia. In another specific embodiment of the method of treatment, said isolated placental cells are administered intramuscularly, intradermally, subcutaneously, or intraocularly.

In another embodiment of the methods of treatment described above, said isolated placental cells are administered by surgical implantation into said individual of a composition of matter comprising said isolated placental cells. In a more specific embodiment, said composition of matter is a matrix or scaffold. In another more specific embodiment, said matrix or scaffold is a hydrogel. In another more specific embodiment, said matrix or scaffold is a decellularized tissue. In another more specific embodiment, said matrix or scaffold is a synthetic biodegradable composition. In another more specific embodiment, said matrix or scaffold is a foam.

In another specific embodiment of the methods of treatment described above, said isolated placental cells are administered once to said individual. In another specific embodiment, said isolated placental cells are administered to said individual in two or more separate administrations. In another specific embodiment, said administering comprises administering between about $1\times10^4$ and $1\times10^5$ isolated placental cells, e.g., placental stem cells per kilogram of said individual. In another specific embodiment, said administering comprises administering between about $1\times10^5$ and $1\times10^6$ isolated placental cells per kilogram of said individual. In another specific embodiment, said administering comprises administering between about $1\times10^6$ and $1\times10^7$ isolated placental cells per kilogram of said individual. In another specific embodiment, said administering comprises administering between about $1\times10^7$ and $1\times10^8$ isolated placental cells per kilogram of said individual. In other specific embodiments, said administering comprises administering between about $1\times10^6$ and about $2\times10^6$ isolated placental cells per kilogram of said individual; between about $2\times10^6$ and about $3\times10^6$ isolated placental cells per kilogram of said individual; between about $3\times10^6$ and about $4\times10^6$ isolated placental cells per kilogram of said individual; between about $4\times10^6$ and about $5\times10^6$ isolated placental cells per kilogram of said individual; between about $5\times10^6$ and about $6\times10^6$ isolated placental cells per kilogram of said individual; between about $6\times10^6$ and about $7\times10^6$ isolated placental cells per kilogram of said individual; between about $7\times10^6$ and about $8\times10^6$ isolated placental cells per kilogram of said individual; between about $8\times10^6$ and about $9\times10^6$ isolated placental cells per kilogram of said individual; or between about $9\times10^6$ and about $1\times10^7$ isolated placental cells per kilogram of said individual. In another specific embodiment, said administering comprises administering between about $1\times10^7$ and about $2\times10^7$ isolated placental cells per kilogram of said individual to said individual. In another specific embodiment, said administering comprises administering between about $1.3\times10^7$ and about $1.5\times10^7$ isolated placental cells per kilogram of said individual to said individual. In another specific embodiment, said administering comprises administering up to about $3\times10^7$ isolated placental cells per kilogram of said individual to said individual. In a specific embodiment, said administering comprises administering between about $5\times10^6$ and about $2\times10^7$ isolated placental cells to said individual. In another specific embodiment, said administering comprises administering about $150\times10^6$ isolated placental cells in about 20 milliliters of solution to said individual.

In a specific embodiment, said administering comprises administering between about $5\times10^6$ and about $2\times10^7$ isolated placental cells to said individual, wherein said cells are contained in a solution comprising 10% dextran, e.g., dextran-40, 5% human serum albumin, and optionally an immunosuppressant.

In another specific embodiment, said administering comprises administering between about $5\times10^7$ and $3\times10^9$ isolated placental cells intravenously. In more specific embodiments, said administering comprises administering about $9\times10^8$ isolated placental cells or about $1.8\times10^9$ isolated placental cells intravenously. In another specific embodiment, said administering comprises administering between about $5\times10^7$ and $1\times10^8$ isolated placental cells intracranially. In a more specific embodiment, said administering comprises administering about $9\times10^7$ isolated placental cells intracranially.

In another specific embodiment, the methods of treatment described above comprise administering a second therapeutic agent to said individual. In a more specific embodiment, said second therapeutic agent is a neuroprotective agent. In a more specific embodiment, said second therapeutic agent is NXY-059 (a disulfonyl derivative of phenylbutylnitrone: disodium 4-((tert-butylimino)-methyl)benzene-1,3-disulfonate N-oxide, or disodium 4-((oxido-tert-butyl-azaniumylidene)methyl)benzene-1,3-disulfonate; also known as disufenton). In another more specific embodiment, the second therapeutic agent is a thrombolytic agent. In a more specific embodiment, said thrombolytic agent is tissue plasminogen activator (tPA). In embodiments in which the disruption of flow of blood in or around the brain is a hemorrhage, the second therapeutic agent can be an antihypertensive drug, e.g., a beta blocker or diuretic drug, a combination of a diuretic drug and a potassium-sparing diuretic drug, a combination of a beta blocker and a diuretic drug, a combination of an angiotensin-converting enzyme (ACE) inhibitor and a diuretic, an angiotensin-II antagonist and a diuretic drug, and/or a calcium channel blocker and an ACE inhibitor. In another more specific embodiment, the second therapeutic agent is a calcium channel blocker, glutamate antagonist, gamma aminobutyric acid (GABA) agonist, an antioxidant or free radical scavenger, In another specific embodiment of the method of treatment, said isolated placental cells are administered to said individual within 21-30, e.g., 21 days of development of one or more symptoms of a disruption of the flow of blood in or around the brain of said individual, e.g., within 21-30, e.g., 21 days of development of symptoms of stroke, anoxic injury or hypoxic injury. In another specific embodiment of the method of treatment, said isolated placental cells are administered to said individual within 14 days of development of one or more symptoms of a disruption of the flow of blood in or around the brain of said individual. In another specific embodiment of the method of treatment, said isolated placental cells are administered to said individual within 7 days of development of one or more symptoms of a disruption of the flow of blood in or around the brain of said individual. In another specific embodiment of the method of treatment, said isolated placental cells are administered to said individual within 48 hours of development of one or more symptoms of a disruption of the flow of blood in or around the brain of said individual. In another specific embodiment, said isolated placental cells are administered to said individual within 24 hours of development of one or more symptoms of a disruption of the flow of blood in or around the brain of said individual. In another specific embodiment, said isolated placental cells are administered to said individual within 12 hours of development of one or more symptoms of a disruption of the flow of blood in or around the brain of said individual. In another specific embodiment, said isolated placental cells are administered to said individual within 3 hours of development of one or more symptoms of a disruption of the flow of blood in or around the brain of said individual.

3.1 Definitions

As used herein, the term "about," when referring to a stated numeric value, indicates a value within plus or minus 20% of the stated numeric value.

As used herein, the term "anoxic injury" refers to an injury, e.g., a neurological injury or symptom, caused by a total lack of oxygen to an area of the brain or CNS.

As used herein, the term "hypoxic injury" refers to an injury, e.g., a neurological injury or symptom, caused by a partial lack of oxygen to an area of the brain or CNS.

As used herein, the term "SH2" refers to an antibody that binds an epitope on the cellular marker CD105. Thus, cells that are referred to as SH2$^+$ are CD105$^+$.

As used herein, the terms "SH3" and "SH4" refer to antibodies that bind epitopes present on the cellular marker CD73. Thus, cells that are referred to as SH3$^+$ and/or SH4+ are CD73$^+$.

A placenta has the genotype of the fetus that develops within it, but is also in close physical contact with maternal tissues during gestation. As such, as used herein, the term "fetal genotype" means the genotype of the fetus, e.g., the genotype of the fetus associated with the placenta from which particular isolated placental cells, as described herein, are obtained, as opposed to the genotype of the mother that carried the fetus. As used herein, the term "maternal genotype" means the genotype of the mother that carried the fetus, e.g., the fetus associated with the placenta from which particular isolated placental cells, as described herein, are obtained.

As used herein, the term "isolated cell," e.g., "isolated stem cell," means a cell that is substantially separated from other, different cells of the tissue, e.g., placenta, from which the stem cell is derived. A cell is "isolated" if at least 50%, 60%, 70%, 80%, 90%, 95%, or at least 99% of the cells, e.g., non-stem cells, with which the stem cell is naturally associated, or stem cells displaying a different marker profile, are removed from the stem cell, e.g., during collection and/or culture of the stem cell.

As used herein, "multipotent," when referring to a cell, means that the cell has the ability to differentiate into some, but not necessarily all, types of cells of the body, or into cells having characteristics of some, but not all, types of cells of the body. In certain embodiments, for example, an isolated placental cell that has the capacity to differentiate into a cell having characteristics of neurogenic, chondrogenic and/or osteogenic cells is a multipotent cell.

As used herein, the term "population of isolated cells" means a population of cells that is substantially separated from other cells of a tissue, e.g., placenta, from which the population of cells is derived.

As used herein, the term "placental stem cell" refers to a stem cell or progenitor cell that is derived from a mammalian placenta, regardless of morphology, cell surface markers, or the number of passages after a primary culture. The term "placental stem cell" as used herein does not, however, refer to, and a placental stem cell is not, however, a trophoblast, angioblast, a hemangioblast, an embryonic germ cell, an embryonic stem cell, a cell obtained from an inner cell mass of a blastocyst, or a cell obtained from a gonadal ridge of a late embryo, e.g., an embryonic germ cell. A cell is considered a "stem cell" if the cell displays attributes of a stem cell, e.g., a marker or gene expression profile associated with one or more types of stem cells; the ability to replicate at least 10-40 times in culture, and the ability to differentiate into cells displaying characteristics of differentiated cells of one or more of the three germ layers. The terms "placental stem cell" and "placenta-derived stem cell" may be used interchangeably. Unless otherwise noted herein, the term "placental" includes the umbilical cord. The isolated placental cells disclosed herein, in certain embodiments, differentiate in vitro under differentiating conditions, differentiate in vivo, or both.

As used herein, a placental cell is "positive" for a particular marker when that marker is detectable above background. For example, a placental cell is positive for, e.g., CD73 because CD73 is detectable on placental cells in an amount detectably greater than background (in comparison to, e.g., an isotype control). A cell is also positive for a marker when that marker can be used to distinguish the cell from at least one other cell type, or can be used to select or isolate the cell when present or expressed by the cell. In the context of, e.g., antibody-mediated detection, "positive," as an indication a particular cell surface marker is present, means that the marker is detectable using an antibody, e.g., a fluorescently-labeled antibody, specific for that marker; "positive" also refers to a cell exhibiting the marker in an amount that produces a signal, e.g., in a cytometer, that is detectably above background. For example, a cell is "CD200$^+$" where the cell is detectably labeled with an antibody specific to CD200, and the signal from the antibody is detectably higher than that of a control (e.g., background or an isotype control). Conversely, "negative" in the same context means that the cell surface marker is not detectable using an antibody specific for that marker compared a control (e.g., background or an isotype control). For example, a cell is "CD34$^-$" where the cell is not reproducibly detectably labeled with an antibody specific to CD34 to a greater degree than a control (e.g., background or an isotype control). Markers not detected, or not detectable, using antibodies are determined to be positive or negative in a similar manner, using an appropriate control. For example, a cell or population of cells can be determined to be OCT-4$^+$ if the amount of OCT-4 RNA detected in RNA from the cell or population of cells is detectably greater than background as determined, e.g., by a method of detecting RNA such as RT-PCR, slot blots, etc. Unless otherwise noted herein, cluster of differentiation ("CD") markers are detected using antibodies. In certain embodiments, OCT-4 is determined to be present, and a cell is "OCT-4$^+$" if OCT-4 is detectable using RT-PCR.

As used herein, "treat" encompasses the cure of, remediation of, improvement of, lessening of the severity of, or reduction in the time course of, a disease, disorder or condition, or any parameter or symptom thereof.

4. BRIEF DESCRIPTION OF THE FIGURES

FIG. 1: Results of Elevated Body Swing Test. Vertical axis: percent biased swing activity. Horizontal axis: day that swing activity is assessed. The Baseline is the percent biased swing activity prior to induced ischemia. Percent biased swing activity was also assessed at Day 2 post-infarct before isolated placental cells were administered intracranially, and again at days 7 and 14 post-infarct. Viable 400K: 4×10$^5$ viable isolated placental cells. Nonviable: nonviable placental stem cells. CsA: cyclosporine A.

Figure 2:
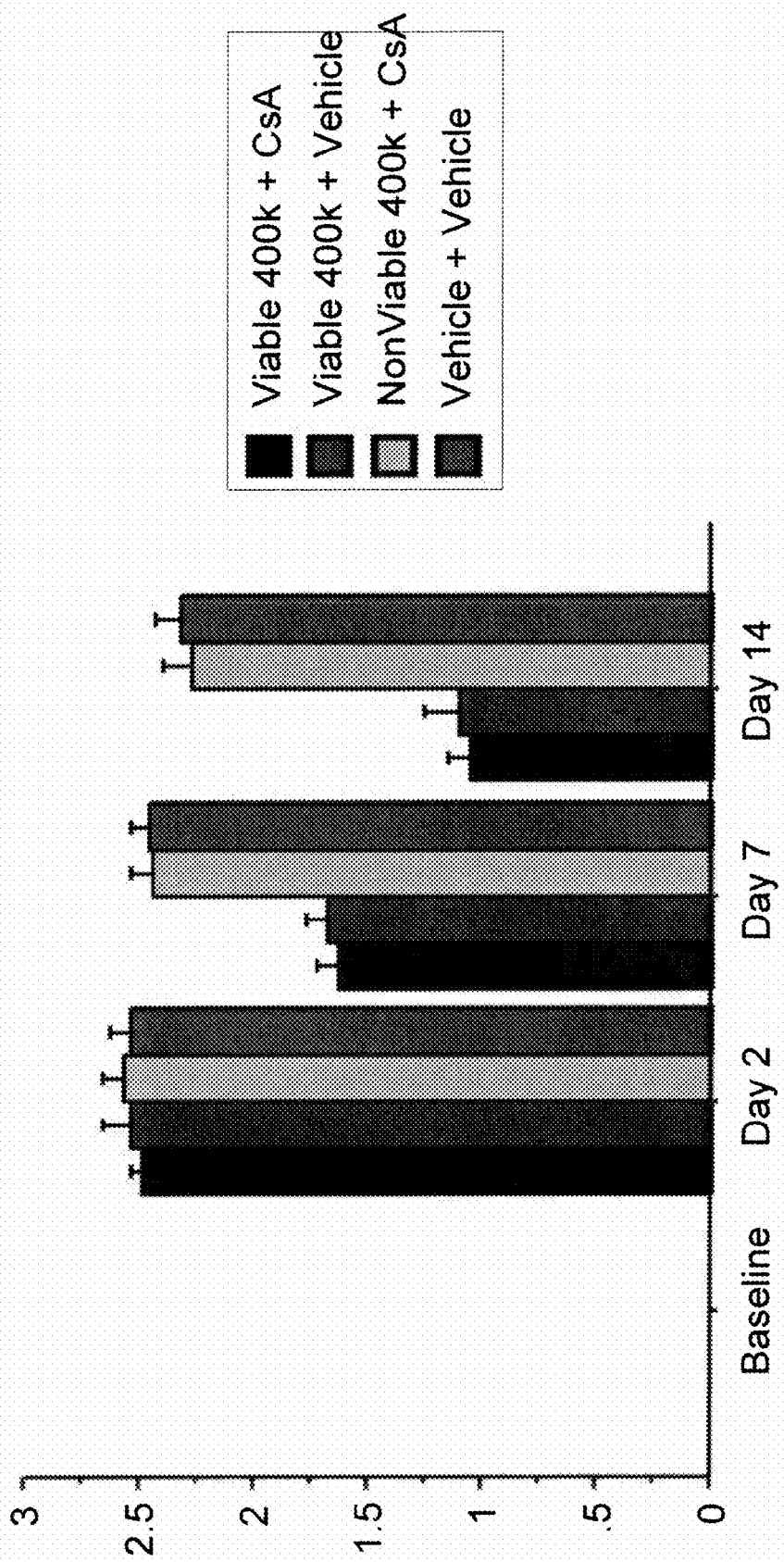

FIG. 2: Results of Bederson Test. Vertical axis: Mean Neurologic Deficit Score. Horizontal axis: day that neurologic deficit is assessed. Baseline is the neurologic deficit prior to induced ischemia; 0 indicates no deficit. Mean neurologic activity was also assessed at Day 2 post-infarct at the time isolated placental cells were administered, and again at days 7 and 14 post-infarct. Viable 400K: 4×10$^5$ viable isolated placental cells. Nonviable: nonviable placental stem cells. CsA: cyclosporine A.

Figure 3:
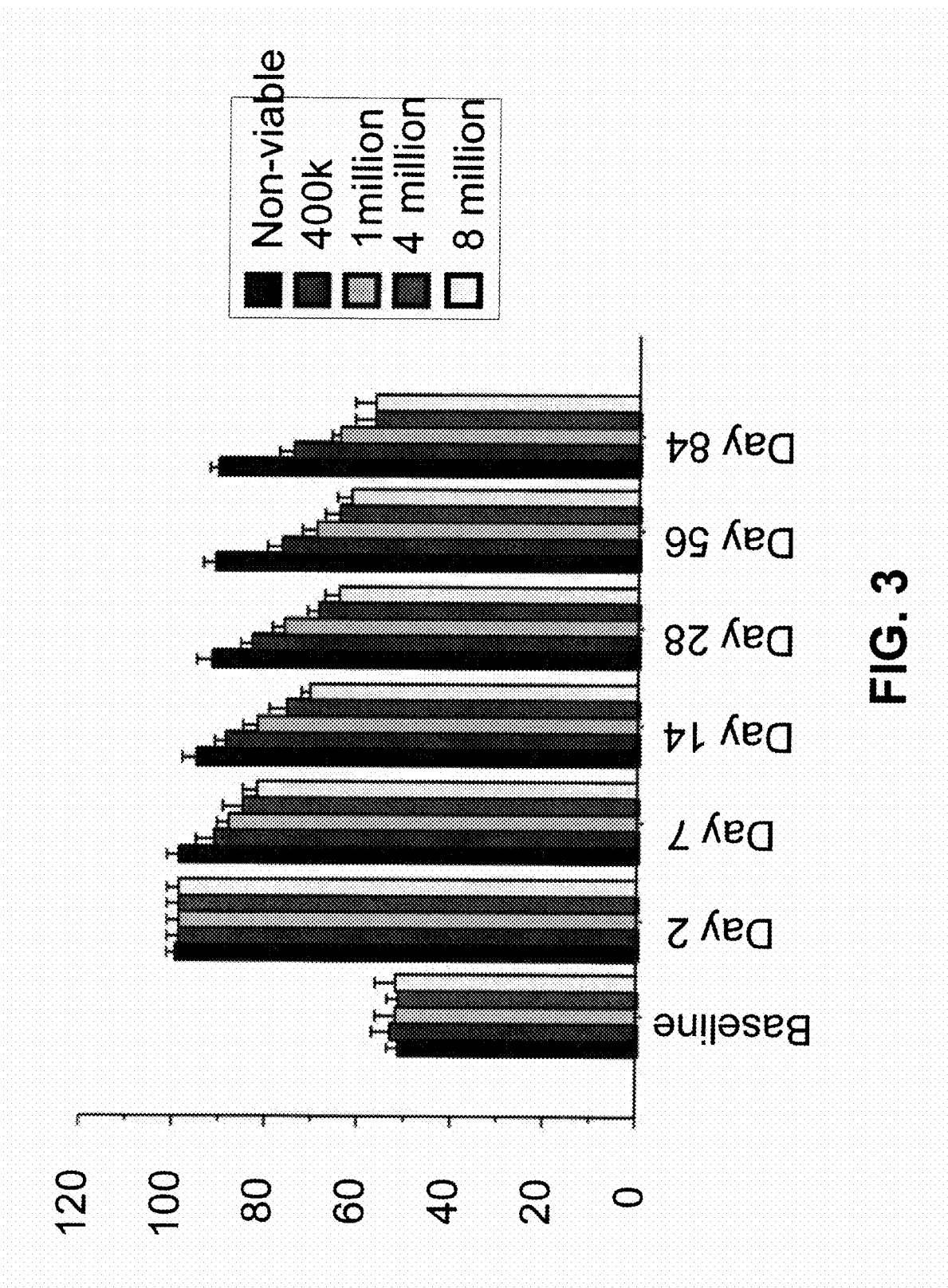

FIG. 3: Results of Elevated Body Swing Test. Vertical axis: percent biased swing activity. Horizontal axis: day that swing activity is assessed. The Baseline is the percent biased swing activity prior to induced ischemia. Percent biased swing activity was also assessed at Day 2 post-infarct at the time isolated placental cells were administered intravenously, and again at days 7 and 14 post-infarct. Nonviable: nonviable placental stem cells. 4×10$^5$, 1×10$^6$, 4×10$^6$ or 8×10$^6$ viable isolated placental cells were administered (legend).

Figure 4:
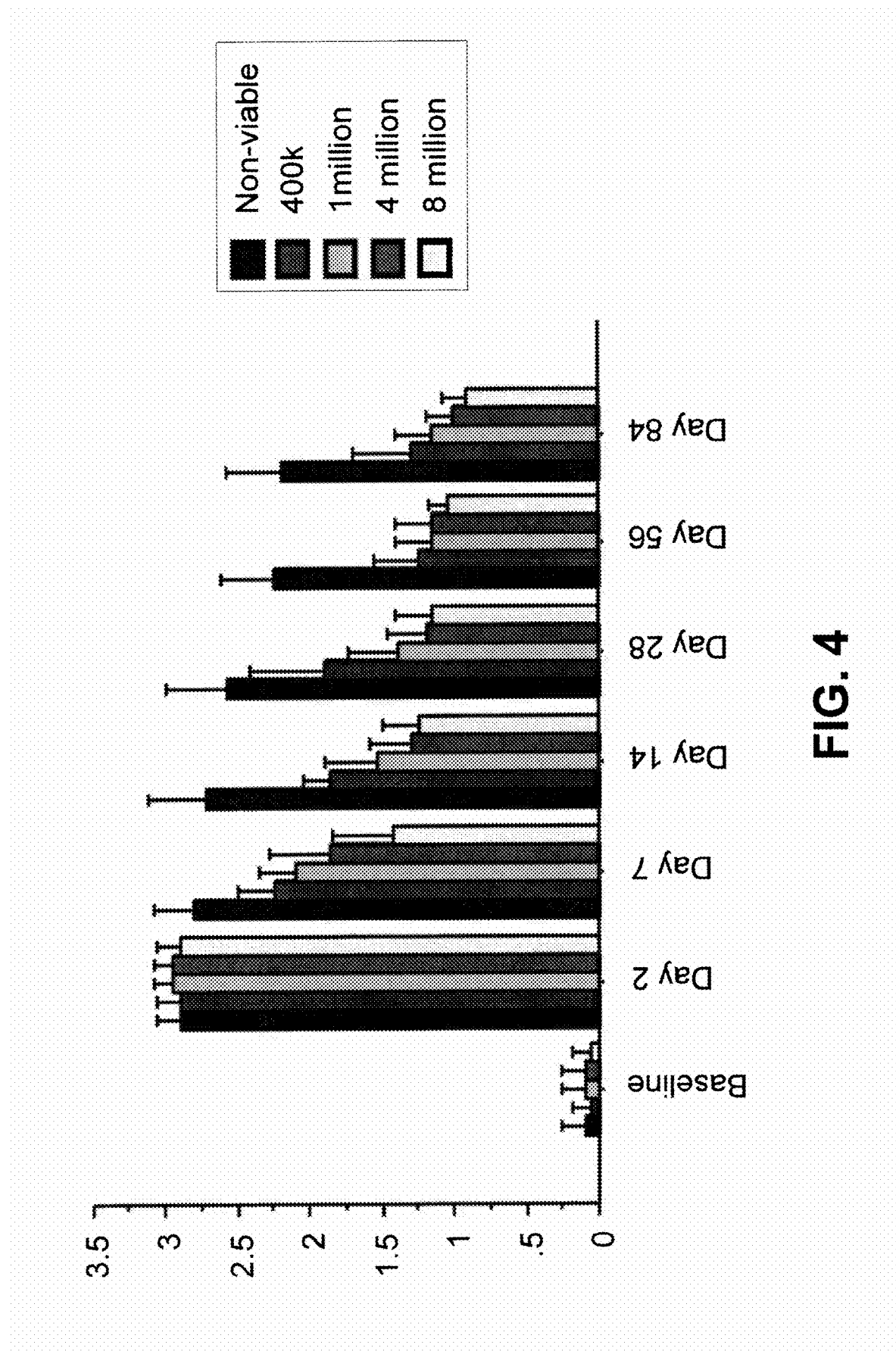

FIG. 4: Results of Bederson Test. Vertical axis: Mean Neurologic Deficit Score. Horizontal axis: day that neurologic deficit is assessed. Baseline is the neurologic deficit prior to induced ischemia; 0 indicates no deficit. Mean neurologic activity was also assessed at Day 2 post-infarct at the time isolated placental cells were administered intravenously, and again at days 7 and 14 post-infarct. Nonviable: nonviable placental stem cells. $4\times10^5$, $1\times10^6$, $4\times10^6$ or $8\times10^6$ viable isolated placental cells were administered (legend).

Figure 5:
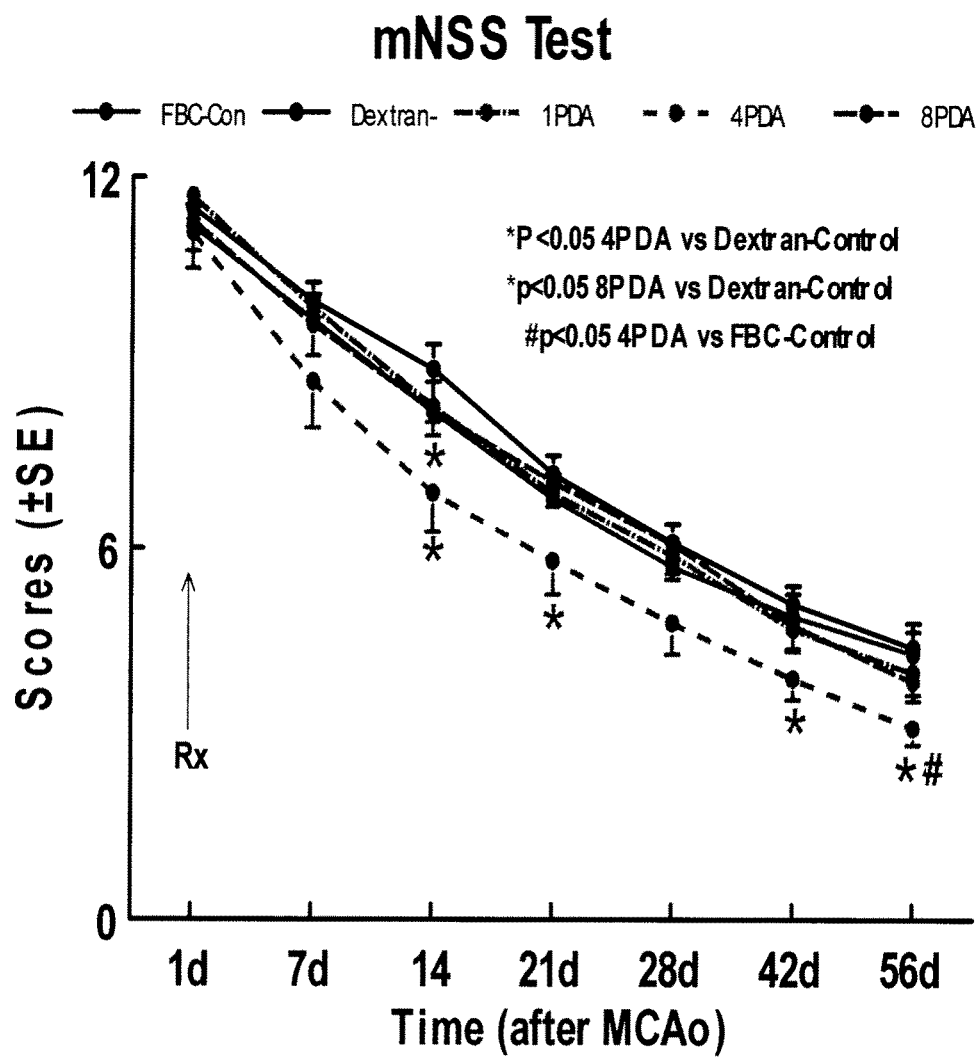

FIG. 5: Results of Modified Neural Severity Score test. Y-axis: score (see Table 1 for scoring method). X-axis: Days after middle cerebral artery occlusion (MCAO) surgery. PDA: Placental stem cells; FBC-Control: fibroblast control; Dextran, control with no cells; 1PDA, $1\times10^6$ cells; 4PDA, $4\times10^6$ cells; 8PDA, $8\times10^6$ cells. Rx: Administration of cells or dextran.

Figure 6:
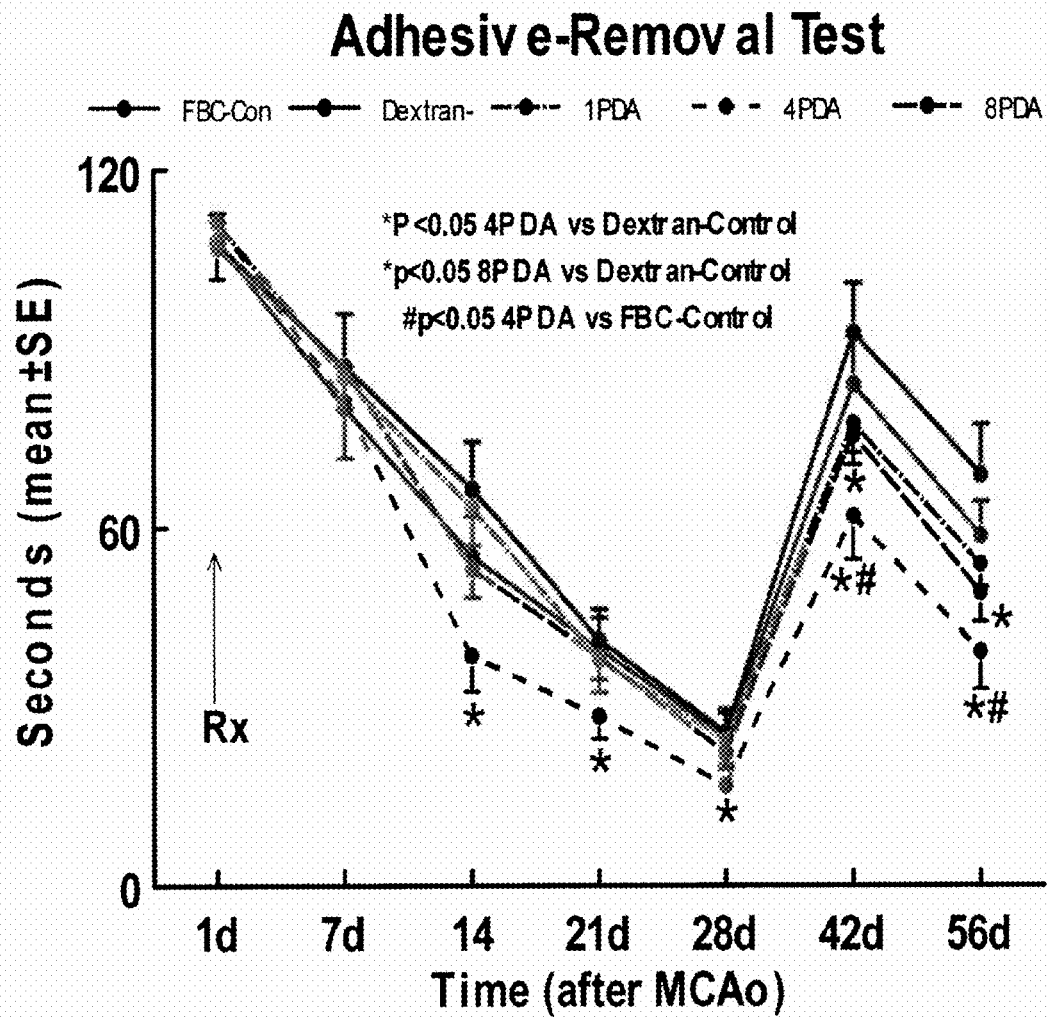

FIG. 6: Results of adhesive-removal somatosensory test. Y-axis: Number of seconds for removal of adhesive test article. X-axis: Days after middle cerebral artery occlusion (MCAO) surgery. PDA: Placental stem cells; FBC-Control: fibroblast control; Dextran, control with no cells; 1PDA, $1\times10^6$ cells; 4PDA, $4\times10^6$ cells; 8PDA, $8\times10^6$ cells. Rx: Administration of cells or dextran.

Figure 7:
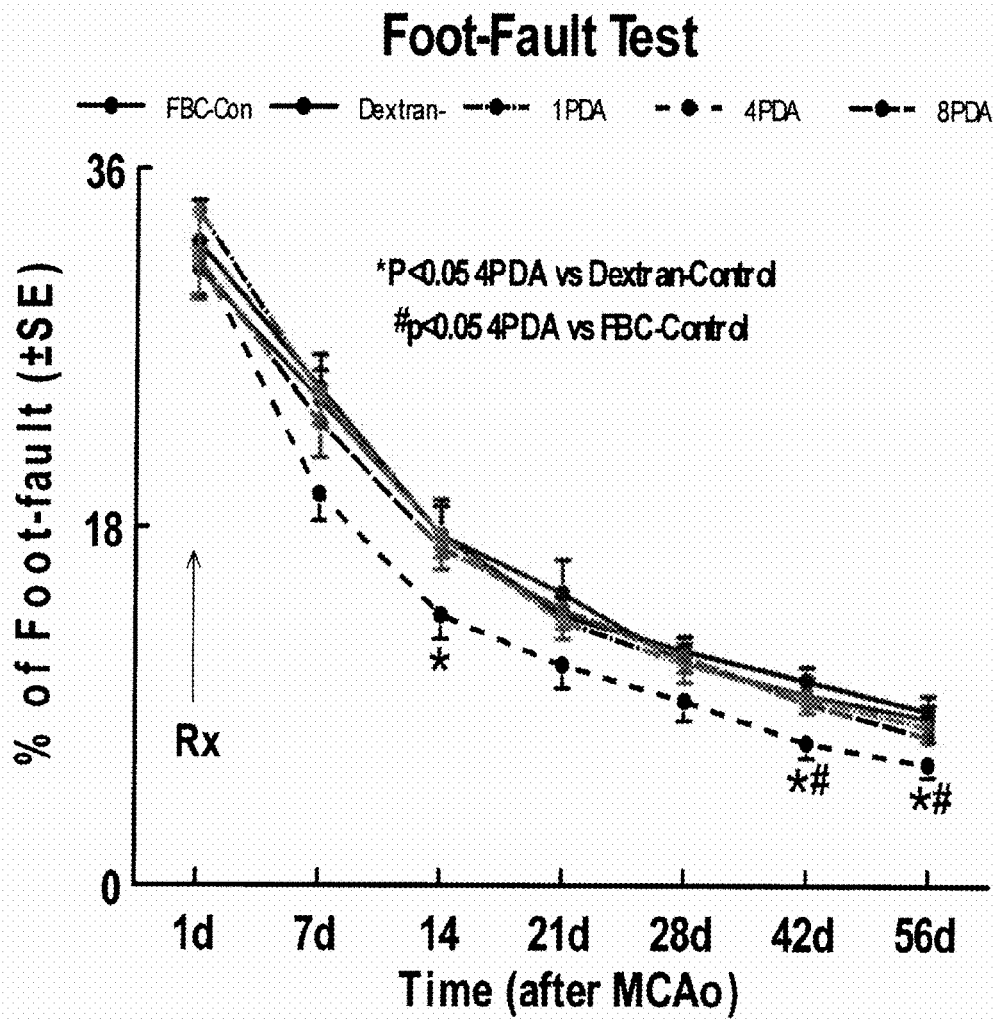

FIG. 7: Results of foot-fault test. Y-axis: Percent foot faults, out of 100 steps, on a metal grid. X-axis: Number of days after treatment (Rx) foot fault test was performed. *: Significant ($p<0.05$) improvement in foot fault test for animal receiving $4\times10^6$ placental stem cells (PDA-4M) vs. vehicle control. #: Significant ($p<0.05$) improvement in foot fault test for animal receiving $4\times10^6$ placental stem cells (PDA-4M) vs. fibroblast control.

Figure 8:
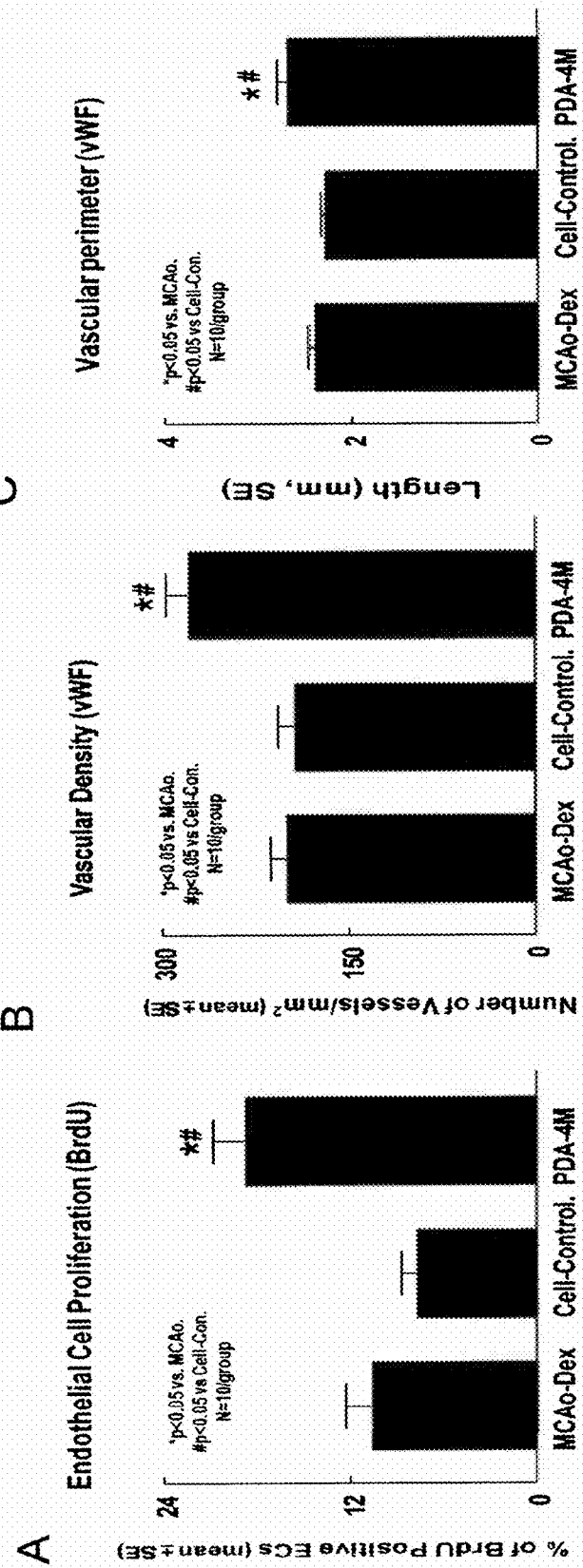

FIG. 8: Angiogenesis measurement at 56 days post-treatment after Middle Cerebral Artery occlusion. Placental stem cell treatment significantly increases endothelial cell proliferation, and vascular density and vascular perimeter in the ischemic boundary zone (IBZ). N=10/group. FIG. 8A: Anti-BrdU antibody staining detected in paraffinized brain sections. Y-axis: Percent BrdU-positive endothelial cells (ECs) in the boundary of the ischemic lesion; X-axis: experimental conditions (MCAo-Dex: Middle Cerebral Artery occlusion-dextran (initial condition pre-treatment); Cell-control: administration of fibroblasts; PDA-4M: administration of $4\times10^6$ placental stem cells). #: significant ($p<0.05$) increase in endothelial cell proliferation in the PDA-4M condition vs. fibroblast control. *: Significant ($p<0.05$) increase in endothelial cell proliferation in the PDA-4M condition vs. dextran (vehicle) control. FIG. 8B: Vascular density in the ischemic boundary zone after treatment with placental stem cells. Y-axis: number of vessels per $mm^3$; X-axis: experimental conditions (MCAo-Dex: Middle Cerebral Artery occlusion-dextran (initial condition pre-treatment); Cell-control: administration of fibroblasts; PDA-4M: administration of $4\times10^6$ placental stem cells). #: significant ($p<0.05$) increase in vessel density in the PDA-4M condition vs. fibroblast control. *: Significant ($p<0.05$) increase in vessel density in the PDA-4M condition vs. dextran (vehicle) control. FIG. 8C: Increase in vascular perimeter around ischemic boundary zone. Y-axis: length of vascular perimeter in millimeters; X-axis: experimental conditions (MCAo-Dex: Middle Cerebral Artery occlusion-dextran (initial condition pre-treatment); Cell-control: administration of fibroblasts; PDA-4M: administration of $4\times10^6$ placental stem cells). #: significant ($p<0.05$) increase in the length of the vascular perimeter in the PDA-4M condition vs. fibroblast control. *: Significant ($p<0.05$) increase the length of the vascular perimeter in the PDA-4M condition vs. dextran (vehicle) control.

Figure 9:
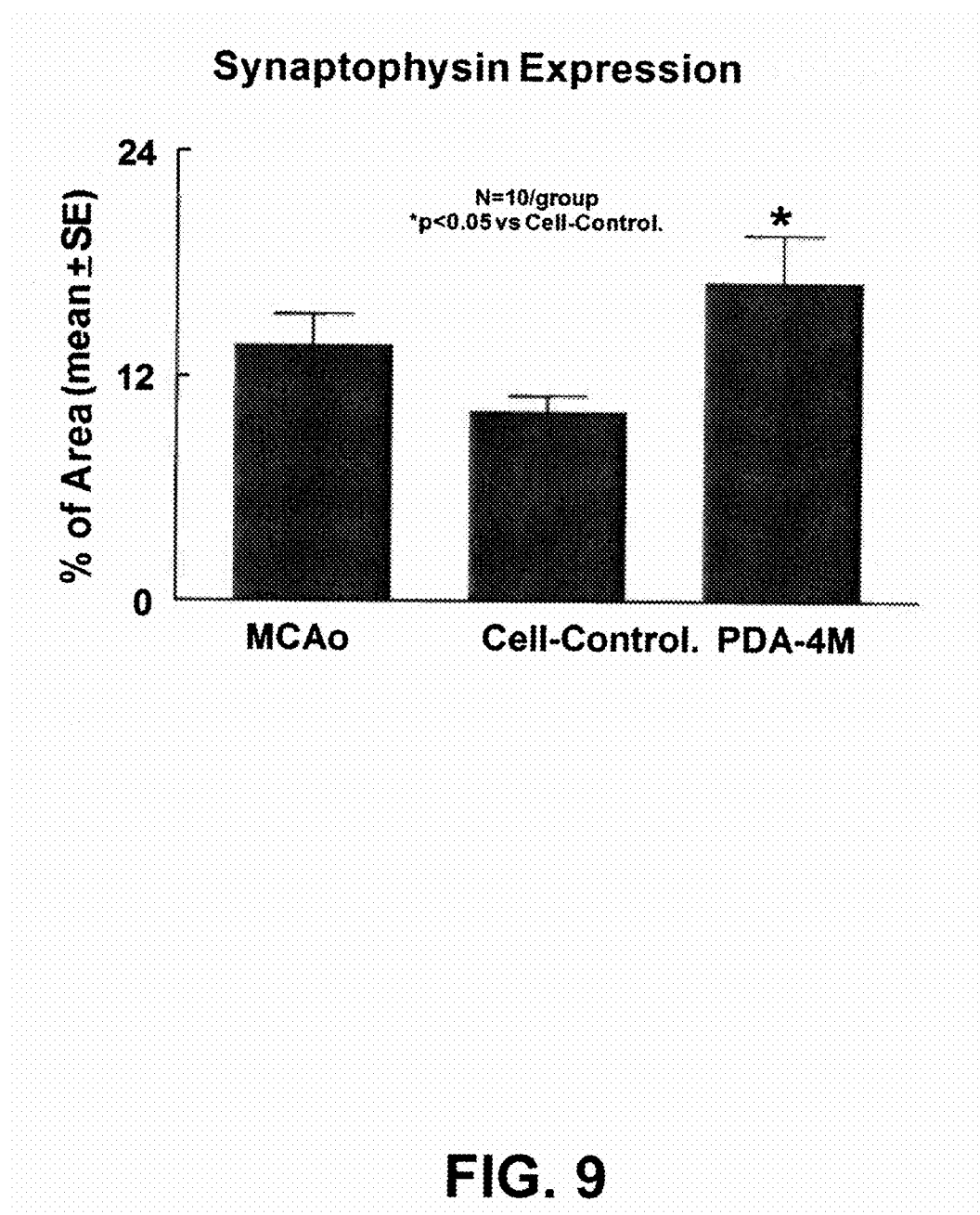

FIG. 9: Placental stem cell treatment significantly increases Synaptophysin expression in the ischemic border of the ischemic brain. N=10/group. Y-axis: % examined area in a paraffinized brain section in which synaptophysin is detected; X-axis: experimental conditions. MCAo: Synaptophysin expression at the time of Middle Cerebral Artery occlusion; Cell-control: administration of fibroblasts; PDA-4M: administration of $4\times10^6$ placental stem cells). *: Significant increase in synaptophysin expression area in PDA-4M vs. fibroblast cell control.

5. DETAILED DESCRIPTION

5.1 Treatment of Disruptions of Blood Flow in and Around the Brain

Provided herein are methods for the treatment of an individual having a disruption of the flow of blood in or around the individual's brain, e.g., treatment of one or more symptoms or neurological deficit attributable to the disruption of blood flow in or around the individual's brain, comprising administering to the individual a therapeutically effective amount of isolated tissue culture plastic-adherent human placental cells, wherein said isolated placental cells have characteristics of multipotent cells or stem cells, and wherein said isolated placental cells are not bone marrow-derived mesenchymal cells, adipose-derived mesenchymal stem cells, or mesenchymal cells obtained from umbilical cord blood, placental blood, or peripheral blood. In certain embodiments, the injury is hypoxic injury or anoxic injury. In certain embodiments provided herein, said therapeutically effective amount is an amount that results in the elimination of, a detectable improvement in, lessening of the severity of, or slowing of the progression of one or more symptoms of, or neurological deficit attributable to, the disruption of blood flow in or around the individual's brain exhibited by said individual.

In a specific embodiment, the one or more symptoms or neurological deficit, e.g., symptom of stroke, hypoxic injury or anoxic injury, is attributable at least in part, or wholly, to reperfusion injury following disruption of the flow of blood. As used herein, "reperfusion injury" refers to tissue damage caused when interrupted blood supply returns to tissue after a period of ischemia. The absence of blood-borne oxygen and nutrition during ischemia creates a condition in which the restoration of circulation results in inflammation and oxidative damage through the induction of oxidative stress rather than the restoration of normal function.

As used herein, the term "disruption of the flow of blood in or around the brain" in the context of treatment of such a disruption, encompasses treatment of one or more symptoms exhibited by an individual having the disruption and treatment of neurological deficits in the individual that are attributable to the disruption, e.g., one or more symptoms of stroke, hypoxic injury or anoxic injury. In certain embodiments, the one or more symptoms are one or more symptoms attributable primarily, or wholly, to ischemia itself. In certain other embodiments, the one or more symptoms are one or more symptoms attributable primarily, or wholly, to reperfusion injury, e.g., associated with ischemia.

5.2 Stroke

The disruption of blood flow in or around the brain or CNS treatable by the methods provided herein can be any disruption of the flow of blood that causes one or more detectable symptoms or neurological deficits in the affected individual (see below). In certain embodiments, the disruption of blood flow is a stroke, e.g., an ischemic stroke or a hemorrhagic stroke, e.g., an intracranial cerebral hemorrhage. In certain other embodiments, the disruption of blood flow is a hemorrhage outside the brain, e.g., a dural hematoma, a subdural hematoma or subarachnoid hematoma. In certain other embodiments, the disruption of flow of blood is transient, e.g., a Transient Ischemic Attack (TIA). In certain other embodiments, the disruption of blood flow is a vasospasm. In a specific embodiment, the disruption of blood flow in the brain occurs in the cerebrum. In more specific embodiments, the disruption occurs in the parietal lobe, frontal lobe, temporal lobe, or occipital lobe of the cerebrum. In another specific embodiment, the disruption occurs in the cerebellum. In another specific embodiment, the disruption occurs in the brainstem or spinal column. In certain embodiments, the disruption causes hypoxic injury or anoxic injury In one embodiment, provided herein is a method of treating an individual suffering from hypoxic injury or anoxic injury, e.g., stroke (e.g., a stroke victim) comprising administering to said individual a therapeutically effective amount of isolated, tissue culture plastic-adherent placental cells, as described herein, e.g., in Section 5.4.2, below. In a specific embodiment, said therapeutically effective amount is an amount that results in the elimination of, a detectable improvement in, lessening of the severity of, or slowing of the progression of one or more symptoms of stroke exhibited by said individual. The isolated placental cells, e.g., a plurality or isolated population of isolated placental cells, can be any of the isolated placental cells described elsewhere herein, e.g., in Section 5.4.2, below.

Stroke treatable according to the methods provided herein can be stroke attributable to any cause. In a specific embodiment, the stroke is ischemic stroke. In more specific embodiments, the ischemic stroke is thrombotic stroke or embolic stroke. In another specific embodiment, the stroke is due to systemic hypoperfusion, i.e., a reduction of blood flow to all parts of the body; or is due to venous thrombosis. In other specific embodiments, the ischemic stroke is caused by fibrillation of the heart, e.g., atrial fibrillation; paroxysmal atrial fibrillation; rheumatic disease; mitral or aortic valve disease; artificial heart valves; cardiac thrombus of the atrium or ventricle; sick sinus syndrome; sustained atrial flutter; myocardial infarction; chronic myocardial infarction together with ejection fraction of less than 28 percent; symptomatic congestive heart failure with ejection fraction of less than 30 percent; cardiomyopathy; endocarditis, e.g., Libman-Sacks endocarditis, Marantic endocarditis or infective endocarditis; papillary fibroelastoma; left atrial myxoma; coronary artery bypass graft surgery; calcification of the annulus of the mitral valve; patent foramen ovale; atrial septal aneurysm, left ventricular aneurysm without thrombus, isolated left atrial "smoke" on echocardiography without mitral stenosis or atrial fibrillation; and/or complex atheroma in the ascending aorta or proximal arch.

In another specific embodiment, the stroke is hemorrhagic stroke. In more specific embodiments, the hemorrhagic stroke is caused by intra-axial hemorrhage (leakage of blood inside the brain). In another more specific embodiment, said hemorrhagic stroke is caused by extra-axial hemorrhage (blood inside the skull but outside the brain). In more specific embodiments, the stroke is caused by intraparenchymal hemorrhage, intraventricular hemorrhage (blood in the ventricular system), epidural hematoma (bleeding between the dura mater and the skull), subdural hematoma (bleeding in the subdural space), or subarachnoid hemorrhage (between the arachnoid mater and pia mater). Most hemorrhagic stroke syndromes have specific symptoms (e.g. headache, previous head injury). In other more specific embodiments, the hemorrhagic stroke is caused by or associated with hypertension, trauma, bleeding disorders, amyloid angiopathy, illicit drug use (e.g. amphetamines or cocaine), or a vascular malformation.

In another embodiment, provided herein is a method of treatment of an individual having a disruption of the flow of blood in or around the individual's brain or CNS, e.g., treatment of one or more symptoms or neurological deficit attributable to the disruption of blood flow in or around the individual's brain or CNS comprising administering to said individual a therapeutically effective amount of isolated placental cells, e.g., placental stem cells or placental multipotent cells, wherein said disruption of the flow of blood arises from an immediate cause other than stroke, e.g., a closed-head injury or non-impact-related hematoma. In a specific embodiment, said therapeutically effective amount is an amount that results in the elimination of, a detectable improvement in, lessening of the severity of, or slowing of the progression of one or more symptoms of the disruption exhibited by said individual. As with stroke, the isolated placental cells can be any of the placental cells, e.g., placental stem cells or placental multipotent cells, described elsewhere herein, e.g., in Section 5.4.2, below.

As noted above, in certain embodiments, the method of treatment provided herein results in the elimination of, a detectable improvement in, a lessening of the severity of, or a slowing of the progression of one or more symptoms of a disruption of blood flow in or around the brain or CNS or a neurological deficit attributable to a disruption of blood flow in or around the brain or CNS, e.g., stroke, hematoma, e.g., causing hypoxic injury or anoxic injury. In specific embodiments, said symptoms or neurological deficits comprise hemiplegia (paralysis of one side of the body); hemiparesis (weakness on one side of the body); muscle weakness of the face; numbness; reduction in sensation; altered smell, taste, hearing, or vision; loss of smell, taste, hearing, or vision; drooping of eyelid (ptosis); weakness of ocular muscles; decreased gag reflexes; decreased ability to swallow; decreased pupil reactivity to light; decreased sensation of the face; decreased balance; nystagmus; altered breathing rate; altered heart rate; weakness in sternocleidomastoid muscle with decreased ability or inability to turn the head to one side; weakness in the tongue; aphasia (inability to speak or understand language); apraxia (altered voluntary movements); a visual field defect; a memory deficit; hemineglect or hemispatial neglect (deficit in attention to the space on the side of the visual field opposite the lesion); disorganized thinking; confusion; development of hypersexual gestures; anosognosia (persistent denial of the existence of a deficit); difficulty walking; altered movement coordination; vertigo; disequilibrium; loss of consciousness; headache; and/or vomiting.

The severity of disruption of the flow of blood in or around the brain or CNS, e.g., severity of stroke, or of stroke symptoms and/or neurological deficits attributable to stroke, can be assessed using one or more widely-accepted neurological function scales.

For example, in one embodiment, provided herein a method of treatment of an individual who has a disruption of the flow of blood in or around the individual's brain or CNS, e.g., an individual who has a symptom or neurological deficit attributable to a disruption of the flow of blood in or around the individual's brain, e.g., hypoxic injury or anoxic injury, comprising administering to said individual a therapeutically effective amount of isolated human adherent placental cells, wherein said therapeutically effective amount is an amount of placental cells sufficient to result in a detectable, or detectable and sustained, improvement in the individual's neurological function as assessed by one or more of the Modified Rankin Scale, NIH Stroke Scale, Canadian Neurological Scale (CNS), Glasgow Coma Scale (GCS), Hempispheric Stroke Scale, Hunt & Hess Scale, Mathew Stroke Scale, Mini-Mental State Examination (MMSE), Orgogozo Stroke Scale, Oxfordshire Community Stroke Project Classification (Bamford), Scandinavian Stroke Scale, Japan Coma Scale (JCS), Barthel Index and/or Japan Stroke Scale (JSS). In specific embodiments, the improvement is detectable within 1, 2, 3, 4, 5, or 6 days, or within 1, 2, 3, 4, 5, 6, 8, 9, 10, 11 or 12 weeks after initial assessment, and after one or more administrations of isolated placental cells. In other specific embodiments, said initial assessment is performed within 1, 2, 3, 4, 5, 6, 7, 8, 9, 10, 11, 12, 13, 14, 15, 16, 17, 18, 19, 20, 21, 22 or 23 hours, or within 1, 2, 3, 4 or 5 days after development of one or more symptoms of stroke. In other embodiments, the improvement, however determined, is sustained, e.g., over at least 1, 2, 3, 4, 5, 6, 7, 8, 9, 10, 11 or 12 months, or 1, 2, 3, 4, 5 or more years.

5.3 Administration of Isolated Placental Cells

The isolated placental cells used in the methods of treatment provided herein can be administered to an individual exhibiting one or more symptoms or neurological deficits caused by or attributable to a disruption of blood flow in or around the brain or CNS of the individual by any medically-acceptable method or route. In one embodiment, the therapeutically effective amount of isolated placental cells is administered to the individual intracranially, e.g., to an ischemic or hemorrhagic site in the affected brain or CNS of the individual. For intracranial administration, the situs of stroke (e.g., the affected area) may be visualized, e.g., by CT scanning, magnetic resonance imaging (MRI) (e.g., T1-, T2-, diffusion- and/or perfusion-weighted MR), cobalt-55 Positron Emission tomography, or similar technology. In another embodiment, said isolated placental cells are administered to the individual intravenously or intra-arterially. In other embodiments, the therapeutically effective amount of isolated placental cells is administered to the individual intramuscularly, intraperitoneally, intradermally, subcutaneously, intraocularly or parenterally. The isolated placental cells can be administered by bolus injection, or by intravenous infusion. In a specific embodiment, said intravenous infusion is intravenous infusion over about 1 to about 8 hours. In certain embodiments, the isolated placental cells are administered to the individual by a combination of routes, e.g., intracranially and by intravenous infusion.

The therapeutically effective amount of isolated placental cells can vary according to the age and/or size of the individual, and the approximate volume of the ischemic area. The approximate volume and location of the ischemic area can be estimated, e.g., by serial magnetic resonance imaging images or computed tomography (CT) scanning.

The number of isolated placental cells administered, e.g., in a single dose, can be about, or at least, or more than, e.g., $1 \times 10^5$, $5 \times 10^5$, $1 \times 10^6$, $5 \times 10^6$, $1 \times 10^7$, $5 \times 10^7$, $1 \times 10^8$, $5 \times 10^8$, $1 \times 10^9$, $5 \times 10^9$, $1 \times 10^{10}$, $5 \times 10^{10}$, $1 \times 10^{11}$ or $5 \times 10^{11}$ isolated placental cells per administration. In specific embodiments, an individual suffering from a disruption of blood flow in or around the brain or CNS, e.g., an individual suffering from a stroke, anoxic injury or hypoxic injury, can be administered between about $5 \times 10^7$ to about $3 \times 10^9$ isolated placental cells intravenously. In more specific embodiments, an individual suffering from a disruption of blood flow in or around the brain or CNS, e.g., an individual suffering from a stroke, hypoxic injury or anoxic injury, can be administered about $9 \times 10^7$ isolated placental cells, about $3.6 \times 10^8$ isolated placental cells, about $9 \times 10^8$ isolated placental cells, or about $1.8 \times 10^9$ isolated placental cells intravenously. In another specific embodiment, the individual is administered one dose of about $2 \times 10^8$ isolated placental cells intravenously. In another specific embodiment, the individual is administered one dose of about $8 \times 10^8$ isolated placental cells intravenously. In another specific embodiment, the individual is administered two doses, each comprising about $2 \times 10^8$ isolated placental cells, intravenously. In another specific embodiment, the individual is administered two doses, each comprising about $8 \times 10^8$ isolated placental cells, intravenously. In other more specific embodiments, an individual suffering from a disruption of blood flow in or around the brain or CNS, e.g., an individual suffering from a stroke, hypoxic injury or anoxic injury, can be administered between about $5 \times 10^7$ and $1 \times 10^8$ isolated placental cells intracranially. In a more specific embodiment, said individual is administered about $9 \times 10^7$ isolated placental cells intracranially.

An individual suffering from a disruption of the flow of blood in or around the brain or CNS, a symptom of the disruption, and/or a neurological deficit attributable to the disruption, can be administered isolated placental cells once, or more than once, e.g., two or more times in the course of treatment. The isolated placental cells can be administered in a suitable volume for intracranial administration, e.g., in about 100 µL, 200 µL, 300 µL, 400 µL, 500 µL, 600 µL, 700 µL, 800 µL, 900 µL, 1000 µL, 1.5 mL, 2 mL, 2.5 mL, 3 mL, 3.5 mL, 4 mL, 4.5 mL, 5 mL, 5.5 mL, 6.0 mL, 6.5 mL, 7 mL, 7.5 mL, 8 mL, 8.5 mL, 9 mL, 9.5 mL, 10 mL, 11 mL, 12 mL, 13 mL, 14 mL, 15 mL, 16 mL, 17 mL, 18 mL, 19 mL, 20 mL, 21 mL, 22 mL, 23 mL, 24 mL, 25 mL, 26 mL, 27 mL, 28 mL, 29 mL, or about 30 mL of a pharmaceutically-acceptable solution. For intravenous administration, a plurality of isolated placental cells (e.g., about $1 \times 10^5$, $5 \times 10^5$, $1 \times 10^6$, $5 \times 10^6$, $1 \times 10^7$, $5 \times 10^7$, $1 \times 10^8$, $5 \times 10^8$, $1 \times 10^9$, $5 \times 10^9$, $1 \times 10^{10}$, $5 \times 10^{10}$, $1 \times 10^{11}$ or $5 \times 10^{11}$) isolated placental cells can be delivered in, e.g., about, or no more than, 100 mL, 150 mL, 200 mL, 250 mL, 300 mL, 350 mL, 400 mL, 450 mL, 500 mL, 550 mL, 600 mL, 650 mL, 700 mL, 750 mL, 800 mL, 850 mL, 900 mL, 950 mL, 1000 mL, 1.1 L, 1.2 L, 1.3 L, 1.4 L, or 1.5 L, e.g., by intravenous infusion.

In other embodiments, between about $1 \times 10^6$ and about $2 \times 10^6$ isolated placental cells per kilogram of an individual (e.g., an individual having one or more symptoms or neurological deficits caused by or attributable to a disruption of blood flow in or around the brain or CNS, or of reperfusion injury); between about $2 \times 10^6$ and about $3 \times 10^6$ isolated placental cells per kilogram of said individual; between about $3 \times 10^6$ and about $4 \times 10^6$ isolated placental cells per kilogram of said individual; between about $4 \times 10^6$ and about $5 \times 10^6$ isolated placental cells per kilogram of said individual; between about $5 \times 10^6$ and about $6 \times 10^6$ isolated placental cells per kilogram of said individual; between about $6 \times 10^6$ and about $7 \times 10^6$ isolated placental cells per kilogram of said individual; between about $7 \times 10^6$ and about $8 \times 10^6$ isolated placental cells per kilogram of said individual; between about $8 \times 10^6$ and about $9 \times 10^6$ isolated placental cells per kilogram of said individual; or between about $9 \times 10^6$ and about $1 \times 10^7$ isolated placental cells per kilogram of said individual are administered to said individual. In another specific embodiment, said administering comprises administering between about $1 \times 10^7$ and about $2 \times 10^7$ isolated placental cells per kilogram of said individual to said individual. In another specific embodiment, said administering comprises administering between about $1.3 \times 10^7$ and about $1.5 \times 10^7$ isolated placental cells per kilogram of said individual to said individual. In another specific embodiment, said administering comprises administering up to about 3×10⁷ isolated placental cells per kilogram of said individual to said individual. In another specific embodiment, said administering comprises administering about 15×10⁷ isolated placental cells in about 20 milliliters of solution to said individual. In a preferred embodiment, administration of isolated placental cells comprises administration of no more than 7.5×10⁶ isolated placental cells per kg of a recipient, in no more than about 1 liter of solution. In a specific embodiment, said administering comprises administering between about 5×10⁶ and about 2×10⁷ isolated placental cells to said individual, e.g., intracranially. In a specific embodiment, said administering comprises administering between about 5×10⁶ and about 3×10⁷ isolated placental cells per kg to said individual, wherein said cells are contained in a solution comprising 10% dextran, 5% human serum albumin, and optionally an immunosuppressant, e.g., cyclosporine A, e.g., intracranially. In another specific embodiment, said administering comprises administering between about 1×10⁹ and about 3×10⁹ placental multipotent cells to said individual, wherein said cells are contained in a solution comprising 10% dextran, 5% human serum albumin, and optionally an immunosuppressant, e.g., cyclosporine A. In another specific embodiment, said administering comprises administering about 15×10⁷ to about 25×10⁷ isolated placental cells in about 20 milliliters of solution to said individual. In any of the above embodiments, the isolated placental cells can be administered intravenously or intraarterially, e.g., as a bolus or drip. In yet another specific embodiment, said administering comprises administering about 200 million cells in about 20 milliliters of solution to said individual.

The isolated placental cells can be infused for any medically-acceptable period of time. In various embodiments, for example, the number of isolated placental cells described above can be administered, e.g., infused, e.g., intravenously or intraarterially, over the course of about, or no more than, 15, 20, 25, 30, 35, 40, 45, 50 or 55 minutes, or over the course of about, or no more than, 1 hour, or 1.5, 2, 2.5, 3, 3.5, 4, 4.5, 5, 5.5 or 6 hours.

Isolated placental cells can be administered to an individual having a disruption in the flow of blood in or around the brain or CNS at any time after development of one or more symptoms of or neurological deficits, e.g., hypoxic injury or anoxic injury, attributable to, the individual's disruption in the individual. In various embodiment, isolated placental cells are administered within the first 21, 20, 19, 18, 17, 16, 15, 14, 13, 12, 11, 10, 9, 8, 7, 6, 5, 4, 3 or 2 days of development of the first symptom or neurological deficit exhibited by the individual; preferably isolated placental cells are administered within the first 48, 47, 46, 45, 44, 43, 42, 41, 40, 39, 38, 37, 36, 35, 34, 33, 32, 21, 30, 29, 28, 27, 26, 25, 24, 23, 22, 21, 20, 19, 18, 17, 16, 15, 14, 13, 12, 11, 10, 9, 8, 7, 6, 5, 4, 3, or 2 hours of development of the first detectable symptom or neurological deficit in the individual, or within the first hour of development of the first detectable symptom or neurological deficit in the individual.

In other embodiments, the isolated placental cells are administered prophylactically, e.g., before one or more symptoms of said disruption of flow of blood in or around the brain or CNS, symptom of stroke, hypoxic injury or anoxic injury manifests, or is detectable.

Treatment of an individual having a disruption of the flow of blood in or around the brain or CNS of an individual, comprising administration of isolated placental cells to the individual, can further comprise administration to the individual of one or more second therapeutic agents. Such second therapeutic agents can be administered before administration of isolated placental cells, during administration of the isolated placental cells, or after administration of the isolated placental cells. Said second therapeutic agents can be administered fewer, more, or an equal number of times as the isolated placental cells are administered.

A second therapeutic agent can be any agent that has therapeutic benefit to an individual having a disruption of blood flow in or around the brain or CNS. In one embodiment, the therapeutic agent is an agent, e.g., a drug, that is used to treat stroke, hypoxic injury or anoxic injury. In a specific embodiment, the second therapeutic agent is a neuroprotective agent. In a specific embodiment, the neuroprotective agent is disufenton sodium (NXY-059; the disulfonyl derivative of phenylbutylnitrone), the structure of which is shown below:

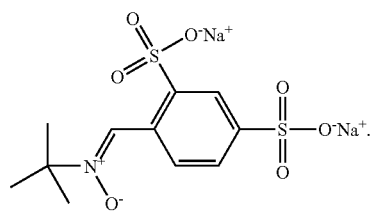

In another embodiment, in which the individual suffers from hemorrhagic stroke, the second therapeutic agent is a therapeutic agent that lowers blood pressure of said individual. In another embodiment, the second therapeutic agent is a thrombolytic agent. In a specific embodiment, the thrombolytic agent is tissue plasminogen activator (tPA). The tPA can be from a natural source or recombinant. In a more specific embodiment, the tPA is administered within the first three hours after development of one or more symptoms or neurological deficits in the individual. In another more specific embodiment, the tPA is administered after the first three hours after development of one or more symptoms of stroke in a stroke victim. In certain embodiments, the use of a thrombolytic agent is contraindicated, e.g., when the stroke victim has a head injury, or when the stroke is caused by a head injury. In another specific embodiment, the second therapeutic agent is an anticoagulant or an antiplatelet agent. In embodiments in which the disruption of flow of blood in or around the brain or CNS is a hemorrhage, the second therapeutic agent can be an antihypertensive drug, e.g., a beta blocker or diuretic drug, a combination of a diuretic drug and a potassium-sparing diuretic drug, a combination of a beta blocker and a diuretic drug, a combination of an angiotensin-converting enzyme (ACE) inhibitor and a diuretic, an angiotensin-II antagonist and a diuretic drug, and/or a calcium channel blocker and an ACE inhibitor. In another embodiment, the second therapeutic agent is administered in order to reduce intracranial pressure. In a more specific embodiment, the second therapeutic agent is a diuretic.

In embodiments in which the administered isolated placental cells are not autologous to the individual having a disruption of flow of blood in or around the brain or CNS, the second therapeutic agent can be an immunosuppressive agent. Immunosuppressive agents are well-known in the art and include, e.g., anti-T cell receptor antibodies (monoclonal or polyclonal, or antibody fragments or derivatives thereof, e.g., Muromonab-CD3), anti-IL-2 receptor antibodies (e.g., Basiliximab (SIMULECT®) or daclizumab (ZENAPAX)®), azathioprine, corticosteroids, cyclosporine, tacrolimus, mycophenolate mofetil, sirolimus, calcineurin inhibitors, and the like. In a specific embodiment, the immunosuppressive agent is a neutralizing antibody to macrophage inflammatory protein (MIP)-1α or MIP-1β. Preferably, the anti-MIP-1α or MIP-1β antibody is administered in an amount sufficient to cause a detectable reduction in the amount of MIP-1α and/or MIP-1β in said individual, e.g., at the time of administration.

5.4 Isolated Placental Cells and Isolated Placental Cell Populations

The isolated placental cells useful in the treatment of individuals having a disruption of blood flow in or around the brain or CNS, including symptoms and neurological deficits attributable thereto, are cells, obtainable from a placenta or part thereof, that adhere to a tissue culture substrate and have characteristics of multipotent cells or stem cells, but are not trophoblasts. In certain embodiments, the isolated placental cells useful in the methods disclosed herein have the capacity to differentiate into non-placental cell types. The isolated placental cells useful in the methods disclosed herein can be either fetal or maternal in origin (that is, can have the genotype of either the fetus or mother, respectively). Preferably, the isolated placental cells and populations of isolated placental cells are fetal in origin. As used herein, the phrase "fetal in origin" or "non-maternal in origin" indicates that the isolated placental cells or populations of isolated placental cells are obtained from the umbilical cord or placental structures associated with the fetus, i.e., that have the fetal genotype. As used herein, the phrase "maternal in origin" indicates that the cells or populations of cells are obtained from a placental structures associated with the mother, e.g., which have the maternal genotype. Isolated placental cells, or populations of cells comprising the isolated placental cells, can comprise isolated placental cells that are solely fetal or maternal in origin, or can comprise a mixed population of isolated placental cells of both fetal and maternal origin. The isolated placental cells, and populations of cells comprising the isolated placental cells, can be identified and selected by the morphological, marker, and culture characteristics discussed below. In certain embodiments, any of the placental cells, e.g., placental stem cells or placental multipotent cells described herein, are autologous to a recipient, e.g., an individual who has had a stroke, or has a symptom of a stroke. In certain other embodiments, any of the placental cells, e.g., placental stem cells or placental multipotent cells described herein, are heterologous to a recipient, e.g., an individual who has had a stroke, or has a symptom of a stroke.

5.4.1 Physical and Morphological Characteristics

The isolated placental cells described herein, when cultured in primary cultures or in cell culture, adhere to the tissue culture substrate, e.g., tissue culture container surface (e.g., tissue culture plastic), or to a tissue culture surface coated with extracellular matrix or ligands such as laminin, collagen (e.g., native or denatured), gelatin, fibronectin, ornithine, vitronectin, and extracellular membrane protein (e.g., MATRIGEL® (BD Discovery Labware, Bedford, Mass.)). The isolated placental cells in culture assume a generally fibroblastoid, stellate appearance, with a number of cytoplasmic processes extending from the central cell body. The cells are, however, morphologically distinguishable from fibroblasts cultured under the same conditions, as the isolated placental cells exhibit a greater number of such processes than do fibroblasts. Morphologically, isolated placental cells are also distinguishable from hematopoietic stem cells, which generally assume a more rounded, or cobblestone, morphology in culture.

In certain embodiments, the isolated placental cells useful in the methods of treatment disclosed herein, when cultured in a growth medium, develop embryoid-like bodies. Embryoid-like bodies are noncontiguous clumps of cells that can grow on top of an adherent layer of proliferating isolated placental cells. The term "embryoid-like" is used because the clumps of cells resemble embryoid bodies, clumps of cells that grow from cultures of embryonic stem cells. Growth medium in which embryoid-like bodies can develop in a proliferating culture of isolated placental cells includes medium comprising, e.g., DMEM-LG (e.g., from Gibco); 2% fetal calf serum (e.g., from Hyclone Labs.); 1× insulin-transferrin-selenium (ITS); 1× linoleic acid-bovine serum albumin (LA-BSA); $10^{-9}$ M dexamethasone (e.g., from Sigma); $10^{-4}$ M ascorbic acid 2-phosphate (e.g., from Sigma); epidermal growth factor 10 ng/mL (e.g., from R&D Systems); and platelet-derived growth factor (PDGF-BB) 10 ng/mL (e.g., from R&D Systems).

5.4.2 Cell Surface, Molecular and Genetic Markers

The isolated placental cells, e.g., multipotent cells or stem cells, and populations of isolated placental cells, useful in the methods of treatment disclosed herein, are tissue culture plastic-adherent human placental cells that have characteristics of multipotent cells or stem cells, and express a plurality of markers that can be used to identify and/or isolate the cells, or populations of cells that comprise the stem cells. The isolated placental cells, and placental cell populations described herein (that is, two or more isolated placental cells) include placental cells and placental cell-containing cell populations obtained directly from the placenta, or any part thereof (e.g., amnion, chorion, placental cotyledons, and the like). Isolated placental cell populations also include populations of (that is, two or more) isolated placental cells in culture, and a population in a container, e.g., a bag. The isolated placental cells described herein are not bone marrow-derived mesenchymal cells, adipose-derived mesenchymal stem cells, or mesenchymal cells obtained from umbilical cord blood, placental blood, or peripheral blood.

In certain embodiments, the isolated placental cells are isolated placental stem cells. In certain other embodiments, the isolated placental cells are isolated placental multipotent cells. In one embodiment, the isolated placental cells are $CD34^-$, $CD10^+$ and $CD105^+$ as detected by flow cytometry. In a specific embodiment, the isolated $CD34^-$, $CD10^+$, $CD105^+$ placental cells are placental stem cells. In another specific embodiment, the isolated $CD34^-$, $CD10^+$, $CD105^+$ placental cells are multipotent placental cells. In another specific embodiment, the isolated $CD34^-$, $CD10^+$, $CD105^+$ placental cells have the potential to differentiate into cells of a neural phenotype, cells of an osteogenic phenotype, and/or cells of a chondrogenic phenotype. In another specific embodiment, the isolated $CD34^-$, $CD10^+$, $CD105^+$ placental cells are additionally $CD200^+$. In another specific embodiment, the isolated $CD34^-$, $CD10^+$, $CD105^+$ placental cells are additionally $CD45^-$ or $CD90^+$. In another specific embodiment, the isolated $CD34^-$, $CD10^+$, $CD105^+$ placental cells are additionally CD45 and $CD90^+$, as detected by flow cytometry. In a more specific embodiment, the isolated $CD34^-$, $CD10^+$, $CD105^+$, $CD200^+$ placental cells are additionally $CD90^+$ or $CD45^-$, as detected by flow cytometry. In another more specific embodiment, the isolated $CD34^-$, $CD10^+$, $CD105^+$, $CD200^+$ placental cells are additionally $CD90^+$ and $CD45^-$, as detected by flow cytometry, i.e., the cells are $CD34^-$, $CD10^+$, $CD45^-$, $CD90^+$, $CD105^+$ and $CD200^+$. In a more specific embodiment, said $CD34^-$, $CD10^+$, CD45, $CD90^+$, $CD105^+$, $CD200^+$ cells are additionally $CD80^-$ and $CD86^-$.

In a specific embodiment, any of the $CD34^-$, $CD10^+$, $CD105^+$ cells described above are additionally one or more of $CD29^+$, $CD38^-$, $CD44^+$, $CD54^+$, $SH3^+$ or $SH4^+$. In another more specific embodiment, the cells are additionally $CD44^+$.

In another specific embodiment of any of the isolated CD34−, CD10+, CD105+ placental cells above, the cells are additionally one or more of CD117−, CD133−, KDR− (VEGFR2−), HLA-A,B,C+, HLA-DP,DQ,DR−, or Programmed Death-1 Ligand (PDL1)+, or any combination thereof.

In another embodiment, the CD34−, CD10+, CD105+ cells are additionally one or more of CD13+, CD29+, CD33+, CD38, CD44+, CD45, CD54+, CD62E−, CD62L−, CD62P−, SH3+ (CD73+), SH4+(CD73+), CD80, CD86−, CD90+, SH2+ (CD105+), CD106/VCAM+, CD117−, CD144/VE-cadherin$^{low}$, CD184/CXCR4−, CD200+, CD133−, OCT-4+, SSEA3−, SSEA4−, ABC-p+, KDR− (VEGFR2−), HLA-A,B,C+, HLA-DP,DQ,DR7, HLA-G+, or Programmed Death-1 Ligand (PDL1)+, or any combination thereof. In a other embodiment, the CD34−, CD10+, CD105+ cells are additionally CD13+, CD29+, CD33+, CD38−, CD44+, CD45−, CD54/ICAM+, CD62E−, CD62L−, CD62P−, SH3+ (CD73+), SH4+ (CD73+), CD80−, CD86−, CD90+, SH2+(CD105+), CD106/VCAM+, CD117−, CD144/VE-cadherin$^{low}$, CD184/CXCR4−, CD200+, CD133−, OCT-4+, SSEA3−, SSEA4−, ABC-p+, KDR− (VEGFR2−), HLA-A,B, C+, HLA-DP,DQ,DR−, HLA-G+, and Programmed Death-1 Ligand (PDL1)+.

In certain embodiments, the cells are one or more of SSEA3-, SSEA4- or ABC-p+. The isolated placental cells can also express HLA-ABC (MHC-1). These markers can be used, in any combination, to identify the isolated placental cells, e.g., isolated placental stem cells or isolated multipotent cells and to distinguish the isolated placental cells from other cell types. Because the isolated placental cells can express CD73 and CD105, they can have mesenchymal stem cell-like characteristics. Lack of expression of CD34, CD38 and/or CD45, for example, identifies the isolated placental cells as non-hematopoietic stem cells.

Also provided herein are populations of the isolated placental cells, or populations of cells, e.g., populations of placental cells, comprising, e.g., that are enriched for, the isolated placental cells, that are useful in the methods of treatment disclosed herein. Preferred populations of cells comprising the isolated placental cells, wherein the populations of cells are useful in the methods of treatment disclosed herein, comprise, e.g., at least 10%, 15%, 20%, 25%, 30%, 35%, 40%, 45%, 50%, 55%, 60%, 65%, 70%, 75%, 80%, 85%, 90%, 95% or 98% isolated CD10+, CD105+ and CD34− placental cells; that is, at least 10%, 15%, 20%, 25%, 30%, 35%, 40%, 45%, 50%, 55%, 60%, 65%, 70%, 75%, 80%, 85%, 90%, 95% or 98% of cells in said population are isolated CD10+, CD105+ and CD34− placental cells. In a specific embodiment, the isolated CD34−, CD10+, CD105+ placental cells are additionally CD200+. In a more specific embodiment, the isolated CD34−, CD10+, CD105+, CD200+ placental cells are additionally CD90+ or CD45−, as detected by flow cytometry. In another more specific embodiment, the isolated CD34−, CD10+, CD105+, CD200+ placental cells are additionally CD90+ and CD45−, as detected by flow cytometry. In a more specific embodiment, any of the isolated CD34−, CD10+, CD105+ placental cells described above are additionally one or more of CD29+, CD38−, CD44+, CD54+, SH3+ or SH4+. In another more specific embodiment, the isolated CD34−, CD10+, CD105+ placental cells, or isolated CD34−, CD10+, CD105+, CD200+ placental cells, are additionally CD44+. In a specific embodiment of any of the populations of cells comprising isolated CD34−, CD10+, CD105+ placental cells above, the isolated placental cells are additionally one or more of CD13+, CD29+, CD33+, CD38−, CD44+, CD45−, CD54+, CD62E−, CD62L−, CD62P−, SH3+ (CD73+), SH4+ (CD73+), CD80−, CD86−, CD90+, SH2+ (CD105+), CD106/VCAM+, CD117−, CD144/VE-cadherin$^{low}$, CD184/CXCR4−, CD200+, CD133−, OCT-4+, SSEA3−, SSEA4−, ABC-p+, KDR− (VEGFR2−), HLA-A,B,C+, HLA-DP,DQ, DR−, HLA-G+, or Programmed Death-1 Ligand (PDL1)+, or any combination thereof. In a more specific embodiment, the CD34−, CD10+, CD105+ cells are additionally CD13+, CD29+, CD33+, CD38−, CD44+, CD45−, CD54/ICAM+, CD62E−, CD62L−, CD62P−, SH3+ (CD73+), SH4+ (CD73+), CD80−, CD86−, CD90+, SH2+ (CD105+), CD106/VCAM+, CD117−, CD144/VE-cadherin$^{low}$, CD184/CXCR4−, CD200+, CD133−, OCT-4+, SSEA3−, SSEA4−, ABC-p+, KDR− (VEGFR2−), HLA-A,B,C+, HLA-DP,DQ,DR−, HLA-G+, and Programmed Death-1 Ligand (PDL1)+.

In certain embodiments, the isolated placental cells useful in the methods of treatment described herein are isolated placental cells that are one or more, or all, of CD10+, CD29+, CD34−, CD38−, CD44+, CD45−, CD54+, CD90+, SH2+, SH3+, SH4+, SSEA3−, SSEA4−, OCT-4+, and ABC-p+, wherein said isolated placental cells are obtained by physical and/or enzymatic disruption of placental tissue. In a specific embodiment, the isolated placental cells are OCT-4+ and ABC-p+. In another specific embodiment, the isolated placental cells are OCT-4+ and CD34−, wherein said isolated placental cells have at least one of the following characteristics: CD10+, CD29+, CD44+, CD45−, CD54+, CD90+, SH3+, SH4+, SSEA3−, and SSEA4−. In another specific embodiment, the isolated placental cells are OCT-4+, CD34−, CD10+, CD29+, CD44+, CD45−, CD54+, CD90+, SH3+, SH4+, SSEA3−, and SSEA4−. In another embodiment, the isolated placental cells are OCT-4+, CD34−, SSEA3−, and SSEA4−. In a more specific embodiment, the isolated placental cells are OCT-4+ and CD34−, and is either SH2+ or SH3+. In a more specific embodiment, the isolated placental cells are OCT-4+, CD34−, SH2+, and SH3+. In another more specific embodiment, the isolated placental cells are OCT-4+, CD34−, SSEA3−, and SSEA4−, and are either SH2+ or SH3+. In another more specific embodiment, the isolated placental cells are OCT-4+ and CD34−, and either SH2+ or SH3+, and is at least one of CD10+, CD29+, CD44+, CD45−, CD54+, CD90+, SSEA3, or SSEA4−. In another more specific embodiment, the isolated placental cells are OCT-4+, CD34−, CD10+, CD29+, CD44+, CD45−, CD54+, CD90+, SSEA3−, and SSEA4−, and either SH2+ or SH3+.

In another embodiment, the isolated placental cells useful in the methods of treatment disclosed herein are SH2+, SH3+, SH4+ and OCT-4+. In a more specific embodiment, the isolated placental cells are CD10+, CD29+, CD44+, CD54+, CD90+, CD34, CD45, SSEA3−, or SSEA4−. In another embodiment, the isolated placental cells are SH2+, SH3+, SH4+, SSEA3− and SSEA4−. In a more specific embodiment, the isolated placental cells are SH2+, SH3+, SH4+, SSEA3− and SSEA4−, CD10+, CD29+, CD44+, CD54+, CD90+, OCT-4+, CD34 or CD45−.

In another embodiment, the isolated placental cells useful in the methods disclosed herein are CD10+, CD29+, CD34−, CD44+, CD45−, CD54+, CD90+, SH2+, SH3+, and SH4+; wherein said isolated placental cells are additionally one or more of OCT-4+, SSEA3− or SSEA4−.

In certain embodiments, isolated placental cells useful in the methods of treatment disclosed herein, e.g., treatment of disruption of blood flow in or around the brain or CNS, treatment of stroke, are CD200+ or HLA-G+. In a specific embodiment, the isolated placental cells are CD200+ and HLA-G+. In another specific embodiment, the isolated placental cells are additionally CD73+ and CD105+. In another specific embodiment, the isolated placental cells are additionally CD34−, CD38− or CD45−. In another specific embodiment, the isolated placental cells are additionally CD34⁻, CD38⁻ and CD45⁻. In another specific embodiment, said stem cells are CD34⁻, CD38⁻, CD45⁻, CD73⁺ and CD105⁺. In another specific embodiment, said isolated CD200⁺ or HLA-G⁺ placental cells facilitate the formation of embryoid-like bodies in a population of placental cells comprising the isolated placental cells, under conditions that allow the formation of embryoid-like bodies. In another specific embodiment, the isolated placental cells are isolated away from placental cells that are not stem or multipotent cells. In another specific embodiment, said isolated placental cells are isolated away from placental stem cells that do not display these markers.

In another embodiment, a cell population useful in the methods of treatment described herein is a population of cells comprising, e.g., that is enriched for, CD200⁺, HLA-G⁺ stem cells. In a specific embodiment, said population is a population of placental cells. In various embodiments, at least about 10%, at least about 20%, at least about 30%, at least about 40%, at least about 50%, or at least about 60% of cells in said cell population are isolated CD200⁺, HLA-G⁺ placental cells. Preferably, at least about 70% of cells in said cell population are isolated CD200⁺, HLA-G⁺ placental cells. More preferably, at least about 90%, 95%, or 99% of said cells are isolated CD200⁺, HLA-G⁺ placental cells. In a specific embodiment of the cell populations, said isolated CD200⁺, HLA-G⁺ placental cells are also CD73⁺ and CD105⁺. In another specific embodiment, said isolated CD200⁺, HLA-G⁺ placental cells are also CD34, CD38 or CD45. In a more specific embodiment, said isolated CD200⁺, HLA-G⁺ placental cells are also CD34, CD38⁻, CD45, CD73⁺ and CD105⁺. In another embodiment, said cell population produces one or more embryoid-like bodies when cultured under conditions that allow the formation of embryoid-like bodies. In another specific embodiment, said cell population is isolated away from placental cells that are not stem cells. In another specific embodiment, said isolated CD200⁺, HLA-G⁺ placental cells are isolated away from placental cells that do not display these markers.

In another embodiment, the isolated placental cells useful in the methods of treatment described herein are CD73⁺, CD105⁺, and CD200⁺. In another specific embodiment, the isolated placental cells are HLA-G⁺. In another specific embodiment, the isolated placental cells are CD34⁻, CD38⁻ or CD45⁻. In another specific embodiment, the isolated placental cells are CD34⁻, CD38⁻ and CD45⁻. In a more specific embodiment, the isolated placental cells are CD34⁻, CD38⁻, CD45⁻, and HLA-G⁺. In another specific embodiment, the isolated CD73⁺, CD105⁺, and CD200⁺ placental cells facilitate the formation of one or more embryoid-like bodies in a population of placental cells comprising the isolated placental cells, when the population is cultured under conditions that allow the formation of embryoid-like bodies. In another specific embodiment, the isolated placental cells are isolated away from placental cells that are not the isolated placental cells. In another specific embodiment, the isolated placental cells are isolated away from placental cells that do not display these markers.

In another embodiment, a cell population useful in the methods of treatment described herein is a population of cells comprising, e.g., that is enriched for, isolated CD73⁺, CD105⁺, CD200⁺ placental cells. In various embodiments, at least about 10%, at least about 20%, at least about 30%, at least about 40%, at least about 50%, or at least about 60% of cells in said cell population are isolated CD73⁺, CD105⁺, CD200⁺ placental cells. In another embodiment, at least about 70% of said cells in said population of cells are isolated CD73⁺, CD105⁺, CD200⁺ placental cells. In another embodiment, at least about 90%, 95% or 99% of cells in said population of cells are isolated CD73⁺, CD105⁺, CD200⁺ placental cells. In a specific embodiment of said populations, the isolated placental cells are HLA-G⁺. In another specific embodiment, the isolated placental cells are additionally CD34⁻, CD38⁻ or CD45⁻. In another specific embodiment, the isolated placental cells are additionally CD34⁻, CD38⁻ and CD45⁻. In a more specific embodiment, the isolated placental cells are additionally CD34⁻, CD38⁻, CD45⁻, and HLA-G⁺. In another specific embodiment, said population of cells produces one or more embryoid-like bodies when cultured under conditions that allow the formation of embryoid-like bodies. In another specific embodiment, said population of placental cells is isolated away from placental cells that are not stem cells. In another specific embodiment, said population of placental stem cells is isolated away from placental cells that do not display these characteristics.

In certain other embodiments, the isolated placental cells are one or more of CD10⁺, CD29⁺, CD34⁻, CD38⁻, CD44⁺, CD45⁻, CD54⁺, CD90⁺, SH2⁺, SH3⁺, SH4⁺, SSEA3⁻, SSEA4⁻, OCT-4⁺, HLA-G⁺ or ABC-p⁺. In a specific embodiment, the isolated placental cells are CD10⁺, CD29⁺, CD34⁻, CD38⁻, CD44⁺, CD45⁻, CD54⁺, CD90⁺, SH2⁺, SH3⁺, SH4⁺, SSEA3⁻, SSEA4⁻, and OCT-4⁺. In another specific embodiment, the isolated placental cells are CD10⁺, CD29⁺, CD34⁻, CD38⁻, CD45⁻, CD54⁺, SH2⁺, SH3⁺, and SH4⁺. In another specific embodiment, the isolated placental cells are CD10⁺, CD29⁺, CD34⁻, CD38⁻, CD45⁻, CD54⁺, SH2⁺, SH3⁺, SH4⁺ and OCT-4⁺. In another specific embodiment, the isolated placental cells are CD10⁺, CD29⁺, CD34⁻, CD38⁻, CD44⁺, CD45⁻, CD54⁺, CD90⁺, HLA-G⁺, SH2⁺, SH3⁺, SH4⁺. In another specific embodiment, the isolated placental cells are OCT-4⁺ and ABC-p⁺. In another specific embodiment, the isolated placental cells are SH2⁺, SH3⁺, SH4⁺ and OCT-4⁺. In another embodiment, the isolated placental cells are OCT-4⁺, CD34⁻, SSEA3⁻, and SSEA4⁻. In a specific embodiment, said isolated OCT-4⁺, CD34⁻, SSEA3⁻, and SSEA4⁻ placental cells are additionally CD10⁺, CD29⁺, CD34⁻, CD44⁺, CD45⁻, CD54⁺, CD90⁺, SH2⁺, SH3⁺, and SH4⁺. In another embodiment, the isolated placental cells are OCT-4⁺ and CD34⁻, and either SH3⁺ or SH4⁺. In another embodiment, the isolated placental cells are CD34⁻ and either CD10⁺, CD29⁺, CD44⁺, CD54⁺, CD90⁺, or OCT-4⁺.

In another embodiment, the isolated placental cells useful in the methods of treatment described herein are CD200⁺ and OCT-4⁺. In a specific embodiment, the isolated placental cells are CD73⁺ and CD105⁺. In another specific embodiment, said isolated placental cells are HLA-G⁺. In another specific embodiment, said isolated CD200⁺, OCT-4⁺ placental cells are CD34⁻, CD38⁻ or CD45. In another specific embodiment, said isolated CD200⁺, OCT-4⁺ placental cells are CD34⁻, CD38⁻ and CD45⁻. In a more specific embodiment, said isolated CD200⁺, OCT-4⁺ placental cells are CD34⁻, CD38⁻, CD45⁻, CD73⁺, CD105⁺ and HLA-G⁺. In another specific embodiment, the isolated CD200⁺, OCT-4⁺ placental cells facilitate the production of one or more embryoid-like bodies by a population of placental cells that comprises the isolated cells, when the population is cultured under conditions that allow the formation of embryoid-like bodies. In another specific embodiment, said isolated CD200⁺, OCT-4⁺ placental cells are isolated away from placental cells that are not stem cells. In another specific embodiment, said isolated CD200⁺, OCT-4⁺ placental cells are isolated away from placental cells that do not display these characteristics.

In another embodiment, a cell population useful in the methods of treatment described herein is a population of cells comprising, e.g., that is enriched for, CD200⁺, OCT-4⁺ placental cells. In various embodiments, at least about 10%, at least about 20%, at least about 30%, at least about 40%, at least about 50%, or at least about 60% of cells in said cell population are isolated CD200⁺, OCT-4⁺ placental cells. In another embodiment, at least about 70% of said cells are said isolated CD200⁺, OCT-4⁺ placental cells. In another embodiment, at least about 80%, 90%, 95%, or 99% of cells in said cell population are said isolated CD200⁺, OCT-4⁺ placental cells. In a specific embodiment of the isolated populations, said isolated CD200⁺, OCT-4⁺ placental cells are additionally CD73⁺ and CD105⁺. In another specific embodiment, said isolated CD200⁺, OCT-4⁺ placental cells are additionally HLA-G⁺. In another specific embodiment, said isolated CD200⁺, OCT-4⁺ placental cells are additionally CD34⁻, CD38⁻ and CD45⁻. In a more specific embodiment, said isolated CD200⁺, OCT-4⁺ placental cells are additionally CD34⁻, CD38⁻, CD45⁻, CD73⁺, CD105⁺ and HLA-G⁺. In another specific embodiment, the cell population produces one or more embryoid-like bodies when cultured under conditions that allow the formation of embryoid-like bodies. In another specific embodiment, said cell population is isolated away from placental cells that are not isolated CD200⁺, OCT-4⁺ placental cells. In another specific embodiment, said cell population is isolated away from placental cells that do not display these markers.

In another embodiment, the isolated placental cells useful in the methods of treatment described herein are CD73⁺, CD105⁺ and HLA-G⁺. In another specific embodiment, the isolated CD73⁺, CD105⁺ and HLA-G⁺ placental cells are additionally CD34⁻, CD38⁻ or CD45⁻. In another specific embodiment, the isolated CD73⁺, CD105⁺, HLA-G⁺ placental cells are additionally CD34⁻, CD38⁻ and CD45⁻. In another specific embodiment, the isolated CD73⁺, CD105⁺, HLA-G⁺ placental cells are additionally OCT-4⁺. In another specific embodiment, the isolated CD73⁺, CD105⁺, HLA-G⁺ placental cells are additionally CD200⁺. In a more specific embodiment, the isolated CD73⁺, CD105⁺, HLA-G⁺ placental cells are additionally CD34⁻, CD38⁻, CD45⁻, OCT-4⁺ and CD200⁺. In another specific embodiment, the isolated CD73⁺, CD105⁺, HLA-G⁺ placental cells facilitate the formation of embryoid-like bodies in a population of placental cells comprising said cells, when the population is cultured under conditions that allow the formation of embryoid-like bodies. In another specific embodiment, said the isolated CD73⁺, CD105⁺, HLA-G⁺ placental cells are isolated away from placental cells that are not the isolated CD73⁺, CD105⁺, HLA-G⁺ placental cells. In another specific embodiment, said the isolated CD73⁺, CD105⁺, HLA-G⁺ placental cells are isolated away from placental cells that do not display these markers.

In another embodiment, a cell population useful in the methods of treatment described herein is a population of cells comprising, e.g., that is enriched for, isolated CD73⁺, CD105⁺ and HLA-G⁺ placental cells. In various embodiments, at least about 10%, at least about 20%, at least about 30%, at least about 40%, at least about 50%, or at least about 60% of cells in said population of cells are isolated CD73⁺, CD105⁺, HLA-G⁺ placental cells. In another embodiment, at least about 70% of cells in said population of cells are isolated CD73⁺, CD105⁺, HLA-G⁺ placental cells. In another embodiment, at least about 90%, 95% or 99% of cells in said population of cells are isolated CD73⁺, CD105⁺, HLA-G⁺ placental cells. In a specific embodiment of the above populations, said isolated CD73⁺, CD105⁺, HLA-G⁺ placental cells are additionally CD34⁻, CD38⁻ or CD45⁻. In another specific embodiment, said isolated CD73⁺, CD105⁺, HLA-G⁺ placental cells are additionally CD34⁻, CD38⁻ and CD45⁻. In another specific embodiment, said isolated CD73⁺, CD105⁺, HLA-G⁺ placental cells are additionally OCT-4⁺. In another specific embodiment, said isolated CD73⁺, CD105⁺, HLA-G⁺ placental cells are additionally CD200⁺. In a more specific embodiment, said isolated CD73⁺, CD105⁺, HLA-G⁺ placental cells are additionally CD34⁻, CD38⁻, CD45⁻, OCT-4⁺ and CD200⁺. In another specific embodiment, said cell population is isolated away from placental cells that are not CD73⁺, CD105⁺, HLA-G⁺ placental cells. In another specific embodiment, said cell population is isolated away from placental cells that do not display these markers.

In another embodiment, the isolated placental cells useful in the methods of treatment described herein are CD73⁺ and CD105⁺ and facilitate the formation of one or more embryoid-like bodies in a population of isolated placental cells comprising said CD73⁺, CD105⁺ cells when said population is cultured under conditions that allow formation of embryoid-like bodies. In another specific embodiment, said isolated CD73⁺, CD105⁺ placental cells are additionally CD34⁻, CD38⁻ or CD45⁻. In another specific embodiment, said isolated CD73⁺, CD105⁺ placental cells are additionally CD34⁻, CD38⁻ and CD45⁻. In another specific embodiment, said isolated CD73⁺, CD105⁺ placental cells are additionally OCT-4⁺. In a more specific embodiment, said isolated CD73⁺, CD105⁺ placental cells are additionally OCT-4⁺, CD34⁻, CD38⁻ and CD45⁻. In another specific embodiment, said isolated CD73⁺, CD105⁺ placental cells are isolated away from placental cells that are not said cells. In another specific embodiment, said isolated CD73⁺, CD105⁺ placental cells are isolated away from placental cells that do not display these characteristics.

In another embodiment, a cell population useful in the methods of treatment described herein is a population of cells comprising, e.g., that is enriched for, isolated placental cells that are CD73⁺, CD105⁺ and facilitate the formation of one or more embryoid-like bodies in a population of isolated placental cells comprising said cells when said population is cultured under conditions that allow formation of embryoid-like bodies. In various embodiments, at least about 10%, at least about 20%, at least about 30%, at least about 40%, at least about 50%, or at least about 60% of cells in said population of cells are said isolated CD73⁺, CD105⁺ placental cells. In another embodiment, at least about 70% of cells in said population of cells are said isolated CD73⁺, CD105⁺ placental cells. In another embodiment, at least about 90%, 95% or 99% of cells in said population of cells are said isolated CD73⁺, CD105⁺ placental cells. In a specific embodiment of the above populations, said isolated CD73⁺, CD105⁺ placental cells are additionally CD34⁻, CD38 or CD45⁻. In another specific embodiment, said isolated CD73⁺, CD105⁺ placental cells are additionally CD34⁻, CD38⁻ and CD45⁻. In another specific embodiment, said isolated CD73⁺, CD105⁺ placental cells are additionally OCT-4⁺. In another specific embodiment, said isolated CD73⁺, CD105⁺ placental cells are additionally CD200⁺. In a more specific embodiment, said isolated CD73⁺, CD105⁺ placental cells are additionally CD34⁻, CD38⁻, CD45⁻, OCT-4⁺ and CD200⁺.

In another specific embodiment, said cell population is isolated away from placental cells that are not said isolated CD73⁺, CD105⁺ placental cells. In another specific embodiment, said cell population is isolated away from placental cells that do not display these markers.

In another embodiment, the isolated placental cells useful in the methods of treatment described herein are OCT-4⁺ and facilitate formation of one or more embryoid-like bodies in a population of isolated placental cells comprising said cells when cultured under conditions that allow formation of embryoid-like bodies. In a specific embodiment, said isolated OCT-4$^+$ placental cells are additionally CD73$^+$ and CD105$^+$. In another specific embodiment, said isolated OCT-4$^+$ placental cells are additionally CD34$^-$, CD38$^-$, or CD45$^-$. In another specific embodiment, said isolated OCT-4$^+$ placental cells are additionally CD200$^+$. In a more specific embodiment, said isolated OCT-4$^+$ placental cells are additionally CD73$^+$, CD105$^+$, CD200$^+$, CD34$^-$, CD38$^-$, and CD45$^-$. In another specific embodiment, said isolated OCT-4$^+$ placental cells are isolated away from placental cells that are not OCT-4$^+$ placental cells. In another specific embodiment, said isolated OCT-4$^+$ placental cells are isolated away from placental cells that do not display these characteristics.

In another embodiment, a cell population useful in the methods of treatment described herein is a population of cells comprising, e.g., that is enriched for, isolated placental cells that are OCT-4$^+$ and facilitate the formation of one or more embryoid-like bodies in a population of isolated placental cells comprising said cells when said population is cultured under conditions that allow formation of embryoid-like bodies. In various embodiments, at least about 10%, at least about 20%, at least about 30%, at least about 40%, at least about 50%, or at least about 60% of cells in said population of cells are said isolated OCT-4$^+$ placental cells. In another embodiment, at least about 70% of cells in said population of cells are said isolated OCT-4$^+$ placental cells. In another embodiment, at least about 80%, 90%, 95% or 99% of cells in said population of cells are said isolated OCT-4$^+$ placental cells. In a specific embodiment of the above populations, said isolated OCT-4$^+$ placental cells are additionally CD34$^-$, CD38$^-$ or CD45$^-$. In another specific embodiment, said isolated OCT-4$^+$ placental cells are additionally CD34$^-$, CD38$^-$ and CD45$^-$. In another specific embodiment, said isolated OCT-4$^+$ placental cells are additionally CD73$^+$ and CD105$^+$. In another specific embodiment, said isolated OCT-4$^+$ placental cells are additionally CD200$^+$. In a more specific embodiment, said isolated OCT-4$^+$ placental cells are additionally CD73$^+$, CD105$^+$, CD200$^+$, CD34$^-$, CD38$^-$, and CD45$^-$. In another specific embodiment, said cell population is isolated away from placental cells that are not said cells. In another specific embodiment, said cell population is isolated away from placental cells that do not display these markers.

In another embodiment, the isolated placental cells useful in the methods of treatment described herein are isolated HLA-A,B,C$^-$,CD45$^-$, CD133$^-$ and CD34$^-$ placental cells. In another embodiment, a cell population useful for the treatment of disruption of blood flow in or around the brain or CNS is a population of cells comprising isolated placental cells, wherein at least about 70%, at least about 80%, at least about 90%, at least about 95% or at least about 99% of cells in said isolated population of cells are isolated HLA-A,B,C$^-$, CD45$^-$, CD133$^-$ and CD34$^-$ placental cells. In a specific embodiment, said isolated placental cell or population of isolated placental cells is isolated away from placental cells that are not HLA-A,B,C$^-$, CD45$^-$, CD133$^-$ and CD34$^-$ placental cells. In another specific embodiment, said isolated placental cells are non-maternal in origin. In another specific embodiment, said isolated population of placental cells are substantially free of maternal components; e.g., at least about 40%, 45%, 5-0%, 55%, 60%, 65%, 70%, 75%, 90%, 85%, 90%, 95%, 98% or 99% of said cells in said isolated population of placental cells are non-maternal in origin.

In another embodiment, the isolated placental cells useful in the methods of treatment described herein are isolated CD10$^+$, CD13$^+$, CD33$^+$, CD45, CD117$^-$ and CD133$^-$ placental cells. In another embodiment, a cell population useful for the treatment of disruption of blood flow in or around the brain or CNS is a population of cells comprising isolated placental cells, wherein at least about 70%, at least about 80%, at least about 90%, at least about 95% or at least about 99% of cells in said population of cells are isolated CD10$^+$, CD13$^+$,CD33$^+$,CD45$^-$,CD117$^-$ and CD133$^-$ placental cells. In a specific embodiment, said isolated placental cells or population of isolated placental cells is isolated away from placental cells that are not said isolated placental cells. In another specific embodiment, said isolated CD10$^+$, CD13$^+$, CD33$^+$, CD45$^-$, CD117$^-$ and CD133$^-$ placental cells are non-maternal in origin, i.e., have the fetal genotype. In another specific embodiment, at least about 40%, 45%, 50%, 55%, 60%, 65%, 70%, 75%, 90%, 85%, 90%, 95%, 98% or 99% of said cells in said isolated population of placental cells, are non-maternal in origin. In another specific embodiment, said isolated placental cells or population of isolated placental cells are isolated away from placental cells that do not display these characteristics.

In another embodiment, the isolated placental cells useful in the methods of treatment described herein are isolated CD10$^-$, CD33$^-$, CD44$^+$, CD45$^-$, and CD117$^-$ placental cells. In another embodiment, a cell population useful for the treatment of disruption of blood flow in or around the brain or CNS is a population of cells comprising, e.g., enriched for, isolated placental cells, wherein at least about 70%, at least about 80%, at least about 90%, at least about 95% or at least about 99% of cells in said population of cells are isolated CD10$^-$, CD33$^-$, CD44$^+$, CD45$^-$, and CD117$^-$ placental cells. In a specific embodiment, said isolated placental cell or population of isolated placental cells is isolated away from placental cells that are not said cells. In another specific embodiment, said isolated placental cells are non-maternal in origin. In another specific embodiment, at least about 40%, 45%, 50%, 55%, 60%, 65%, 70%, 75%, 90%, 85%, 90%, 95%, 98% or 99% of said cells in said cell population are non-maternal in origin. In another specific embodiment, said isolated placental cell or population of isolated placental cells is isolated away from placental cells that do not display these markers.

In another embodiment, the isolated placental cells useful in the methods of treatment described herein are isolated CD10$^-$, CD13$^-$, CD33$^-$, CD45$^-$, and CD117$^-$ placental cells. In another embodiment, a cell population useful for the treatment of disruption of blood flow in or around the brain or CNS is a population of cells comprising, e.g., enriched for, isolated CD10$^-$,CD13$^-$, CD33$^-$, CD45$^-$, and CD117$^-$ placental cells, wherein at least about 70%, at least about 80%, at least about 90%, at least about 95% or at least about 99% of cells in said population are CD10$^-$, CD13$^-$, CD33$^-$, CD45$^-$, and CD117 placental cells. In a specific embodiment, said isolated placental cells or population of isolated placental cells are isolated away from placental cells that are not said cells. In another specific embodiment, said isolated placental cells are non-maternal in origin. In another specific embodiment, at least about 40%, 45%, 50%, 55%, 60%, 65%, 70%, 75%, 90%, 85%, 90%, 95%, 98% or 99% of said cells in said cell population are non-maternal in origin. In another specific embodiment, said isolated placental cells or population of isolated placental cells is isolated away from placental cells that do not display these characteristics.

In another embodiment, the isolated placental cells useful in the methods of treatment described herein are HLA A,B, C$^+$, CD45$^-$, CD34$^-$, and CD133$^-$, and are additionally CD10$^+$, CD13$^+$, CD38$^+$, CD44$^+$, CD90$^+$, CD105$^+$, CD200$^+$ and/or HLA-G$^+$, and/or negative for CD117. In another embodiment, a cell population useful for the treatment of disruption of blood flow in or around the brain or CNS is a population of cells comprising isolated placental cells, wherein at least about 20%, 25%, 30%, 35%, 40%, 45%, 50%, 55%, 60%, 65%, 70%, 75%, 80%, 85%, 90%, 95%, 98% or about 99% of the cells in said population are isolated placental cells that are HLA A,B,C$^-$, CD45$^-$, CD34$^-$, CD133$^-$, and that are additionally positive for CD10, CD13, CD38, CD44, CD90, CD105, CD200 and/or HLA-G, and/or negative for CD117. In a specific embodiment, said isolated placental cells or population of isolated placental cells are isolated away from placental cells that are not said cells. In another specific embodiment, said isolated placental cells are non-maternal in origin. In another specific embodiment, at least about 40%, 45%, 50%, 55%, 60%, 65%, 70%, 75%, 90%, 85%, 90%, 95%, 98% or 99% of said cells in said cell population are non-maternal in origin. In another specific embodiment, said isolated placental cells or population of isolated placental cells are isolated away from placental cells that do not display these markers.

In another embodiment, the isolated placental cells useful in the methods of treatment described herein are isolated placental cells that are CD200$^+$ and CD10$^+$, as determined by antibody binding, and CD117$^-$, as determined by both antibody binding and RT-PCR. In another embodiment, the isolated placental cells useful in the treatment of disruption of blood flow in or around the brain or CNS are isolated placental cells, e.g., placental stem cells or placental multipotent cells, that are CD10$^+$, CD29$^-$, CD54$^+$, CD200$^+$, HLA-G$^+$, HLA class I$^-$ and β-2-microglobulin$^-$. In another embodiment, isolated placental cells useful in the treatment of disruption of blood flow in or around the brain or CNS are placental cells wherein the expression of at least one cellular marker is at least two-fold higher than for a mesenchymal stem cell (e.g., a bone marrow-derived mesenchymal stem cell). In another specific embodiment, said isolated placental cells are non-maternal in origin. In another specific embodiment, at least about 40%, 45%, 50%, 55%, 60%, 65%, 70%, 75%, 90%, 85%, 90%, 95%, 98% or 99% of said cells in said cell population are non-maternal in origin.

In another embodiment, the isolated placental cells useful in the methods of treatment described herein are isolated placental cells, e.g., placental stem cells or placental multipotent cells, that are one or more of CD10$^+$, CD29$^+$, CD44$^+$, CD45$^-$, CD54/ICAM$^+$, CD62E$^-$, CD62L$^-$, CD62P$^-$, CD80$^-$, CD86$^-$, CD103$^-$, CD104$^-$, CD105$^+$, CD106/VCAM$^+$, CD144/VE-cadherin$^{low}$, CD184/CXCR4$^-$, β2-microglobulin$^{low}$, MHC-I$^{low}$, MHC-II$^-$, HLA-G$^{low}$, and/or PDL1$^{low}$. In a specific embodiment, the isolated placental cells are at least CD29$^+$ and CD54$^+$. In another specific embodiment, the isolated placental cells are at least CD44$^+$ and CD106$^+$. In another specific embodiment, the isolated placental cells are at least CD29$^+$.

In another embodiment, a cell population useful in the methods of treatment described herein comprises isolated placental cells, and at least 50%, 60%, 70%, 80%, 90%, 95%, 98% or 99% of the cells in said cell population are isolated placental cells that are one or more of CD10$^+$, CD29$^+$, CD44$^+$, CD45$^-$, CD54/ICAM$^+$, CD62-E$^-$, CD62-L$^-$, CD62-P$^-$, CD80$^-$, CD86$^-$, CD103$^-$, CD104$^-$, CD105$^+$, CD106/VCAM$^+$, CD144/VE-cadherin$^{low}$, CD184/CXCR4$^-$, β2-microglobulin$^{low}$, HLA-I$^{low}$, HLA-II$^-$, HLA-G$^{low}$, and/or PDL1$^{low}$. In a more specific embodiment, at least 50%, 60%, 70%, 80%, 90%, 95%, 98% or 99% of cells in said cell population are CD10$^+$, CD29$^+$, CD44$^+$, CD45$^-$, CD54/ICAM$^+$, CD62-E$^-$, CD62-L$^-$, CD62-P$^-$, CD80$^-$, CD86$^-$, CD103$^-$, CD104$^-$, CD105$^+$, CD106/VCAM$^+$, CD144/VE-cadherin$^{low}$, CD184/CXCR4$^-$, β2-microglobulin$^{low}$, MHC-I$^{low}$, MHC-II$^-$, HLA-G$^{low}$, and PDL1$^{low}$.

In another embodiment, the isolated placental cells useful in the treatment of disruption of blood flow in or around the brain or CNS are isolated placental cells that are one or more, or all, of CD10$^+$, CD29$^+$, CD34$^-$, CD38$^-$, CD44$^+$, CD45$^-$, CD54$^+$, CD90$^+$, SH2$^+$, SH3$^+$, SH4$^+$, SSEA3$^-$, SSEA4$^-$, OCT-4$^+$, and ABC-p$^+$, where ABC-p is a placenta-specific ABC transporter protein (also known as breast cancer resistance protein (BCRP) and as mitoxantrone resistance protein (MXR)), wherein said isolated placental cells are obtained by perfusion of a mammalian, e.g., human, placenta that has been drained of cord blood and perfused to remove residual blood.

Gene profiling confirms that isolated placental cells, and populations of isolated placental cells, are distinguishable from other cells, e.g., mesenchymal stem cells, e.g., bone marrow-derived mesenchymal stem cells. The isolated placental cells described herein can be distinguished from, e.g., mesenchymal stem cells on the basis of the expression of one or more genes, the expression of which is significantly higher in the isolated placental cells, or in certain isolated umbilical cord stem cells, in comparison to bone marrow-derived mesenchymal stem cells. In particular, the isolated placental cells, useful in the methods of treatment provided herein, can be distinguished from mesenchymal stem cells on the basis of the expression of one or more genes, the expression of which is significantly higher (that is, at least twofold higher) in the isolated placental cells than in an equivalent number of bone marrow-derived mesenchymal stem cells, wherein the one or more genes are ACTG2, ADARB1, AMIGO2, ARTS-1, B4GALT6, BCHE, C11orf9, CD200, COL4A1, COL4A2, CPA4, DMD, DSC3, DSG2, ELOVL2, F2 RL1, FLJ10781, GATA6, GPR126, GPRC5B, HLA-G, ICAM1, IER3, IGFBP7, IL1A, IL6, IL18, KRT18, KRT8, LIPG, LRAP, MATN2, MEST, NFE2L3, NUAK1, PCDH7, PDLIM3, PKP2, RTN1, SERPINB9, ST3GAL6, ST6GALNAC5, SLC12A8, TCF21, TGFB2, VTN, ZC3H12A, or a combination of any of the foregoing, when the cells are grown under equivalent conditions. See, e.g., U.S. Patent Application Publication No. 2007/0275362, the disclosure of which is incorporated herein by reference in its entirety. In a more specific embodiment, said isolated placental cells express said one or more genes when cultured for from about 3 to about 35 population doublings in a medium comprising DMEM-LG (e.g., from Gibco); 2% fetal calf serum (e.g., from Hyclone Labs.); 1× insulin-transferrin-selenium (ITS); 1× linoleic acid-bovine serum albumin (LA-BSA); 10$^{-9}$ M dexamethasone (e.g., from Sigma); 10$^{-4}$ M ascorbic acid 2-phosphate (e.g., from Sigma); epidermal growth factor 10 ng/mL (e.g., from R&D Systems); and platelet-derived growth factor (PDGF-BB) 10 ng/mL (e.g., from R&D Systems). In a specific embodiment, the isolated placental cell-specific or isolated umbilical cord cell-specific gene is CD200.

Specific sequences for these genes can be found in GenBank at accession nos. NM_001615 (ACTG2), BC065545 (ADARB1), (NM_181847 (AMIGO2), AY358590 (ARTS-1), BC074884 (B4GALT6), BC008396 (BCHE), BC020196 (C11orf9), BC031103 (CD200), NM_001845 (COL4 A1), NM_001846 (COL4A2), BC052289 (CPA4), BC094758 (DMD), AF293359 (DSC3), NM_001943 (DSG2), AF338241 (ELOVL2), AY336105 (F2RL1), NM_018215 (FLJ10781), AY416799 (GATA6), BC075798 (GPR126), NM_016235 (GPRC5B), AF340038 (ICAM1), BC000844 (IER3), BC066339 (IGFBP7), BC013142 (IL1A), BT019749 (IL6), BC007461 (IL18), (BC072017) KRT18, BC075839 (KRT8), BC060825 (LIPG), BC065240 (LRAP), BC010444 (MATN2), BC011908 (MEST), BC068455 (NFE2L3), NM_014840 (NUAK1), AB006755 (PCDH7), NM_014476 (PDLIM3), BC126199 (PKP-2), BC090862 (RTN1), BC002538 (SERPINB9), BC023312 (ST3GAL6), BC001201 (ST6GALNAC5), BC126160 or BC065328 (SLC12A8), BC025697 (TCF21), BC096235 (TGFB2), BC005046 (VTN), and BC005001 (ZC3H12A) as of March 2008.

In a more specific embodiment, said isolated placental cells express each of ACTG2, ADARB1, AMIGO2, ARTS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, HLA-G, ICAM1, IER3, IGFBP7, IL1A, IL6, IL18, KRT18, KRT8, LIPG, LRAP, MATN2, MEST, NFE2L3, NUAK1, PCDH7, PDLIM3, PKP2, RTN1, SERPINB9, ST3GAL6, ST6GALNAC5, SLC12A8, TCF21, TGFB2, VTN, and ZC3H12A at a detectably higher level than an equivalent number of bone marrow-derived mesenchymal stem cells, when the cells are grown under equivalent conditions.

Expression of the above-referenced genes can be assessed by standard techniques. For example, probes based on the sequence of the gene(s) can be individually selected and constructed by conventional techniques. Expression of the genes can be assessed, e.g., on a microarray comprising probes to one or more of the genes, e.g., an Affymetrix GENECHIP® Human Genome U133A 2.0 array, or an Affymetrix GENECHIP® Human Genome U133 Plus 2.0 (Santa Clara, Calif.). Expression of these genes can be assessed even if the sequence for a particular GenBank accession number is amended because probes specific for the amended sequence can readily be generated using well-known standard techniques.

The level of expression of these genes can be used to confirm the identity of a population of isolated placental cells, to identify a population of cells as comprising at least a plurality of isolated placental cells, or the like. Populations of isolated placental cells, the identity of which is confirmed, can be clonal, e.g., populations of isolated placental cells expanded from a single isolated placental cell, or a mixed population of stem cells, e.g., a population of cells comprising solely isolated placental cells that are expanded from multiple isolated placental cells, or a population of cells comprising isolated placental cells, as described herein, and at least one other type of cell.

The level of expression of these genes can be used to select populations of isolated placental cells. For example, a population of cells, e.g., clonally-expanded cells, may be selected if the expression of one or more of the genes listed above is significantly higher in a sample from the population of cells than in an equivalent population of mesenchymal stem cells. Such selecting can be of a population from a plurality of isolated placental cell populations, from a plurality of cell populations, the identity of which is not known, etc.

Isolated placental cells can be selected on the basis of the level of expression of one or more such genes as compared to the level of expression in said one or more genes in, e.g., a mesenchymal stem cell control, for example, the level of expression in said one or more genes in an equivalent number of bone marrow-derived mesenchymal stem cells. In one embodiment, the level of expression of said one or more genes in a sample comprising an equivalent number of mesenchymal stem cells is used as a control. In another embodiment, the control, for isolated placental cells tested under certain conditions, is a numeric value representing the level of expression of said one or more genes in mesenchymal stem cells under said conditions.

The isolated placental cells described herein display the above characteristics (e.g., combinations of cell surface markers and/or gene expression profiles) in primary culture, or during proliferation in medium comprising, e.g., DMEM-LG (Gibco), 2% fetal calf serum (FCS) (Hyclone Laboratories), 1× insulin-transferrin-selenium (ITS), 1× lenolenic-acid-bovine-serum-albumin (LA-BSA), $10^{-9}$ M dexamethasone (Sigma), $10^{-4}$M ascorbic acid 2-phosphate (Sigma), epidermal growth factor (EGF) 10 ng/ml (R&D Systems), platelet derived-growth factor (PDGF-BB) 10 ng/ml (R&D Systems), and 100 U penicillin/1000 U streptomycin.

In another specific embodiment of said isolated placental cells or populations of cells comprising the isolated placental cells, said cells or population have been expanded, for example, passaged at least, about, or no more than, 1, 2, 3, 4, 5, 6, 7, 8, 9, 10, 11, 12, 13, 14, 15, 16, 17, 18, 19, or 20 times, or proliferated for at least, about, or no more than, 1, 2, 3, 4, 5, 6, 7, 8, 9, 10, 12, 14, 16, 18, 20, 22, 24, 26, 28, 30, 32, 34, 36, 38 or 40 population doublings. In another specific embodiment of the isolated placental cells, or populations of cells comprising isolated placental cells, that are disclosed herein, said isolated placental cells are fetal in origin (that is, have the fetal genotype).

In certain embodiments of isolated placental cells, said isolated placental cells do not differentiate during culturing in growth medium, i.e., medium formulated to promote proliferation, e.g., during proliferation in growth medium. In another specific embodiment, said isolated placental cells do not require a feeder layer in order to proliferate. In another specific embodiment, said isolated placental cells do not differentiate in culture in the absence of a feeder layer, solely because of the lack of a feeder cell layer.

In another embodiment, cells useful in the treatment of disruption of blood flow in or around the brain or CNS are isolated placental cells, wherein a plurality of said isolated placental cells are positive for aldehyde dehydrogenase (ALDH), as assessed by an aldehyde dehydrogenase activity assay. Such assays are known in the art (see, e.g., Bostian and Betts, *Biochem. J.*, 173, 787, (1978)). In a specific embodiment, said ALDH assay uses ALDEFLUOR® (Aldagen, Inc., Ashland, Oreg.) as a marker of aldehyde dehydrogenase activity. In a specific embodiment, said plurality is between about 3% and about 25% of cells in said population of cells. In another embodiment, provided herein is a population of isolated umbilical cord cells, e.g., multipotent isolated umbilical cord cells, wherein a plurality of said isolated umbilical cord cells are positive for aldehyde dehydrogenase, as assessed by an aldehyde dehydrogenase activity assay that uses ALDEFLUOR® as an indicator of aldehyde dehydrogenase activity. In a specific embodiment, said plurality is between about 3% and about 25% of cells in said population of cells. In another embodiment, said population of isolated placental cells or isolated umbilical cord cells shows at least three-fold, or at least five-fold, higher ALDH activity than a population of bone marrow-derived mesenchymal stem cells having about the same number of cells and cultured under the same conditions.

In certain embodiments of any of the populations of cells comprising the isolated placental cells described herein, the placental cells in said populations of cells are substantially free of cells having a maternal genotype; e.g., at least 40%, 45%, 50%, 55%, 60%, 65%, 70%, 75%, 80%, 85%, 90%, 95%, 98% or 99% of the placental cells in said population have a fetal genotype. In certain other embodiments of any of the populations of cells comprising the isolated placental cells described herein, the populations of cells comprising said placental cells are substantially free of cells having a maternal genotype; e.g., at least 40%, 45%, 50%, 55%, 60%, 65%, 70%, 75%, 80%, 85%, 90%, 95%, 98% or 99% of the cells in said population have a fetal genotype.

In a specific embodiment of any of the above isolated placental cells or cell populations of isolated placental cells, the karyotype of the cells, or at least about 95% or about 99% of the cells in said population, is normal. In another specific embodiment of any of the above placental cells or cell populations, the cells, or cells in the population of cells, are non-maternal in origin.

Isolated placental cells, or populations of isolated placental cells, bearing any of the above combinations of markers, can be combined in any ratio. Any two or more of the above isolated placental cell populations can be combined to form an isolated placental cell population. For example, an population of isolated placental cells can comprise a first population of isolated placental cells defined by one of the marker combinations described above, and a second population of isolated placental cells defined by another of the marker combinations described above, wherein said first and second populations are combined in a ratio of about 1:99, 2:98, 3:97, 4:96, 5:95, 10:90, 20:80, 30:70, 40:60, 50:50, 60:40, 70:30, 80:20, 90:10, 95:5, 96:4, 97:3, 98:2, or about 99:1. In like fashion, any three, four, five or more of the above-described isolated placental cells or isolated placental cells populations can be combined.

Isolated placental cells useful for the treatment of disruption of blood flow in or around the brain or CNS can be obtained, e.g., by disruption of placental tissue, with or without enzymatic digestion (see Section 5.5.3) or perfusion (see Section 5.5.4). For example, populations of isolated placental cells can be produced according to a method comprising perfusing a mammalian placenta that has been drained of cord blood and perfused to remove residual blood; perfusing said placenta with a perfusion solution; and collecting said perfusion solution, wherein said perfusion solution after perfusion comprises a population of placental cells that comprises isolated placental cells; and isolating a plurality of said isolated placental cells from said population of cells. In a specific embodiment, the perfusion solution is passed through both the umbilical vein and umbilical arteries and collected after it exudes from the placenta. In another specific embodiment, the perfusion solution is passed through the umbilical vein and collected from the umbilical arteries, or passed through the umbilical arteries and collected from the umbilical vein In various embodiments, the isolated placental cells, contained within a population of cells obtained from perfusion of a placenta, are at least 50%, 60%, 70%, 80%, 90%, 95%, 99% or at least 99.5% of said population of placental cells. In another specific embodiment, the isolated placental cells collected by perfusion comprise fetal and maternal cells. In another specific embodiment, the isolated placental cells collected by perfusion are at least 50%, 60%, 70%, 80%, 90%, 95%, 99% or at least 99.5% fetal cells.

In another specific embodiment, provided herein is a composition comprising a population of the isolated placental cells, as described herein, collected by perfusion, wherein said composition comprises at least a portion of the perfusion solution used to collect the isolated placental cells.

Isolated populations of the isolated placental cells described herein can be produced by digesting placental tissue with a tissue-disrupting enzyme to obtain a population of placental cells comprising the cells, and isolating, or substantially isolating, a plurality of the placental cells from the remainder of said placental cells. The whole, or any part of, the placenta can be digested to obtain the isolated placental cells described herein. In specific embodiments, for example, said placental tissue can be a whole placenta, an amniotic membrane, chorion, a combination of amnion and chorion, or a combination of any of the foregoing. In other specific embodiment, the tissue-disrupting enzyme is trypsin or collagenase. In various embodiments, the isolated placental cells, contained within a population of cells obtained from digesting a placenta, are at least 50%, 60%, 70%, 80%, 90%, 95%, 99% or at least 99.5% of said population of placental cells.

The isolated populations of placental cells described above, and populations of isolated placental cells generally, can comprise about, at least, or no more than, $1 \times 10^5$, $5 \times 10^5$, $1 \times 10^6$, $5 \times 10^6$, $1 \times 10^7$, $5 \times 10^7$, $1 \times 10^8$, $5 \times 10^8$, $1 \times 10^9$, $5 \times 10^9$, $1 \times 10^{10}$, $5 \times 10^{10}$, $1 \times 10^{11}$ or more of the isolated placental cells. Populations of isolated placental cells useful in the methods of treatment described herein comprise at least 50%, 55%, 60%, 65%, 70%, 75%, 80%, 85%, 90%, 95%, 98%, or 99% viable isolated placental cells, as determined by, e.g., trypan blue exclusion

5.4.3 Growth in Culture

The growth of the isolated placental cells described herein in Section 5.4.2, as for any mammalian cell, depends in part upon the particular medium selected for growth. Under optimum conditions, the isolated placental cells typically double in number in about 1 day. During culture, the isolated placental cells described herein adhere to a substrate in culture, e.g. the surface of a tissue culture container (e.g., tissue culture dish plastic, fibronectin-coated plastic, and the like) and form a monolayer.

Populations of placental cells that comprise the isolated placental cells described herein, when cultured under appropriate conditions, can form embryoid-like bodies, that is, three-dimensional clusters of cells grow atop the adherent cell layer. Cells within the embryoid-like bodies express markers associated with very early stem cells, e.g., OCT-4, Nanog, SSEA3 and SSEA4. Cells within the embryoid-like bodies are typically not adherent to the culture substrate, as are the isolated placental cells described herein, but remain attached to the adherent cells during culture. Embryoid-like body cells are dependent upon the adherent isolated placental cells for viability, as embryoid-like bodies do not form in the absence of the adherent isolated placental cells. The adherent isolated placental cells thus facilitate the growth of one or more embryoid-like bodies in a population of placental cells that comprise the adherent isolated placental cells. Without wishing to be bound by theory, the cells of the embryoid-like bodies are thought to grow on the adherent isolated placental cells much as embryonic stem cells grow on a feeder layer of cells.

5.5 Methods of Obtaining Isolated Placental Cells

5.5.1 Stem Cell Collection Composition

Further provided herein are methods of collecting and isolating placental cells, e.g., the isolated placental cells described in Section 5.4.2, above. Generally, such cells are obtained from a mammalian placenta using a physiologically-acceptable solution, e.g., a cell collection composition. An exemplary cell collection composition is described in detail in related U.S. Patent Application Publication No. 2007/0190042, entitled "Improved Medium for Collecting Placental Stem Cells and Preserving Organs," the disclosure of which is incorporated herein by reference in its entirety The cell collection composition can comprise any physiologically-acceptable solution suitable for the collection and/or culture of cells, e.g., the isolated placental cells described herein, for example, a saline solution (e.g., phosphate-buffered saline, Kreb's solution, modified Kreb's solution, Eagle's solution, 0.9% NaCl. etc.), a culture medium (e.g., DMEM, H.DMEM, etc.), and the like.

The cell collection composition can comprise one or more components that tend to preserve isolated placental cells, that is, prevent the isolated placental cells from dying, or delay the death of the isolated placental cells, reduce the number of isolated placental cells in a population of cells that die, or the like, from the time of collection to the time of culturing. Such components can be, e.g., an apoptosis inhibitor (e.g., a caspase inhibitor or JNK inhibitor); a vasodilator (e.g., magnesium sulfate, an antihypertensive drug, atrial natriuretic peptide (ANP), adrenocorticotropin, corticotropin-releasing hormone, sodium nitroprusside, hydralazine, adenosine triphosphate, adenosine, indomethacin or magnesium sulfate, a phosphodiesterase inhibitor, etc.); a necrosis inhibitor (e.g., 2-(1H-Indol-3-yl)-3-pentylamino-maleimide, pyrrolidine dithiocarbamate, or clonazepam); a TNF-α inhibitor; and/or an oxygen-carrying perfluorocarbon (e.g., perfluorooctyl bromide, perfluorodecyl bromide, etc.).

The cell collection composition can comprise one or more tissue-degrading enzymes, e.g., a metalloprotease, a serine protease, a neutral protease, an RNase, or a DNase, or the like. Such enzymes include, but are not limited to, collagenases (e.g., collagenase I, II, III or IV, a collagenase from *Clostridium histolyticum*, etc.); dispase, thermolysin, elastase, trypsin, LIBERASE, hyaluronidase, and the like.

The cell collection composition can comprise a bacteriocidally or bacteriostatically effective amount of an antibiotic. In certain non-limiting embodiments, the antibiotic is a macrolide (e.g., tobramycin), a cephalosporin (e.g., cephalexin, cephradine, cefuroxime, cefprozil, cefaclor, cefixime or cefadroxil), a clarithromycin, an erythromycin, a penicillin (e.g., penicillin V) or a quinolone (e.g., ofloxacin, ciprofloxacin or norfloxacin), a tetracycline, a streptomycin, etc. In a particular embodiment, the antibiotic is active against Gram (+) and/or Gram(−) bacteria, e.g., *Pseudomonas aeruginosa, Staphylococcus aureus*, and the like. In one embodiment, the antibiotic is gentamycin, e.g., about 0.005% to about 0.01% (w/v) in culture medium The cell collection composition can also comprise one or more of the following compounds: adenosine (about 1 mM to about 50 mM); D-glucose (about 20 mM to about 100 mM); magnesium ions (about 1 mM to about 50 mM); a macromolecule of molecular weight greater than 20,000 daltons, in one embodiment, present in an amount sufficient to maintain endothelial integrity and cellular viability (e.g., a synthetic or naturally occurring colloid, a polysaccharide such as dextran or a polyethylene glycol present at about 25 g/l to about 100 g/l, or about 40 g/l to about 60 g/l); an antioxidant (e.g., butylated hydroxyanisole, butylated hydroxytoluene, glutathione, vitamin C or vitamin E present at about 25 µM to about 100 µM); a reducing agent (e.g., N-acetylcysteine present at about 0.1 mM to about 5 mM); an agent that prevents calcium entry into cells (e.g., verapamil present at about 2 µM to about 25 µM); nitroglycerin (e.g., about 0.05 g/L to about 0.2 g/L); an anticoagulant, in one embodiment, present in an amount sufficient to help prevent clotting of residual blood (e.g., heparin or hirudin present at a concentration of about 1000 units/l to about 100,000 units/l); or an amiloride containing compound (e.g., amiloride, ethyl isopropyl amiloride, hexamethylene amiloride, dimethyl amiloride or isobutyl amiloride present at about 1.0 µM to about 5 µM).

5.5.2 Collection and Handling of Placenta

Generally, a human placenta is recovered shortly after its expulsion after birth. In a preferred embodiment, the placenta is recovered from a patient after informed consent and after a complete medical history of the patient is taken and is associated with the placenta. Preferably, the medical history continues after delivery. Such a medical history can be used to coordinate subsequent use of the placenta or the isolated placental cells harvested therefrom. For example, isolated human placental cells can be used, in light of the medical history, for personalized medicine for the infant associated with the placenta, or for parents, siblings or other relatives of the infant.

Prior to recovery of isolated placental cells, the umbilical cord blood and placental blood are preferably removed. In certain embodiments, after delivery, the cord blood in the placenta is recovered. The placenta can be subjected to a conventional cord blood recovery process. Typically a needle or cannula is used, with the aid of gravity, to exsanguinate the placenta (see, e.g., Anderson, U.S. Pat. No. 5,372,581; Hessel et al., U.S. Pat. No. 5,415,665). The needle or cannula is usually placed in the umbilical vein and the placenta can be gently massaged to aid in draining cord blood from the placenta. Such cord blood recovery may be performed commercially, e.g., LifeBank USA, Cedar Knolls, N.J. Preferably, the placenta is gravity drained without further manipulation so as to minimize tissue disruption during cord blood recovery.

Typically, a placenta is transported from the delivery or birthing room to another location, e.g., a laboratory, for recovery of cord blood and collection of stem cells by, e.g., perfusion or tissue dissociation. The placenta is preferably transported in a sterile, thermally insulated transport device (maintaining the temperature of the placenta between 20-28° C.), for example, by placing the placenta, with clamped proximal umbilical cord, in a sterile zip-lock plastic bag, which is then placed in an insulated container. In another embodiment, the placenta is transported in a cord blood collection kit substantially as described in pending U.S. Pat. No. 7,147,626, the disclosure of which is incorporated by reference herein. Preferably, the placenta is delivered to the laboratory four to twenty-four hours following delivery. In certain embodiments, the proximal umbilical cord is clamped, preferably within 4-5 cm (centimeter) of the insertion into the placental disc prior to cord blood recovery. In other embodiments, the proximal umbilical cord is clamped after cord blood recovery but prior to further processing of the placenta.

The placenta, prior to cell collection, can be stored under sterile conditions and at either room temperature or at a temperature of 5° C. to 25° C. The placenta may be stored for a period of for a period of four to twenty-four hours, up to forty-eight hours, or longer than forty eight hours, prior to perfusing the placenta to remove any residual cord blood. In one embodiment, the placenta is harvested from between about zero hours to about two hours post-expulsion. The placenta is preferably stored in an anticoagulant solution at a temperature of 5° C. to 25° C. Suitable anticoagulant solutions are well known in the art. For example, a solution of heparin or warfarin sodium can be used. In a preferred embodiment, the anticoagulant solution comprises a solution of heparin (e.g., 1% w/w in 1:1000 solution). The exsanguinated placenta is preferably stored for no more than 36 hours before placental cells are collected.

The mammalian placenta or a part thereof, once collected and prepared generally as above, can be treated in any art-known manner, e.g., can be perfused or disrupted, e.g., digested with one or more tissue-disrupting enzymes, to obtain isolated placental cells.

5.5.3 Physical Disruption and Enzymatic Digestion of Placental Tissue

In one embodiment, stem cells are collected from a mammalian placenta by physical disruption of part of all of the organ. For example, the placenta, or a portion thereof, may be, e.g., crushed, sheared, minced, diced, chopped, macerated or the like. The tissue can then be cultured to obtain a population of isolated placental cells. Typically, the placental tissue is disrupted using, e.g., culture medium, a saline solution, or a stem cell collection composition (see Section 5.5.1 and below).

The placenta can be dissected into components prior to physical disruption and/or enzymatic digestion and stem cell recovery. Isolated placental cells can be obtained from all or a portion of the amniotic membrane, chorion, umbilical cord, placental cotyledons, or any combination thereof, including from a whole placenta. Preferably, isolated placental cells are obtained from placental tissue comprising amnion and chorion. Typically, isolated placental cells can be obtained by disruption of a small block of placental tissue, e.g., a block of placental tissue that is about 1, 2, 3, 4, 5, 6, 7, 8, 9, 10, 20, 30, 40, 50, 60, 70, 80, 90, 100, 200, 300, 400, 500, 600, 700, 800, 900 or about 1000 cubic millimeters in volume. Any method of physical disruption can be used, provided that the method of disruption leaves a plurality, more preferably a majority, and more preferably at least 60%, 70%, 80%, 90%, 95%, 98%, or 99% of the cells in said organ viable, as determined by, e.g., trypan blue exclusion.

The isolated adherent placental cells can generally be collected from a placenta, or portion thereof, at any time within about the first three days post-expulsion, but preferably between about 8 hours and about 18 hours post-expulsion.

In a specific embodiment, the disrupted tissue is cultured in tissue culture medium suitable for the proliferation of isolated placental cells (see, e.g., Section 5.6, below, describing the culture of placental stem cells).

In another specific embodiment, isolated placental cells are collected by physical disruption of placental tissue, wherein the physical disruption includes enzymatic digestion, which can be accomplished by use of one or more tissue-digesting enzymes. The placenta, or a portion thereof, may also be physically disrupted and digested with one or more enzymes, and the resulting material then immersed in, or mixed into, a cell collection composition.

A preferred cell collection composition comprises one or more tissue-disruptive enzyme(s). Enzymes that can be used to disrupt placenta tissue include papain, deoxyribonucleases, serine proteases, such as trypsin, chymotrypsin, collagenase, dispase or elastase. Serine proteases may be inhibited by alpha 2 microglobulin in serum and therefore the medium used for digestion is usually serum-free. EDTA and DNase are commonly used in enzyme digestion procedures to increase the efficiency of cell recovery. The digestate is preferably diluted so as to avoid trapping cells within the viscous digest.

Any combination of tissue digestion enzymes can be used. Typical concentrations for digestion using trypsin include, 0.1% to about 2% trypsin, e.g., about 0.25% trypsin. Proteases can be used in combination, that is, two or more proteases in the same digestion reaction, or can be used sequentially in order to liberate placental cells, e.g., placental stem cells and placental multipotent cells. For example, in one embodiment, a placenta, or part thereof, is digested first with an appropriate amount of collagenase I at about 1 to about 2 mg/ml for, e.g., 30 minutes, followed by digestion with trypsin, at a concentration of about 0.25%, for, e.g., 10 minutes, at 37° C. Serine proteases are preferably used consecutively following use of other enzymes.

In another embodiment, the tissue can further be disrupted by the addition of a chelator, e.g., ethylene glycol bis(2-aminoethyl ether)-N,N,N'N'-tetraacetic acid (EGTA) or ethylenediaminetetraacetic acid (EDTA) to the stem cell collection composition comprising the stem cells, or to a solution in which the tissue is disrupted and/or digested prior to isolation of the stem cells with the stem cell collection composition.

Following digestion, the digestate is washed, for example, three times with culture medium, and the washed cells are seeded into culture flasks. The cells are then isolated by differential adherence, and characterized for, e.g., viability, cell surface markers, differentiation, and the like.

It will be appreciated that where an entire placenta, or portion of a placenta comprising both fetal and maternal cells (for example, where the portion of the placenta comprises the chorion or cotyledons), the placental cells isolated can comprise a mix of placental cells derived from both fetal and maternal sources. Where a portion of the placenta that comprises no, or a negligible number of, maternal cells (for example, amnion), the placental cells isolated therefrom will comprise almost exclusively fetal placental cells (that is, placental cells having the genotype of the fetus).

Placental cells, e.g., the placental cells described in Section 5.4.2, above, can be isolated from disrupted placental tissue by differential trypsinization (see Section 5.5.5, below) followed by culture in one or more new culture containers in fresh proliferation medium, optionally followed by a second differential trypsinization step.

5.5.4 Placental Perfusion

Placental cells, e.g., the placental cells described in Section 5.4.2, above, can also be obtained by perfusion of the mammalian placenta. Methods of perfusing mammalian placenta to obtain placental cells are disclosed, e.g., in Hariri, U.S. Pat. Nos. 7,045,148 and 7,255,729, in U.S. Patent Application Publication Nos. 2007/0275362 and 2007/0190042, the disclosures of each of which are incorporated herein by reference in their entireties.

Placental cells can be collected by perfusion, e.g., through the placental vasculature, using, e.g., a cell collection composition as a perfusion solution. In one embodiment, a mammalian placenta is perfused by passage of perfusion solution through either or both of the umbilical artery and umbilical vein. The flow of perfusion solution through the placenta may be accomplished using, e.g., gravity flow into the placenta. Preferably, the perfusion solution is forced through the placenta using a pump, e.g., a peristaltic pump. The umbilical vein can be, e.g., cannulated with a cannula, e.g., a TEFLON® or plastic cannula, that is connected to a sterile connection apparatus, such as sterile tubing. The sterile connection apparatus is connected to a perfusion manifold.

In preparation for perfusion, the placenta is preferably oriented (e.g., suspended) in such a manner that the umbilical artery and umbilical vein are located at the highest point of the placenta. The placenta can be perfused by passage of a perfusion fluid through the placental vasculature and surrounding tissue. The placenta can also be perfused by passage of a perfusion fluid into the umbilical vein and collection from the umbilical arteries, or passage of a perfusion fluid into the umbilical arteries and collection from the umbilical vein.

In one embodiment, for example, the umbilical artery and the umbilical vein are connected simultaneously, e.g., to a pipette that is connected via a flexible connector to a reservoir of the perfusion solution. The perfusion solution is passed into the umbilical vein and artery. The perfusion solution exudes from and/or passes through the walls of the blood vessels into the surrounding tissues of the placenta, and is collected in a suitable open vessel from the surface of the placenta that was attached to the uterus of the mother during gestation. The perfusion solution may also be introduced through the umbilical cord opening and allowed to flow or percolate out of openings in the wall of the placenta which interfaced with the maternal uterine wall. Placental cells that are collected by this method, which can be referred to as a "pan" method, are typically a mixture of fetal and maternal cells.

In another embodiment, the perfusion solution is passed through the umbilical veins and collected from the umbilical artery, or is passed through the umbilical artery and collected from the umbilical veins. Placental cells collected by this method, which can be referred to as a "closed circuit" method, are typically almost exclusively fetal.

It will be appreciated that perfusion using the pan method, that is, whereby perfusate is collected after it has exuded from the maternal side of the placenta, results in a mix of fetal and maternal cells. As a result, the cells collected by this method can comprise a mixed population of placental cells, e.g., placental stem cells or placental multipotent cells, of both fetal and maternal origin. In contrast, perfusion solely through the placental vasculature in the closed circuit method, whereby perfusion fluid is passed through one or two placental vessels and is collected solely through the remaining vessel(s), results in the collection of a population of placental cells almost exclusively of fetal origin.

The closed circuit perfusion method can, in one embodiment, be performed as follows. A post-partum placenta is obtained within about 48 hours after birth. The umbilical cord is clamped and cut above the clamp. The umbilical cord can be discarded, or can processed to recover, e.g., umbilical cord stem cells, and/or to process the umbilical cord membrane for the production of a biomaterial. The amniotic membrane can be retained during perfusion, or can be separated from the chorion, e.g., using blunt dissection with the fingers. If the amniotic membrane is separated from the chorion prior to perfusion, it can be, e.g., discarded, or processed, e.g., to obtain stem cells by enzymatic digestion, or to produce, e.g., an amniotic membrane biomaterial, e.g., the biomaterial described in U.S. Application Publication No. 2004/0048796, the disclosure of which is incorporated by reference herein in its entirety. After cleaning the placenta of all visible blood clots and residual blood, e.g., using sterile gauze, the umbilical cord vessels are exposed, e.g., by partially cutting the umbilical cord membrane to expose a cross-section of the cord. The vessels are identified, and opened, e.g., by advancing a closed alligator clamp through the cut end of each vessel. The apparatus, e.g., plastic tubing connected to a perfusion device or peristaltic pump, is then inserted into each of the placental arteries. The pump can be any pump suitable for the purpose, e.g., a peristaltic pump. Plastic tubing, connected to a sterile collection reservoir, e.g., a blood bag such as a 250 mL collection bag, is then inserted into the placental vein. Alternatively, the tubing connected to the pump is inserted into the placental vein, and tubes to a collection reservoir(s) are inserted into one or both of the placental arteries. The placenta is then perfused with a volume of perfusion solution, e.g., about 750 ml of perfusion solution. Cells in the perfusate are then collected, e.g., by centrifugation. In certain embodiments, the placenta is perfused with perfusion solution, e.g., 100-300 mL perfusion solution, to remove residual blood prior to perfusion to collect placental cells, e.g., placental stem cells and/or placental multipotent cells. In another embodiment, the placenta is not perfused with perfusion solution to remove residual blood prior to perfusion to collect placental cells.

In one embodiment, the proximal umbilical cord is clamped during perfusion, and more preferably, is clamped within 4-5 cm (centimeter) of the cord's insertion into the placental disc.

The first collection of perfusion fluid from a mammalian placenta during the exsanguination process is generally colored with residual red blood cells of the cord blood and/or placental blood. The perfusion fluid becomes more colorless as perfusion proceeds and the residual cord blood cells are washed out of the placenta. Generally from 30 to 100 ml (milliliter) of perfusion fluid is adequate to initially exsanguinate the placenta, but more or less perfusion fluid may be used depending on the observed results.

The volume of perfusion liquid used to isolate placental cells may vary depending upon the number of cells to be collected, the size of the placenta, the number of collections to be made from a single placenta, etc. In various embodiments, the volume of perfusion liquid may be from 50 mL to 5000 mL, 50 mL to 4000 mL, 50 mL to 3000 mL, 100 mL to 2000 mL, 250 mL to 2000 mL, 500 mL to 2000 mL, or 750 mL to 2000 mL. Typically, the placenta is perfused with 700-800 mL of perfusion liquid following exsanguination.

The placenta can be perfused a plurality of times over the course of several hours or several days. Where the placenta is to be perfused a plurality of times, it may be maintained or cultured under aseptic conditions in a container or other suitable vessel, and perfused with the cell collection composition, or a standard perfusion solution (e.g., a normal saline solution such as phosphate buffered saline ("PBS")) with or without an anticoagulant (e.g., heparin, warfarin sodium, coumarin, bishydroxycoumarin), and/or with or without an antimicrobial agent (e.g., β-mercaptoethanol (0.1 mM); antibiotics such as streptomycin (e.g., at 40-100 µg/ml), penicillin (e.g., at 40 U/ml), amphotericin B (e.g., at 0.5 µg/ml). In one embodiment, an isolated placenta is maintained or cultured for a period of time without collecting the perfusate, such that the placenta is maintained or cultured for 1, 2, 3, 4, 5, 6, 7, 8, 9, 10, 11, 12, 13, 14, 15, 16, 17, 18, 19, 20, 21, 22, 23, or 24 hours, or 2 or 3 or more days before perfusion and collection of perfusate. The perfused placenta can be maintained for one or more additional time(s), e.g., 1, 2, 3, 4, 5, 6, 7, 8, 9, 10, 11, 12, 13, 14, 15, 16, 17, 18, 19, 20, 21, 22, 23, 24 or more hours, and perfused a second time with, e.g., 700-800 mL perfusion fluid. The placenta can be perfused 1, 2, 3, 4, 5 or more times, for example, once every 1, 2, 3, 4, 5 or 6 hours. In a preferred embodiment, perfusion of the placenta and collection of perfusion solution, e.g., cell collection composition, is repeated until the number of recovered nucleated cells falls below 100 cells/ml. The perfusates at different time points can be further processed individually to recover time-dependent populations of cells, e.g., stem cells. Perfusates from different time points can also be pooled. In a preferred embodiment, placental cells are collected at a time or times between about 8 hours and about 18 hours post-expulsion.

Perfusion preferably results in the collection of significantly more placental cells than the number obtainable from a mammalian placenta not perfused with said solution, and not otherwise treated to obtain placental cells (e.g., by tissue disruption, e.g., enzymatic digestion). In this context, "significantly more" means at least 10% more. Perfusion yields significantly more placental cells than, e.g., the number of placental cells isolatable from culture medium in which a placenta, or portion thereof, has been cultured.

Placental cells can be isolated from placenta by perfusion with a solution comprising one or more proteases or other tissue-disruptive enzymes. In a specific embodiment, a placenta or portion thereof (e.g., amniotic membrane, amnion and chorion, placental lobule or cotyledon, umbilical cord, or combination of any of the foregoing) is brought to 25-37° C., and is incubated with one or more tissue-disruptive enzymes in 200 mL of a culture medium for 30 minutes. Cells from the perfusate are collected, brought to 4° C., and washed with a cold inhibitor mix comprising 5 mM EDTA, 2 mM dithiothreitol and 2 mM beta-mercaptoethanol. The placental cells are washed after several minutes with a cold (e.g., 4° C.) stem cell collection composition.

5.5.5 Isolation, Sorting, and Characterization of Placental Cells

The isolated placental cells, e.g., the cells described in Section 5.4.2, above, whether obtained by perfusion or physical disruption, e.g., by enzymatic digestion, can initially be purified from (i.e., be isolated from) other cells by Ficoll gradient centrifugation. Such centrifugation can follow any standard protocol for centrifugation speed, etc. In one embodiment, for example, cells collected from the placenta are recovered from perfusate by centrifugation at 5000×g for 15 minutes at room temperature, which separates cells from, e.g., contaminating debris and platelets. In another embodiment, placental perfusate is concentrated to about 200 ml, gently layered over Ficoll, and centrifuged at about 1100×g for 20 minutes at 22° C., and the low-density interface layer of cells is collected for further processing.

Cell pellets can be resuspended in fresh stem cell collection composition, or a medium suitable for cell maintenance, e.g., stem cell maintenance, for example, IMDM serum-free medium containing 2 U/ml heparin and 2 mM EDTA (GibcoBRL, NY). The total mononuclear cell fraction can be isolated, e.g., using Lymphoprep (Nycomed Pharma, Oslo, Norway) according to the manufacturer's recommended procedure.

Placental cells obtained by perfusion or digestion can, for example, be further, or initially, isolated by differential trypsinization using, e.g., a solution of 0.05% trypsin with 0.2% EDTA (Sigma, St. Louis Mo.). Differential trypsinization is possible because the isolated placental cells, which are tissue culture plastic-adherent, typically detach from the plastic surfaces within about five minutes whereas other adherent populations typically require more than 20-30 minutes incubation. The detached placental cells can be harvested following trypsinization and trypsin neutralization, using, e.g., Trypsin Neutralizing Solution (TNS, Cambrex). In one embodiment of isolation of adherent cells, aliquots of, for example, about 5-10×10$^6$ cells are placed in each of several T-75 flasks, preferably fibronectin-coated T75 flasks. In such an embodiment, the cells can be cultured with commercially available Mesenchymal Stem Cell Growth Medium (MSCGM) (Cambrex), and placed in a tissue culture incubator (37° C., 5% CO$_2$). After 10 to 15 days, non-adherent cells are removed from the flasks by washing with PBS. The PBS is then replaced by MSCGM. Flasks are preferably examined daily for the presence of various adherent cell types and in particular, for identification and expansion of clusters of fibroblastoid cells.

The number and type of cells collected from a mammalian placenta can be monitored, for example, by measuring changes in morphology and cell surface markers using standard cell detection techniques such as flow cytometry, cell sorting, immunocytochemistry (e.g., staining with tissue specific or cell-marker specific antibodies) fluorescence activated cell sorting (FACS), magnetic activated cell sorting (MACS), by examination of the morphology of cells using light or confocal microscopy, and/or by measuring changes in gene expression using techniques well known in the art, such as PCR and gene expression profiling. These techniques can be used, too, to identify cells that are positive for one or more particular markers. For example, using antibodies to CD34, one can determine, using the techniques above, whether a cell comprises a detectable amount of CD34; if so, the cell is CD34$^+$. Likewise, if a cell produces enough OCT-4 RNA to be detectable by RT-PCR, or significantly more OCT-4 RNA than an adult cell, the cell is OCT-4$^+$. Antibodies to cell surface markers (e.g., CD markers such as CD34) and the sequence of stem cell-specific genes, such as OCT-4, are well-known in the art.

Placental cells, particularly cells that have been isolated by Ficoll separation, differential adherence, or a combination of both, may be sorted using a fluorescence activated cell sorter (FACS). Fluorescence activated cell sorting (FACS) is a well-known method for separating particles, including cells, based on the fluorescent properties of the particles (Kamarch, 1987, Methods Enzymol, 151:150-165). Laser excitation of fluorescent moieties in the individual particles results in a small electrical charge allowing electromagnetic separation of positive and negative particles from a mixture. In one embodiment, cell surface marker-specific antibodies or ligands are labeled with distinct fluorescent labels. Cells are processed through the cell sorter, allowing separation of cells based on their ability to bind to the antibodies used. FACS sorted particles may be directly deposited into individual wells of 96-well or 384-well plates to facilitate separation and cloning.

In one sorting scheme, cells from placenta, e.g., are sorted on the basis of expression of one or more of the markers CD34, CD38, CD44, CD45, CD73, CD105, OCT-4 and/or HLA-G. This can be accomplished in connection with procedures to select such cells on the basis of their adherence properties in culture. For example, tissue culture plastic adherence selection can be accomplished before or after sorting on the basis of marker expression. In one embodiment, for example, cells are sorted first on the basis of their expression of CD34; CD34$^-$ cells are retained, and CD34$^-$ cells that are additionally CD200$^+$HLA-G$^+$ are separated from all other CD34$^-$ cells. In another embodiment, cells from placenta are sorted based on their expression of markers CD200 and/or HLA-G; for example, cells displaying either of these markers are isolated for further use. Cells that express, e.g., CD200 and/or HLA-G can, in a specific embodiment, be further sorted based on their expression of CD73 and/or CD105, or epitopes recognized by antibodies SH2, SH3 or SH4, or lack of expression of CD34, CD38 or CD45. For example, in another embodiment, placental cells are sorted by expression, or lack thereof, of CD200, HLA-G, CD73, CD105, CD34, CD38 and CD45, and placental cells that are CD200$^+$, HLA-G$^+$, CD73$^+$, CD105$^+$, CD34$^-$, CD38$^-$ and CD45$^-$ are isolated from other placental cells for further use.

In specific embodiments of any of the above embodiments of sorted placental cells, at least 50%, 60%, 70%, 80%, 90% or 95% of the cells in a cell population remaining after sorting are said isolated placental cells. Placental cells can be sorted by one or more of any of the markers described in Section 5.4.2, above.

In a specific embodiment, placental cells that are (1) adherent to tissue culture plastic, and (2) CD10$^+$, CD34$^-$ and CD105$^+$ are sorted from (i.e., isolated from) other placental cells. In another specific embodiment, placental cells that are (1) adherent to tissue culture plastic, and (2) CD10$^+$, CD34$^-$, CD105$^+$ and CD200$^+$ are sorted from (i.e., isolated from)

other placental cells. In another specific embodiment, placental cells that are (1) adherent to tissue culture plastic, and (2) CD10$^+$, CD34$^-$, CD45$^-$, CD90$^+$, CD105$^+$ and CD200$^+$ are sorted from (i.e., isolated from) other placental cells.

With respect to antibody-mediated detection and sorting of placental cells, e.g., placental stem cells or placental multipotent cells, any antibody, specific for a particular marker, can be used, in combination with any fluorophore or other label suitable for the detection and sorting of cells (e.g., fluorescence-activated cell sorting). Antibody/fluorophore combinations to specific markers include, but are not limited to, fluorescein isothiocyanate (FITC) conjugated monoclonal antibodies against HLA-G (available from Serotec, Raleigh, N.C.), CD10 (available from BD Immunocytometry Systems, San Jose, Calif.), CD44 (available from BD Biosciences Pharmingen, San Jose, Calif.), and CD105 (available from R&D Systems Inc., Minneapolis, Minn.); phycoerythrin (PE) conjugated monoclonal antibodies against CD44, CD200, CD117, and CD13 (BD Biosciences Pharmingen); phycoerythrin-Cy7 (PE Cy7) conjugated monoclonal antibodies against CD33 and CD10 (BD Biosciences Pharmingen); allophycocyanin (APC) conjugated streptavidin and monoclonal antibodies against CD38 (BD Biosciences Pharmingen); and Biotinylated CD90 (BD Biosciences Pharmingen). Other antibodies that can be used include, but are not limited to, CD133-APC (Miltenyi), KDR-Biotin (CD309, Abcam), CytokeratinK-Fitc (Sigma or Dako), HLA ABC-Fitc (BD), HLA DR,DQ,DP-PE (BD), β-2-microglobulin-PE (BD), CD80-PE (BD) and CD86-APC (BD).

Other antibody/label combinations that can be used include, but are not limited to, CD45-PerCP (peridin chlorophyll protein); CD44-PE; CD19-PE; CD10-F (fluorescein); HLA-G-F and 7-amino-actinomycin-D (7-AAD); HLA-ABC-F; and the like.

The isolated placental cells provided herein can be assayed for CD117 or CD133 using, for example, phycoerythrin-Cy5 (PE Cy5) conjugated streptavidin and biotin conjugated monoclonal antibodies against CD117 or CD133; however, using this system, the cells can appear to be positive for CD117 or CD133, respectively, because of a relatively high background.

The isolated placental cells can be labeled with an antibody to a single marker and detected and/sorted. Placental cells can also be simultaneously labeled with multiple antibodies to different markers.

In another embodiment, magnetic beads can be used to separate cells. The cells may be sorted using a magnetic activated cell sorting (MACS) technique, a method for separating particles based on their ability to bind magnetic beads (0.5-100 μm diameter). A variety of useful modifications can be performed on the magnetic microspheres, including covalent addition of antibody that specifically recognizes a particular cell surface molecule or hapten. The beads are then mixed with the cells to allow binding. Cells are then passed through a magnetic field to separate out cells having the specific cell surface marker. In one embodiment, these cells can then isolated and re-mixed with magnetic beads coupled to an antibody against additional cell surface markers. The cells are again passed through a magnetic field, isolating cells that bound both the antibodies. Such cells can then be diluted into separate dishes, such as microtiter dishes for clonal isolation.

Isolated placental cells can also be characterized and/or sorted based on cell morphology and growth characteristics. For example, isolated placental cells can be characterized as having, and/or selected on the basis of, e.g., a fibroblastoid appearance in culture. The isolated placental cells can also be characterized as having, and/or be selected, on the basis of their ability to form embryoid-like bodies. In one embodiment, for example, placental cells that are fibroblastoid in shape, express CD73 and CD105, and produce one or more embryoid-like bodies in culture are isolated from other placental cells. In another embodiment, OCT-4$^+$ placental cells that produce one or more embryoid-like bodies in culture are isolated from other placental cells.

In another embodiment, isolated placental cells can be identified and characterized by a colony forming unit assay. Colony forming unit assays are commonly known in the art, such as MESEN CULT™ medium (Stem Cell Technologies, Inc., Vancouver British Columbia)

The isolated placental cells can be assessed for viability, proliferation potential, and longevity using standard techniques known in the art, such as trypan blue exclusion assay, fluorescein diacetate uptake assay, propidium iodide uptake assay (to assess viability); and thymidine uptake assay, MTT cell proliferation assay (to assess proliferation). Longevity may be determined by methods well known in the art, such as by determining the maximum number of population doubling in an extended culture.

Isolated placental cells, e.g., the isolated placental cells described in Section 5.4.2, above, can also be separated from other placental cells using other techniques known in the art, e.g., selective growth of desired cells (positive selection); selective destruction of unwanted cells (negative selection); separation based upon differential cell agglutinability in the mixed population as, for example, with soybean agglutinin; freeze-thaw procedures; filtration; conventional and zonal centrifugation; centrifugal elutriation (counter-streaming centrifugation); unit gravity separation; countercurrent distribution; electrophoresis; and the like.

5.6 Culture of Isolated Placental Cells 5.6.1 Culture Media

Isolated placental cells, or populations of isolated placental cells, or cells or placental tissue from which placental stem cells grow out, can be used to initiate, or seed, cell cultures. Cells are generally transferred to sterile tissue culture vessels either uncoated or coated with extracellular matrix or ligands such as laminin, collagen (e.g., native or denatured), gelatin, fibronectin, ornithine, vitronectin, and extracellular membrane protein (e.g., MATRIGEL® (BD Discovery Labware, Bedford, Mass.)).

Isolated placental cells can be cultured in any medium, and under any conditions, recognized in the art as acceptable for the culture of cells, e.g., stem cells. Preferably, the culture medium comprises serum. The isolated placental cells can be cultured in, for example, DMEM-LG (Dulbecco's Modified Essential Medium, low glucose)/MCDB 201 (chick fibroblast basal medium) containing ITS (insulin-transferrin-selenium), LA+BSA (linoleic acid-bovine serum albumin), dexamethasone L-ascorbic acid, PDGF, EGF, IGF-1, and penicillin/streptomycin; DMEM-HG (high glucose) comprising 10% fetal bovine serum (FBS); DMEM-HG comprising 15% FBS; IMDM (Iscove's modified Dulbecco's medium) comprising 10% FBS, 10% horse serum, and hydrocortisone; M199 comprising 1% to 20% FBS, EGF, and heparin; α-MEM (minimal essential medium) comprising 10% FBS, GLUTAMAX™ and gentamicin; DMEM comprising 10% FBS, GLUTAMAX™ and gentamicin, etc.

Other media in that can be used to culture placental cells include DMEM (high or low glucose), Eagle's basal medium, Ham's F10 medium (F10), Ham's F-12 medium (F12), Iscove's modified Dulbecco's medium, Mesenchymal Stem Cell Growth Medium (MSCGM), Liebovitz's L-15 medium, MCDB, DMEM/F12, RPMI 1640, advanced DMEM (Gibco), DMEM/MCDB201 (Sigma), and CELL-GRO FREE.

The culture medium can be supplemented with one or more components including, for example, serum (e.g., fetal bovine serum (FBS), preferably about 2-15% (v/v); equine (horse) serum (ES); human serum (HS)); beta-mercaptoethanol (BME), preferably about 0.001% (v/v); one or more growth factors, for example, platelet-derived growth factor (PDGF), epidermal growth factor (EGF), basic fibroblast growth factor (bFGF), insulin-like growth factor-1 (IGF-1), leukemia inhibitory factor (LIF), vascular endothelial growth factor (VEGF), and erythropoietin (EPO); amino acids, including L-valine; and one or more antibiotic and/or antimycotic agents to control microbial contamination, such as, for example, penicillin G, streptomycin sulfate, amphotericin B, gentamicin, and nystatin, either alone or in combination.

The isolated placental cells can be cultured in standard tissue culture conditions, e.g., in tissue culture dishes or multiwell plates. The isolated placental cells can also be cultured using a hanging drop method. In this method, isolated placental cells are suspended at about $1\times10^4$ cells per mL in about 5 mL of medium, and one or more drops of the medium are placed on the inside of the lid of a tissue culture container, e.g., a 100 mL Petri dish. The drops can be, e.g., single drops, or multiple drops from, e.g., a multichannel pipetter. The lid is carefully inverted and placed on top of the bottom of the dish, which contains a volume of liquid, e.g., sterile PBS sufficient to maintain the moisture content in the dish atmosphere, and the stem cells are cultured.

In one embodiment, isolated placental cells are cultured in the presence of a compound that acts to maintain an undifferentiated phenotype in the isolated placental cells. In a specific embodiment, the compound is a substituted 3,4-dihydropyridimol[4,5-d]pyrimidine. In a more specific embodiment, the compound is a compound having the following chemical structure:

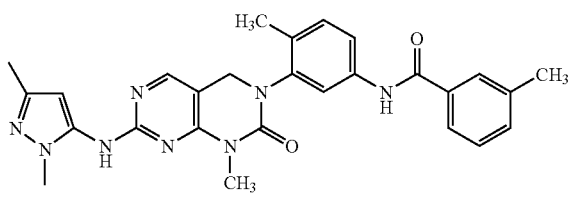

The compound can be contacted with isolated placental cells, or a population of isolated placental cells, at a concentration of, for example, between about 1 µM to about 10 µM.

5.6.2 Expansion and Proliferation of Placental Cells

Once an isolated placental cell, or population of isolated placental cells (e.g., a placental cell or population of placental cells separated from at least 50% of the placental cells with which the stem cell or population of stem cells is normally associated in vivo), the cell or population of cells can be proliferated and expanded in vitro. For example, a population of the isolated placental cells can be cultured in tissue culture containers, e.g., dishes, flasks, multiwell plates, or the like, for a sufficient time for the cells to proliferate to 70-90% confluence, that is, until the cells and their progeny occupy 70-90% of the culturing surface area of the tissue culture container.

The isolated placental cells can be seeded in culture vessels at a density that allows cell growth. For example, the cells may be seeded at low density (e.g., about 1,000 to about 5,000 cells/cm$^2$) to high density (e.g., about 50,000 or more cells/cm$^2$). In a preferred embodiment, the cells are cultured in the presence of about 0 to about 5 percent by volume $CO_2$ in air. In some preferred embodiments, the cells are cultured at about 2 to about 25 percent $O_2$ in air, preferably about 5 to about 20 percent $O_2$ in air. The cells preferably are cultured at about 25° C. to about 40° C., preferably 37° C. The cells are preferably cultured in an incubator. The culture medium can be static or agitated, for example, using a bioreactor. Placental cells, e.g., placental stem cells or placental multipotent cells, preferably are grown under low oxidative stress (e.g., with addition of glutathione, ascorbic acid, catalase, tocopherol, N-acetylcysteine, or the like).

Once confluence of less than 100%, for example, 70% to 90% is obtained, the cells may be passaged. For example, the cells can be enzymatically treated, e.g., trypsinized, using techniques well-known in the art, to separate them from the tissue culture surface. After removing the cells by pipetting and counting the cells, about 10,000-100,000 cells/cm$^2$ are passaged to a new culture container containing fresh culture medium. Typically, the new medium is the same type of medium from which the isolated placental cells were removed. The isolated placental cells can be passaged about, at least, or no more than 1, 2, 3, 4, 5, 6, 7, 8, 9, 10, 12, 14, 16, 18, or 20 times, or more.

5.6.3 Populations of Isolated Placental Cells

Also provided herein are populations of isolated placental cells, e.g., the isolated placental cells described in Section 5.4.2, above, useful in the treatment of disruption of blood flow in or around the brain or CNS. Populations of isolated placental cells can be isolated directly from one or more placentas; that is, the cell population can be a population of placental cells comprising the isolated placental cells, wherein the isolated placental cells are obtained from, or contained within, perfusate, or obtained from, or contained within, disrupted placental tissue, e.g., placental tissue digestate (that is, the collection of cells obtained by enzymatic digestion of a placenta or part thereof). The isolated placental cells described herein can also be cultured and expanded to produce populations of the isolated placental cells. Populations of placental cells comprising the isolated placental cells can also be cultured and expanded to produce placental cell populations.

Placental cell populations useful in the methods of treatment provided herein comprise the isolated placental cells, for example, the isolated placental cells as described in Section 5.4.2 herein. In various embodiments, at least 10%, 20%, 30%, 40%, 50%, 60%, 70%, 80%, 90%, 95%, or 99% of the cells in a placental cell population are the isolated placental cells. That is, a population of the isolated placental cells can comprise, e.g., as much as 1%, 5%, 10%, 20%, 30%, 40%, 50%, 60%, 70%, 80%, 90% cells that are not the isolated placental cells.

Isolated placental cell populations useful in the treatment of disruption of blood flow in or around the brain or CNS can be produced by, e.g., selecting isolated placental cells, whether derived from enzymatic digestion or perfusion, that express particular markers and/or particular culture or morphological characteristics. In one embodiment, for example, a cell population is produced by selecting placental cells that (a) adhere to a substrate, and (b) express CD200 and HLA-G; and isolating said cells from other cells to form a cell population. In another embodiment, a cell population is produced by selecting placental cells that express CD200 and HLA-G, and isolating said cells from other cells to form a cell population. In another embodiment, a cell population is produced by selecting placental cells that (a) adhere to a substrate, and (b) express CD73, CD105, and CD200; and isolating said cells from other cells to form a cell population. In another embodiment, a cell population is produced by identifying placental cells that express CD73, CD105, and CD200, and isolating said cells from other cells to form a cell population. In another embodiment, a cell population is produced by selecting placental cells that (a) adhere to a substrate and (b) express CD200 and OCT-4; and isolating said cells from other cells to form a cell population. In another embodiment, a cell population is produced by selecting placental cells that express CD200 and OCT-4, and isolating said cells from other cells to form a cell population. In another embodiment, a cell population is produced by selecting placental cells that (a) adhere to a substrate, (b) express CD73 and CD105, and (c) facilitate the formation of one or more embryoid-like bodies in a population of placental cells comprising said stem cell when said population is cultured under conditions that allow for the formation of an embryoid-like body; and isolating said cells from other cells to form a cell population. In another embodiment, a cell population is produced by selecting placental cells that express CD73 and CD105, and facilitate the formation of one or more embryoid-like bodies in a population of placental cells comprising said stem cell when said population is cultured under conditions that allow for the formation of an embryoid-like body, and isolating said cells from other cells to form a cell population. In another embodiment, a cell population is produced by selecting placental cells that (a) adhere to a substrate, and (b) express CD73, CD105 and HLA-G; and isolating said cells from other cells to form a cell population. In another embodiment, a cell population is produced by selecting placental cells that express CD73, CD105 and HLA-G, and isolating said cells from other cells to form a cell population. In another embodiment, the method of producing a cell population comprises selecting placental cells that (a) adhere to a substrate, (b) express OCT-4, and (c) facilitate the formation of one or more embryoid-like bodies in a population of placental cells comprising said stem cell when said population is cultured under conditions that allow for the formation of an embryoid-like body; and isolating said cells from other cells to form a cell population. In another embodiment, a cell population is produced by selecting placental cells that express OCT-4, and facilitate the formation of one or more embryoid-like bodies in a population of placental cells comprising said stem cell when said population is cultured under conditions that allow for the formation of an embryoid-like body, and isolating said cells from other cells to form a cell population.

In another embodiment, a cell population is produced by selecting placental cells that (a) adhere to a substrate, and (b) express CD10 and CD105, and do not express CD34; and isolating said cells from other cells to form a cell population. In another embodiment, a cell population is produced by selecting placental cells that express CD10 and CD105, and do not express CD34, and isolating said cells from other cells to form a cell population. In another embodiment, a cell population is produced by selecting placental cells that (a) adhere to a substrate, and (b) express CD10, CD105, and CD200, and do not express CD34; and isolating said cells from other cells to form a cell population. In another embodiment, a cell population is produced by selecting placental cells that express CD10, CD105, and CD200, and do not express CD34, and isolating said cells from other cells to form a cell population. In another more specific embodiment, a cell population is produced by selecting placental cells that (a) adhere to a substrate, and (b) express CD10, CD90, CD105 and CD200, and do not express CD34 and CD45; and isolating said cells from other cells to form a cell population. In another more specific embodiment, a cell population is produced by selecting placental cells that express CD10, CD90, CD105 and CD200, and do not express CD34 and CD45, and isolating said cells from other cells to form a cell population.

Such cell populations, or combinations thereof, can be used to treat disruption of blood flow in or around the brain or CNS, e.g., a symptom of a disruption or a neurological deficit attributable to such a disruption.

In any of the above embodiments, selection of the isolated cell populations can additionally comprise selecting placental cells that express ABC-p (a placenta-specific ABC transporter protein; see, e.g., Allikmets et al., *Cancer Res.* 58(23): 5337-9 (1998)). The method can also comprise selecting cells exhibiting at least one characteristic specific to, e.g., a mesenchymal stem cell, for example, expression of CD44, expression of CD90, or expression of a combination of the foregoing.

In the above embodiments, the substrate can be any surface on which culture and/or selection of cells, e.g., isolated placental cells, can be accomplished. Typically, the substrate is plastic, e.g., tissue culture dish or multiwell plate plastic. Tissue culture plastic can be coated with a biomolecule, e.g., laminin or fibronectin.

Cells, e.g., isolated placental cells, can be selected for a placental cell population by any means known in the art of cell selection. For example, cells can be selected using an antibody or antibodies to one or more cell surface markers, for example, in flow cytometry or FACS. Selection can be accomplished using antibodies in conjunction with magnetic beads. Antibodies that are specific for certain stem cell-related markers are known in the art. For example, antibodies to OCT-4 (Abcam, Cambridge, Mass.), CD200 (Abcam), HLA-G (Abcam), CD73 (BD Biosciences Pharmingen, San Diego, Calif.), CD105 (Abcam; BioDesign International, Saco, Me.), etc. Antibodies to other markers are also available commercially, e.g., CD34, CD38 and CD45 are available from, e.g., StemCell Technologies or BioDesign International.

The isolated placental cell populations can comprise placental cells that are not stem cells, or cells that are not placental cells.

The isolated placental cell populations provided herein can be combined with one or more populations of non-stem cells or non-placental cells. For example, a population of isolated placental cells can be combined with blood (e.g., placental blood or umbilical cord blood), blood-derived stem cells (e.g., stem cells derived from placental blood or umbilical cord blood), umbilical cord stem cells, populations of blood-derived nucleated cells, bone marrow-derived mesenchymal cells, bone-derived stem cell populations, crude bone marrow, adult (somatic) stem cells, populations of stem cells contained within tissue, cultured stem cells, populations of fully-differentiated cells (e.g., chondrocytes, fibroblasts, amniotic cells, osteoblasts, muscle cells, cardiac cells, etc.) and the like. In a specific embodiment, a population of cells useful for the treatment of disruption of blood flow in or around the brain or CNS comprises isolated placental cells and isolated umbilical cord cells. Cells in an isolated placental cell population can be combined with a plurality of cells of another type in ratios of about 100,000,000:1, 50,000,000:1, 20,000,000:1, 10,000,000:1, 5,000,000:1, 2,000,000:1, 1,000,000:1, 500,000:1, 200,000:1, 100,000:1, 50,000:1, 20,000:1, 10,000:1, 5,000:1, 2,000:1, 1,000:1, 500:1, 200:1, 100:1, 50:1, 20:1, 10:1, 5:1, 2:1, 1:1; 1:2; 1:5; 1:10; 1:100; 1:200; 1:500; 1:1,000; 1:2,000; 1:5,000; 1:10,000; 1:20,000;

1:50,000; 1:100,000; 1:500,000; 1:1,000,000; 1:2,000,000; 1:5,000,000; 1:10,000,000; 1:20,000,000; 1:50,000,000; or about 1:100,000,000, comparing numbers of total nucleated cells in each population. Cells in an isolated placental cell population can be combined with a plurality of cells of a plurality of cell types, as well.

In one embodiment, an isolated population of placental cells is combined with a plurality of hematopoietic stem cells. Such hematopoietic stem cells can be, for example, contained within unprocessed placental, umbilical cord blood or peripheral blood; in total nucleated cells from placental blood, umbilical cord blood or peripheral blood; in an isolated population of $CD34^+$ cells from placental blood, umbilical cord blood or peripheral blood; in unprocessed bone marrow; in total nucleated cells from bone marrow; in an isolated population of $CD34^+$ cells from bone marrow, or the like.

5.7 Production of a Placental Cell Bank

Isolated cells from postpartum placentas, e.g., the isolated placental cells described in Section 5.4.2, above, can be cultured in a number of different ways to produce a set of lots, e.g., wherein a lot is a set of individually-administrable doses, of isolated placental cells. Such lots can, for example, be obtained from cells from placental perfusate or from cells from enzyme-digested placental tissue. Sets of lots of placental cells, obtained from a plurality of placentas, can be arranged in a bank of isolated placental cells for, e.g., long-term storage. Generally, tissue culture plastic-adherent placental cells are obtained from an initial culture of placental material to form a seed culture, which is expanded under controlled conditions to form populations of cells from approximately equivalent numbers of doublings. Lots are preferably derived from the tissue of a single placenta, but can be derived from the tissue of a plurality of placentas.

In one embodiment, placental cell lots are obtained as follows. Placental tissue is first disrupted, e.g., by mincing, digested with a suitable enzyme, e.g., trypsin or collagenase (see Section 5.5.3, above). The placental tissue preferably comprises, e.g., the entire amnion, entire chorion, or both, from a single placenta, but can comprise only a part of either the amnion or chorion. The digested tissue is cultured, e.g., for about 1-3 weeks, preferably about 2 weeks. After removal of non-adherent cells, high-density colonies that form are collected, e.g., by trypsinization. These cells are collected and resuspended in a convenient volume of culture medium, and are then used to seed expansion cultures. Expansion cultures can be any arrangement of separate cell culture apparatuses, e.g., a Cell Factory by NUNC™. Cells can be subdivided to any degree so as to seed expansion cultures with, e.g., $1 \times 10^3$, $2 \times 10^3$, $3 \times 10^3$, $4 \times 10^3$, $5 \times 10^3$, $6 \times 10^3$, $7 \times 10^3$, $8 \times 10^3$, $9 \times 10^3$, $1 \times 10^4$, $1 \times 10^4$ $2 \times 10^4$, $3 \times 10^4$, $4 \times 10^4$, $5 \times 10^4$, $6 \times 10^4$, $7 \times 10^4$, $8 \times 10^4$, $9 \times 10^4$ or $10 \times 10^4$ cells/cm². Preferably, from about $1 \times 10^3$ to about $1 \times 10^4$ cells/cm² are used to seed each expansion culture. The number of expansion cultures may be greater or fewer in number depending upon the particular placenta(s) from which the cells are obtained.

Expansion cultures are grown until the density of cells in culture reaches a certain value, e.g., about $1 \times 10^5$ cells/cm². Cells can either be collected and cryopreserved at this point, or passaged into new expansion cultures as described above. Cells can be passaged, e.g., 2, 3, 4, 5, 6, 7, 8, 9, 10, 11, 12, 13, 14, 15, 16, 17, 18, 19 or 20 times prior to use. A record of the cumulative number of population doublings is preferably maintained during expansion culture(s). The cells from a culture can be expanded for 2, 3, 4, 5, 6, 7, 8, 9, 10, 12, 14, 16, 18, 20, 22, 24, 26, 28, 30, 32, 34, 36, 38 or 40 doublings, or up to 60 doublings. Preferably, however, the number of population doublings, prior to dividing the population of cells into individual doses, is from about 15 to about 30. The cells can be culture continuously throughout the expansion process, or can be frozen at one or more points during expansion.

Cells to be used for individual doses can be frozen, e.g., cryopreserved for later use. Individual doses can comprise, e.g., about 1 million to about 50 million cells per ml, and can comprise between about $10^6$ and about $10^{10}$ cells in total.

In one embodiment, therefore, a placental cell bank can be made by a method comprising: expanding primary culture placental cells from a human post-partum placenta for a first plurality of population doublings; cryopreserving said placental cells to form a Master Cell Bank; expanding a plurality of placental cells from the Master Cell Bank for a second plurality of population doublings; cryopreserving said placental cells to form a Working Cell Bank; expanding a plurality of placental cells from the Working Cell Bank for a third plurality of population doublings; and cryopreserving said placental cells in individual doses, wherein said individual doses collectively compose a placental cell bank. Optionally, a plurality of placental cells from said third plurality of population doublings can be expanded for a fourth plurality of population doublings and cryopreserved in individual doses, wherein said individual doses collectively compose a placental stem cell bank.

In another specific embodiment, said primary culture placental cells comprise placental cells from placental perfusate. In another specific embodiment, said primary culture placental cells comprise placental cells from digested placental tissue. In another specific embodiment, said primary culture placental cells comprise placental cells from placental perfusate and from digested placental tissue. In another specific embodiment, all of said placental cells in said placental cell primary culture are from the same placenta. In another specific embodiment, the method further comprises the step of selecting $CD200^+$ or $HLA-G^+$ placental cells from said plurality of said placental cells from said Working Cell Bank to form individual doses. In another specific embodiment, said individual doses comprise from about $10^4$ to about $10^5$ placental cells. In another specific embodiment, said individual doses comprise from about $10^5$ to about $10^6$ placental cells. In another specific embodiment, said individual doses comprise from about $10^6$ to about $10^7$ placental cells. In another specific embodiment, said individual doses comprise from about $10^7$ to about $10^8$ placental cells. In another specific embodiment, said individual doses comprise from about $10^8$ to about $10^9$ placental cells. In another specific embodiment, said individual doses comprise from about $10^9$ to about $10^{10}$ placental cells.

In a preferred embodiment, the donor from which the placenta is obtained (e.g., the mother) is tested for at least one pathogen. If the mother tests positive for a tested pathogen, the entire lot from the placenta is discarded. Such testing can be performed at any time during production of placental cell lots, e.g., during expansion culture. Pathogens for which the presence is tested can include, without limitation, hepatitis A, hepatitis B, hepatitis C, hepatitis D, hepatitis E, human immunodeficiency virus (types I and II), cytomegalovirus, herpesvirus, and the like.

5.8 Preservation of Placental Cells

Isolated placental cells, e.g., the isolated placental cells described in Section 5.4.2, above, can be preserved, that is, placed under conditions that allow for long-term storage, or conditions that inhibit cell death by, e.g., apoptosis or necrosis.

Placental cells can be preserved using, e.g., a composition comprising an apoptosis inhibitor, necrosis inhibitor and/or an oxygen-carrying perfluorocarbon, as described in related U.S. Application Publication No. 2007/0190042, the disclosure of which is incorporated herein by reference in its entirety. In one embodiment, a method of preserving a population of cells, useful in the treatment of disruption of blood flow in or around the brain or CNS, comprises contacting said population of cells with a cell collection composition comprising an inhibitor of apoptosis and an oxygen-carrying perfluorocarbon, wherein said inhibitor of apoptosis is present in an amount and for a time sufficient to reduce or prevent apoptosis in the population of cells, as compared to a population of cells not contacted with the inhibitor of apoptosis. In a specific embodiment, said inhibitor of apoptosis is a caspase inhibitor. In another specific embodiment, said inhibitor of apoptosis is a JNK inhibitor. In a more specific embodiment, said JNK inhibitor does not modulate differentiation or proliferation of said cells. In another embodiment, said cell collection composition comprises said inhibitor of apoptosis and said oxygen-carrying perfluorocarbon in separate phases. In another embodiment, said cell collection composition comprises said inhibitor of apoptosis and said oxygen-carrying perfluorocarbon in an emulsion. In another embodiment, the cell collection composition additionally comprises an emulsifier, e.g., lecithin. In another embodiment, said apoptosis inhibitor and said perfluorocarbon are between about 0° C. and about 25° C. at the time of contacting the cells. In another more specific embodiment, said apoptosis inhibitor and said perfluorocarbon are between about 2° C. and 10° C., or between about 2° C. and about 5° C., at the time of contacting the cells. In another more specific embodiment, said contacting is performed during transport of said population of cells. In another more specific embodiment, said contacting is performed during freezing and thawing of said population of cells.

Populations of placental cells can be preserved, e.g., by a method comprising contacting said population of cells with an inhibitor of apoptosis and an organ-preserving compound, wherein said inhibitor of apoptosis is present in an amount and for a time sufficient to reduce or prevent apoptosis in the population of cells, as compared to a population of cells not contacted with the inhibitor of apoptosis. In a specific embodiment, the organ-preserving compound is UW solution (described in U.S. Pat. No. 4,798,824; also known as ViaSpan; see also Southard et al., Transplantation 49(2):251-257 (1990)) or a solution described in Stern et al., U.S. Pat. No. 5,552,267. In another embodiment, said organ-preserving compound is hydroxyethyl starch, lactobionic acid, raffinose, or a combination thereof. In another embodiment, the cell collection composition additionally comprises an oxygen-carrying perfluorocarbon, either in two phases or as an emulsion.

In another embodiment of the method, placental cells are contacted with a cell collection composition comprising an apoptosis inhibitor and oxygen-carrying perfluorocarbon, organ-preserving compound, or combination thereof, during perfusion. In another embodiment, said cells are contacted during a process of tissue disruption, e.g., enzymatic digestion. In another embodiment, placental cells are contacted with said cell collection compound after collection by perfusion, or after collection by tissue disruption, e.g., enzymatic digestion.

Typically, during placental cell collection, enrichment and isolation, it is preferable to minimize or eliminate cell stress due to hypoxia and mechanical stress. In another embodiment of the method, therefore, a cell, or population of cells, is exposed to a hypoxic condition during collection, enrichment or isolation for less than six hours during said preservation, wherein a hypoxic condition is a concentration of oxygen that is less than normal blood oxygen concentration. In a more specific embodiment, said population of cells is exposed to said hypoxic condition for less than two hours during said preservation. In another more specific embodiment, said population of cells is exposed to said hypoxic condition for less than one hour, or less than thirty minutes, or is not exposed to a hypoxic condition, during collection, enrichment or isolation. In another specific embodiment, said population of cells is not exposed to shear stress during collection, enrichment or isolation.

Placental cells can be cryopreserved, e.g., in cryopreservation medium in small containers, e.g., ampoules. Suitable cryopreservation medium includes, but is not limited to, culture medium including, e.g., growth medium, or cell freezing medium, for example commercially available cell freezing medium, e.g., C2695, C2639 or C6039 (Sigma). Cryopreservation medium preferably comprises DMSO (dimethylsulfoxide), at a concentration of about 2% to about 15% (v/v), e.g., about 10% (v/v). Cryopreservation medium may comprise additional agents, for example, methylcellulose and/or glycerol. Placental cells are preferably cooled at about 1° C./min during cryopreservation. A preferred cryopreservation temperature is about −80° C. to about −180° C., preferably about −125° C. to about −140° C. Cryopreserved cells can be transferred to liquid nitrogen prior to thawing for use. In some embodiments, for example, once the ampoules have reached about −90° C., they are transferred to a liquid nitrogen storage area. Cryopreservation can also be done using a controlled-rate freezer. Cryopreserved cells preferably are thawed at a temperature of about 25° C. to about 40° C., preferably to a temperature of about 37° C.

5.9 Compositions Comprising Isolated Placental Cells

The placental cells described herein, e.g., at Section 5.4.2, can be combined with any physiologically-acceptable or medically-acceptable compound, composition or device for use in the treatment of disruption of blood flow in or around the brain or CNS. Compositions useful in the methods of treatment provided herein can comprise any one or more of the placental cells described herein (see Section 5.4.2, above). In certain embodiments, the composition is a pharmaceutically-acceptable composition, e.g., a composition comprising placental cells in a pharmaceutically-acceptable carrier. See Section 5.9.2, below.

In certain embodiments, a composition comprising the isolated placental cells additionally comprises a matrix, e.g., a decellularized matrix or a synthetic matrix. In a more specific embodiment, said matrix is a three-dimensional scaffold. In another more specific embodiment, said matrix comprises collagen, gelatin, laminin, fibronectin, pectin, ornithine, or vitronectin. In another more specific embodiment, the matrix is an amniotic membrane or an amniotic membrane-derived biomaterial. In another more specific embodiment, said matrix comprises an extracellular membrane protein. In another more specific embodiment, said matrix comprises a synthetic compound. In another more specific embodiment, said matrix comprises a bioactive compound. In another more specific embodiment, said bioactive compound is a growth factor, cytokine, antibody, or organic molecule of less than 5,000 daltons.

In another embodiment, a composition useful in the methods of treatment provided herein comprises medium conditioned by any of the foregoing placental cells, or any of the foregoing placental cell populations.

5.9.1 Cryopreserved Isolated Placental Cells

The isolated placental cell populations useful for the treatment of disruption of blood flow in or around the brain or CNS can be preserved, for example, cryopreserved for later use. Methods for cryopreservation of cells, such as stem cells, are well known in the art. Isolated placental cell populations can be prepared in a form that is easily administrable to an individual, e.g., an isolated placental cell population that is contained within a container that is suitable for medical use. Such a container can be, for example, a syringe, sterile plastic bag, flask, jar, or other container from which the isolated placental cell population can be easily dispensed. For example, the container can be a blood bag or other plastic, medically-acceptable bag suitable for the intravenous administration of a liquid to a recipient. The container is preferably one that allows for cryopreservation of the combined cell population.

The cryopreserved isolated placental cell population can comprise isolated placental cell derived from a single donor, or from multiple donors. The isolated placental cell population can be completely HLA-matched to an intended recipient, or partially or completely HLA-mismatched.

Thus, in one embodiment, isolated placental cells can be used for the treatment of disruption of blood flow in or around the brain or CNS in the form of a composition comprising a tissue culture plastic-adherent placental cell population in a container. In a specific embodiment, the isolated placental cells are cryopreserved. In another specific embodiment, the container is a bag, flask, or jar. In more specific embodiment, said bag is a sterile plastic bag. In a more specific embodiment, said bag is suitable for, allows or facilitates intravenous administration of said isolated placental cell population, e.g., by intravenous infusion. The bag can comprise multiple lumens or compartments that are interconnected to allow mixing of the isolated placental cells and one or more other solutions, e.g., a drug, prior to, or during, administration. In another specific embodiment, the composition comprises one or more compounds that facilitate cryopreservation of the combined cell population. In another specific embodiment, said isolated placental cell population is contained within a physiologically-acceptable aqueous solution. In a more specific embodiment, said physiologically-acceptable aqueous solution is a 0.9% NaCl solution. In another specific embodiment, said isolated placental cell population comprises placental cells that are HLA-matched to a recipient of said cell population. In another specific embodiment, said combined cell population comprises placental cells that are at least partially HLA-mismatched to a recipient of said cell population. In another specific embodiment, said isolated placental cells are derived from a plurality of donors.

In certain embodiments, the isolated placental cells in the container are isolated $CD10^+$, $CD34^-$, $CD105^+$ placental cells, wherein said cells have been cryopreserved, and are contained within a container. In a specific embodiment, said $CD10^+$, $CD34^-$, $CD105^+$ placental cells are also $CD200^+$. In a more specific embodiment, said $CD10^+$, $CD34^-$, $CD105^+$, $CD200^+$ placental cells are also $CD45^-$ or $CD90^+$. In a more specific embodiment, said $CD10^+$, $CD34^-$, $CD105^+$, $CD200^+$ placental cells are also $CD45^-$ and $CD90^+$. In another specific embodiment, the $CD34^-$, $CD10^+$, $CD105^+$ placental cells are additionally one or more of $CD13^+$, $CD29^+$, $CD33^+$, $CD38^-$, $CD44^+$, $CD45^-$, $CD54^+$, $CD62E^-$, $CD62L^-$, $CD62P^-$, $SH3^+$ ($CD73^+$), $SH4^+$ ($CD73^+$), $CD80^-$, $CD86^-$, $CD90^+$, $SH2^+$ ($CD105^+$), $CD106/VCAM^+$, $CD117^-$, $CD144/VE$-$cadherin^{low}$, $CD184/CXCR4^-$, $CD200^+$, $CD133^-$, $OCT$-$4^+$, $SSEA3^-$, $SSEA4^-$, $ABC$-$p^+$, $KDR^-$ ($VEGFR2^-$), $HLA$-$A,B,C^+$, $HLA$-$DP,DQ,DR^-$, $HLA$-$G^+$, or Programmed Death-1 Ligand ($PDL1$)$^+$, or any combination thereof. In a more specific embodiment, the $CD34^-$, $CD10^+$, $CD105^+$ placental cells are additionally $CD13^+$, $CD29^+$, $CD33^+$, $CD38^-$, $CD44^+$, $CD45^-$, $CD54/ICAM^+$, $CD62E^-$, $CD62L^-$, $CD62P^-$, $SH3^+$ ($CD73^+$), $SH4^+$ ($CD73^+$), $CD80^-$, $CD86^-$, $CD90^+$, $SH2^+$ ($CD105^+$), $CD106/VCAM^+$, $CD117^-$, $CD144/VE$-$cadherin^{low}$, $CD184/CXCR4^-$, $CD200^+$, $CD133^-$, $OCT$-$4^+$, $SSEA3^-$, $SSEA4^-$, $ABC$-$p^+$, $KDR^-$ ($VEGFR2^-$), $HLA$-$A,B,C^+$, $HLA$-$DP,DQ,DR7$, $HLA$-$G^+$, and Programmed Death-1 Ligand ($PDL1$)$^+$.

In certain other embodiments, the above-referenced isolated placental cells are isolated $CD200^+$, $HLA$-$G^+$ placental cells, wherein said cells have been cryopreserved, and are contained within a container. In another embodiment, the isolated placental cells are $CD73^+$, $CD105^+$, $CD200^+$ cells that have been cryopreserved, and are contained within a container. In another embodiment, the isolated placental cells are $CD200^+$, $OCT$-$4^+$ stem cells that have been cryopreserved, and are contained within a container. In another embodiment, the isolated placental cells are $CD73^+$, $CD105^+$ cells that have been cryopreserved, and are contained within a container, and wherein said isolated placental cells facilitate the formation of one or more embryoid-like bodies when cultured with a population of placental cells under conditions that allow for the formation of embryoid-like bodies. In another embodiment, the isolated placental cells are $CD73^+$, $CD105^+$, $HLA$-$G^+$ cells that have been cryopreserved, and are contained within a container. In another embodiment, the isolated placental cells are $OCT$-$4^+$ placental cells that have been cryopreserved, and are contained within a container, and wherein said cells facilitate the formation of one or more embryoid-like bodies when cultured with a population of placental cells under conditions that allow for the formation of embryoid-like bodies.

In another specific embodiment, the above-referenced isolated placental cells are placental stem cells or placental multipotent cells that are $CD34^-$, $CD10^+$ and $CD105^+$ as detected by flow cytometry. In a more specific embodiment, the isolated $CD34^-$, $CD10^+$, $CD105^+$ placental cells are placental stem cells. In another more specific embodiment, the isolated $CD34^-$, $CD10^+$, $CD105^+$ placental cells are multipotent placental cells. In another specific embodiment, the isolated $CD34^-$, $CD10^+$, $CD105^+$ placental cells have the potential to differentiate into cells of a neural phenotype, cells of an osteogenic phenotype, or cells of a chondrogenic phenotype. In a more specific embodiment, the isolated $CD34^-$, $CD10^+$, $CD105^+$ placental cells are additionally $CD200^+$. In another more specific embodiment, the isolated $CD34^-$, $CD10^+$, $CD105^+$ placental cells are additionally $CD90^+$ or $CD45^-$, as detected by flow cytometry. In another more specific embodiment, the isolated $CD34^-$, $CD10^+$, $CD105^+$ placental cells are additionally $CD90^+$ or $CD45^-$, as detected by flow cytometry. In a more specific embodiment, the $CD34^-$, $CD10^+$, $CD105^+$, $CD200^+$ placental cells are additionally $CD90^+$ or $CD45$, as detected by flow cytometry. In another more specific embodiment, the $CD34^-$, $CD10^+$, $CD105^+$, $CD200^+$ cells are additionally $CD90^+$ and $CD45^-$, as detected by flow cytometry. In another more specific embodiment, the $CD34^-$, $CD10^+$, $CD105^+$, $CD200^+$, $CD90^+$, $CD45^-$ cells are additionally $CD80^-$ and $CD86^-$, as detected by flow cytometry. In another more specific embodiment, the $CD34^-$, $CD10^+$, $CD105^+$ cells are additionally one or more of CD29$^+$, CD38$^-$, CD44$^+$, CD54$^+$, CD80$^-$, CD86$^-$, SH3$^+$ or SH4$^+$. In another more specific embodiment, the cells are additionally CD44$^+$. In a specific embodiment of any of the isolated CD34$^-$, CD10$^+$, CD105$^+$ placental cells above, the cells are additionally one or more of CD117$^-$, CD133$^-$, KDR$^-$ (VEGFR2$^-$), HLA-A,B,C$^+$, HLA-DP,DQ,DR$^-$, and/or PDL1$^+$.

In a specific embodiment of any of the foregoing cryopreserved isolated placental cells, said container is a bag. In various specific embodiments, said container comprises about, at least, or at most $1\times10^6$ said isolated placental cells, $5\times10^6$ said isolated placental cells, $1\times10^7$ said isolated placental cells, $5\times10^7$ said isolated placental cells, $1\times10^8$ said isolated placental cells, $5\times10^8$ said isolated placental cells, $1\times10^9$ said isolated placental cells, $5\times10^9$ said isolated placental cells, $1\times10^{10}$ said isolated placental cells, or $1\times10^{10}$ said isolated placental cells. In other specific embodiments of any of the foregoing cryopreserved populations, said isolated placental cells have been passaged about, at least, or no more than 5 times, no more than 10 times, no more than 15 times, or no more than 20 times. In another specific embodiment of any of the foregoing cryopreserved isolated placental cells, said isolated placental cells have been expanded within said container.

5.9.2 Pharmaceutical Compositions

Populations of isolated placental cells, or populations of cells comprising the isolated placental cells, can be formulated into pharmaceutical compositions for use in vivo, e.g., in the methods of treatment provided herein. Such pharmaceutical compositions comprise a population of isolated placental cells, or a population of cells comprising isolated placental cells, in a pharmaceutically-acceptable carrier, e.g., a saline solution or other accepted physiologically-acceptable solution for in vivo administration. Pharmaceutical compositions comprising the isolated placental cells described herein can comprise any, or any combination, of the isolated placental cell populations, or isolated placental cells, described elsewhere herein. The pharmaceutical compositions can comprise fetal, maternal, or both fetal and maternal isolated placental cells. The pharmaceutical compositions provided herein can further comprise isolated placental cells obtained from a single individual or placenta, or from a plurality of individuals or placentae.

The pharmaceutical compositions provided herein can comprise any number of isolated placental cells. For example, a single unit dose of isolated placental cells can comprise, in various embodiments, about, at least, or no more than $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$ or more isolated placental cells.

The pharmaceutical compositions provided herein comprise populations of cells that comprise 50% viable cells or more (that is, at least 50% of the cells in the population are functional or living). Preferably, at least 60% of the cells in the population are viable. More preferably, at least 70%, 80%, 90%, 95%, or 99% of the cells in the population in the pharmaceutical composition are viable.

The pharmaceutical compositions provided herein can comprise one or more compounds that, e.g., facilitate engraftment (e.g., anti-T-cell receptor antibodies, an immunosuppressant, or the like); stabilizers such as albumin, dextran 40, gelatin, hydroxyethyl starch, plasmalyte, and the like.

When formulated as an injectable solution, in one embodiment, the pharmaceutical composition comprises about 1% to 1.5% HSA and about 2.5% dextran. In a preferred embodiment, the pharmaceutical composition comprises from about $5\times10^6$ cells per milliliter to about $2\times10^7$ cells per milliliter in a solution comprising 5% HSA and 10% dextran, optionally comprising an immunosuppressant, e.g., cyclosporine A at, e.g., 10 mg/kg.

In other embodiments, the pharmaceutical composition, e.g., a solution, comprises a plurality of cells, e.g., isolated placental cells, for example, placental stem cells or placental multipotent cells, wherein said pharmaceutical composition comprises between about $1.0\pm0.3\times10^6$ cells per milliliter to about $5.0\pm1.5\times10^6$ cells per milliliter. In other embodiments, the pharmaceutical composition comprises between about $1.5\times10^6$ cells per milliliter to about $3.75\times10^6$ cells per milliliter. In other embodiments, the pharmaceutical composition comprises between about $1\times10^6$ cells/mL to about $50\times10^6$ cells/mL, about $1\times10^6$ cells/mL to about $40\times10^6$ cells/mL, about $1\times10^6$ cells/mL to about $30\times10^6$ cells/mL, about $1\times10^6$ cells/mL to about $20\times10^6$ cells/mL, about $1\times10^6$ cells/mL to about $15\times10^6$ cells/mL, or about $1\times10^6$ cells/mL to about $10\times10^6$ cells/mL. In certain embodiments, the pharmaceutical composition comprises no visible cell clumps (i.e., no macro cell clumps), or substantially no such visible clumps. As used herein, "macro cell clumps" means an aggregation of cells visible without magnification, e.g., visible to the naked eye, and generally refers to a cell aggregation larger than about 150 microns In some embodiments, the pharmaceutical composition comprises about 2.5%, 3.0%, 3.5%, 4.0%, 4.5%, 5.0%, 5.5%, 6.0%, 6.5%, 7.0%, 7.5% 8.0%, 8.5%, 9.0%, 9.5% or 10% dextran, e.g., dextran-40. In a specific embodiment, said composition comprises about 7.5% to about 9% dextran-40. In a specific embodiment, said composition comprises about 5.5% dextran-40. In certain embodiments, the pharmaceutical composition comprises from about 1% to about 15% human serum albumin (HSA). In specific embodiments, the pharmaceutical composition comprises about 1%, 2%, 3%, 4%, 5%, 65, 75, 8%, 9%, 10%, 11%, 12%, 13%, 14% or 15% HSA. In a specific embodiment, said cells have been cryopreserved and thawed. In another specific embodiment, said cells have been filtered through a 70 μM to 100 μM filter. In another specific embodiment, said composition comprises no visible cell clumps. In another specific embodiment, said composition comprises fewer than about 200 cell clumps per $10^6$ cells, wherein said cell clumps are visible only under a microscope, e.g., a light microscope. In another specific embodiment, said composition comprises fewer than about 150 cell clumps per $10^6$ cells, wherein said cell clumps are visible only under a microscope, e.g., a light microscope. In another specific embodiment, said composition comprises fewer than about 100 cell clumps per $10^6$ cells, wherein said cell clumps are visible only under a microscope, e.g., a light microscope.

In a specific embodiment, the pharmaceutical composition comprises about $1.0\pm0.3\times10^6$ cells per milliliter, about 5.5% dextran-40 (w/v), about 10% HSA (w/v), and about 5% DMSO (v/v).

In other embodiments, the pharmaceutical composition comprises a plurality of cells, e.g., a plurality of isolated placental cells in a solution comprising 10% dextran-40, wherein the pharmaceutical composition comprises between about $1.0\pm0.3\times10^6$ cells per milliliter to about $5.0\pm1.5\times10^6$ cells per milliliter, and wherein said composition comprises no cell clumps visible with the unaided eye (i.e., comprises no macro cell clumps). In some embodiments, the pharmaceutical composition comprises between about $1.5\times10^6$ cells per milliliter to about $3.75\times10^6$ cells per milliliter. In a specific embodiment, said cells have been cryopreserved and thawed. In another specific embodiment, said cells have been filtered through a 70 μM to 100 μM filter. In another specific embodiment, said composition comprises fewer than about 200 micro cell clumps (that is, cell clumps visible only with magnification) per $10^6$ cells. In another specific embodiment, the pharmaceutical composition comprises fewer than about 150 micro cell clumps per $10^6$ cells. In another specific embodiment, the pharmaceutical composition comprises fewer than about 100 micro cell clumps per $10^6$ cells. In another specific embodiment, the pharmaceutical composition comprises less than 15%, 14%, 13%, 12%, 11%, 10%, 9%, 8%, 7%, 6%, 5%, 4%, 3%, or 2% DMSO, or less than 1%, 0.9%, 0.8%, 0.7%, 0.6%, 0.5%, 0.4%, 0.3%, 0.2%, or 0.1% DMSO.

Further provided herein are compositions comprising cells, wherein said compositions are produced by one of the methods disclosed herein. For example, in one embodiment, the pharmaceutical composition comprises cells, wherein the pharmaceutical composition is produced by a method comprising filtering a solution comprising placental cells, e.g., placental stem cells or placental multipotent cells, to form a filtered cell-containing solution; diluting the filtered cell-containing solution with a first solution to about 1 to $50 \times 10^6$, 1 to $40 \times 10^6$, 1 to $30 \times 10^6$, 1 to $20 \times 10^6$, 1 to $15 \times 10^6$, or 1 to $10 \times 10^6$ cells per milliliter, e.g., prior to cryopreservation; and diluting the resulting filtered cell-containing solution with a second solution comprising dextran, but not comprising human serum albumin (HSA) to produce said composition. In certain embodiments, said diluting is to no more than about $15 \times 10^6$ cells per milliliter. In certain embodiments, said diluting is to no more than about $10 \pm 3 \times 10^6$ cells per milliliter. In certain embodiments, said diluting is to no more than about $7.5 \times 10^6$ cells per milliliter. In other certain embodiments, if the filtered cell-containing solution, prior to the dilution, comprises less than about $15 \times 10^6$ cells per milliliter, filtration is optional. In other certain embodiments, if the filtered cell-containing solution, prior to the dilution, comprises less than about $10 \pm 3 \times 10^6$ cells per milliliter, filtration is optional. In other certain embodiments, if the filtered cell-containing solution, prior to the dilution, comprises less than about $7.5 \times 10^6$ cells per milliliter, filtration is optional.

In a specific embodiment, the cells are cryopreserved between said diluting with a first dilution solution and said diluting with said second dilution solution. In another specific embodiment, the first dilution solution comprises dextran and HSA. The dextran in the first dilution solution or second dilution solution can be dextran of any molecular weight, e.g., dextran having a molecular weight of from about 10 kDa to about 150 kDa. In some embodiments, said dextran in said first dilution solution or said second solution is about 2.5%, 3.0%, 3.5%, 4.0%, 4.5%, 5.0%, 5.5%, 6.0%, 6.5%, 7.0%, 7.5% 8.0%, 8.5%, 9.0%, 9.5% or 10% dextran. In another specific embodiment, the dextran in said first dilution solution or said second dilution solution is dextran-40. In another specific embodiment, the dextran in said first dilution solution and said second dilution solution is dextran-40. In another specific embodiment, said dextran-40 in said first dilution solution is 5.0% dextran-40. In another specific embodiment, said dextran-40 in said first dilution solution is 5.5% dextran-40. In another specific embodiment, said dextran-40 in said second dilution solution is 10% dextran-40. In another specific embodiment, said HSA in said solution comprising HSA is 1 to 15% HSA. In another specific embodiment, said HSA in said solution comprising HSA is about 1%, 2%, 3%, 4%, 5%, 6%, 7%, 8%, 9%, 10%, 11%, 12%, 13%, 14% or 15% HSA. In another specific embodiment, said HSA in said solution comprising HSA is 10% HSA. In another specific embodiment, said first dilution solution comprises HSA. In a more specific embodiment, said HSA in said first dilution solution is 10% HSA. In another specific embodiment, said first dilution solution comprises a cryoprotectant. In a more specific embodiment, said cryoprotectant is DMSO. In another specific embodiment, said dextran-40 in said second dilution solution is about 10% dextran-40. In another specific embodiment, said composition comprising cells comprises about 7.5% to about 9% dextran. In another specific embodiment, the pharmaceutical composition comprises from about $1.0 \pm 0.3 \times 10^6$ cells per milliliter to about $5.0 \pm 1.5 \times 10^6$ cells per milliliter. In another specific embodiment, the pharmaceutical composition comprises from about $1.5 \times 10^6$ cells per milliliter to about $3.75 \times 10^6$ cells per milliliter.

In another embodiment, the pharmaceutical composition is made by a method comprising (a) filtering a cell-containing solution comprising placental cells, e.g., placental stem cells or placental multipotent cells, prior to cryopreservation to produce a filtered cell-containing solution; (b) cryopreserving the cells in the filtered cell-containing solution at about 1 to $50 \times 10^6$, 1 to $40 \times 10^6$, 1 to $30 \times 10^6$, 1 to $20 \times 10^6$, 1 to $15 \times 10^6$, or 1 to $10 \times 10^6$ cells per milliliter; (c) thawing the cells; and (d) diluting the filtered cell-containing solution about 1:1 to about 1:11 (v/v) with a dextran-40 solution. In certain embodiments, if the number of cells is less than about $10 \pm 3 \times 10^6$ cells per milliliter prior to step (a), filtration is optional. In a more specific embodiment, the cells in step (b) are cryopreserved at about $10 \pm 3 \times 10^6$ cells per milliliter. In a more specific embodiment, the cells in step (b) are cryopreserved in a solution comprising about 5% to about 10% dextran-40 and HSA. In certain embodiments, said diluting in step (b) is to no more than about $15 \times 10^6$ cells per milliliter.

In another embodiment, the pharmaceutical composition is made by a method comprising: (a) suspending placental cells, e.g., placental stem cells or placental multipotent cells, in a 5.5% dextran-40 solution that comprises 10% HSA to form a cell-containing solution; (b) filtering the cell-containing solution through a 70 μM filter; (c) diluting the cell-containing solution with a solution comprising 5.5% dextran-40, 10% HSA, and 5% DMSO to about 1 to $50 \times 10^6$, 1 to $40 \times 10^6$, 1 to $30 \times 10^6$, 1 to $20 \times 10^6$, 1 to $15 \times 10^6$, or 1 to $10 \times 10^6$ cells per milliliter; (d) cryopreserving the cells; (e) thawing the cells; and (f) diluting the cell-containing solution 1:1 to 1:11 (v/v) with 10% dextran-40. In certain embodiments, said diluting in step (c) is to no more than about $15 \times 10^6$ cells per milliliter. In certain embodiments, said diluting in step (c) is to no more than about $10 \pm 3 \times 10^6$ cells/mL. In certain embodiments, said diluting in step (c) is to no more than about $7.5 \times 10^6$ cells/mL.

In another embodiment, the composition comprising cells is made by a method comprising: (a) centrifuging a plurality of cells to collect the cells; (b) resuspending the cells in 5.5% dextran-40; (c) centrifuging the cells to collect the cells; (d) resuspending the cells in a 5.5% dextran-40 solution that comprises 10% HSA; (e) filtering the cells through a 70 μM filter; (f) diluting the cells in 5.5% dextran-40, 10% HSA, and 5% DMSO to about 1 to $50 \times 10^6$, 1 to $40 \times 10^6$, 1 to $30 \times 10^6$, 1 to $20 \times 10^6$, 1 to $15 \times 10^6$, or 1 to $10 \times 10^6$ cells per milliliter; (g) cryopreserving the cells; (h) thawing the cells; and (i) diluting the cells 1:1 to 1:11 (v/v) with 10% dextran-40. In certain embodiments, said diluting in step (f) is to no more than about $15 \times 10^6$ cells per milliliter. In certain embodiments, said diluting in step (f) is to no more than about $10 \pm 3 \times 10^6$ cells/mL. In certain embodiments, said diluting in step (f) is to no more than about $7.5 \times 10^6$ cells/mL. In other certain embodiments, if the number of cells is less than about $10 \pm 3 \times 10^6$ cells per milliliter, filtration is optional.

The compositions, e.g., pharmaceutical compositions comprising the isolated placental cells, described herein can comprise any of the isolated placental cells described herein.

Other injectable formulations, suitable for the administration of cellular products, may be used.

In one embodiment, the pharmaceutical composition comprises isolated placental cells that are substantially, or completely, non-maternal in origin, that is, have the fetal genotype; e.g., at least about 90%, 95%, 98%, 99% or about 100% are non-maternal in origin. For example, in one embodiment a pharmaceutical composition comprises a population of isolated placental cells that are $CD200^+$ and $HLA-G^+$; $CD73^+$, $CD105^+$, and $CD200^+$; $CD200^+$ and $OCT-4^+$; $CD73^+$, $CD105^+$ and $HLA-G^+$; $CD73^+$ and $CD105^+$ and facilitate the formation of one or more embryoid-like bodies in a population of placental cells comprising said population of isolated placental cell when said population of placental cells is cultured under conditions that allow the formation of an embryoid-like body; or $OCT-4^+$ and facilitate the formation of one or more embryoid-like bodies in a population of placental cells comprising said population of isolated placental cell when said population of placental cells is cultured under conditions that allow the formation of an embryoid-like body; or a combination of the foregoing, wherein at least 70%, 80%, 90%, 95% or 99% of said isolated placental cells are non-maternal in origin. In another embodiment, a pharmaceutical composition comprises a population of isolated placental cells that are $CD10^+$, $CD105^+$ and $CD34^-$; $CD10^+$, $CD105^+$, $CD200^+$ and $CD34^-$; $CD10^+$, $CD105^+$, $CD200^+$, $CD34^-$ and at least one of $CD90^+$ or $CD45^-$; $CD10^+$, $CD90^+$, $CD105^+$, $CD200^+$, $CD34^-$ and $CD45^-$; $CD10^+$, $CD90^+$, $CD105^+$, $CD200^+$, $CD34^-$ and $CD45^-$; $CD200^+$ and $HLA-G^+$; $CD73^+$, $CD105^+$, and $CD200^+$; $CD200^+$ and $OCT-4^+$; $CD73^+$, $CD105^+$ and $HLA-G^+$; $CD73^+$ and $CD105^+$ and facilitate the formation of one or more embryoid-like bodies in a population of placental cells comprising said isolated placental cells when said population of placental cells is cultured under conditions that allow the formation of an embryoid-like body; $OCT-4^+$ and facilitate the formation of one or more embryoid-like bodies in a population of placental cells comprising said isolated placental cells when said population of placental cells is cultured under conditions that allow the formation of an embryoid-like body; or one or more of $CD117^-$, $CD133^-$, $KDR^-$, $CD80^-$, $CD86^-$, $HLA-A,B,C^+$, $HLA-DP,DQ,DR^-$ and/or $PDL1^+$; or a combination of the foregoing, wherein at least 70%, 80%, 90%, 95% or 99% of said isolated placental cells are non-maternal in origin. In a specific embodiment, the pharmaceutical composition additionally comprises a stem cell that is not obtained from a placenta.

Isolated placental cells in the compositions, e.g., pharmaceutical compositions, provided herein, can comprise placental cells derived from a single donor, or from multiple donors. The isolated placental cells can be completely HLA-matched to an intended recipient, or partially or completely HLA-mismatched.

5.9.3 Matrices Comprising Isolated Placental Cells

Further provided herein are compositions comprising matrices, hydrogels, scaffolds, and the like that comprise a placental stem cell, or a population of isolated placental cells. Such compositions can be used in the place of, or in addition to, cells in liquid suspension for the treatment of disruption of blood flow in or around the brain or CNS.

The isolated placental cells described herein can be seeded onto a natural matrix, e.g., a placental biomaterial such as an amniotic membrane material. Such an amniotic membrane material can be, e.g., amniotic membrane dissected directly from a mammalian placenta; fixed or heat-treated amniotic membrane, substantially dry (i.e., <20% $H_2O$) amniotic membrane, chorionic membrane, substantially dry chorionic membrane, substantially dry amniotic and chorionic membrane, and the like. Preferred placental biomaterials on which isolated placental cells can be seeded are described in Hariri, U.S. Application Publication No. 2004/0048796, the disclosure of which is incorporated herein by reference in its entirety.

The isolated placental cells described herein can be suspended in a hydrogel solution suitable for, e.g., injection. Suitable hydrogels for such compositions include self-assembling peptides, such as RAD16. In one embodiment, a hydrogel solution comprising the cells can be allowed to harden, for instance in a mold, to form a matrix having cells dispersed therein for implantation. Isolated placental cells in such a matrix can also be cultured so that the cells are mitotically expanded prior to implantation. The hydrogel is, e.g., an organic polymer (natural or synthetic) that is cross-linked via covalent, ionic, or hydrogen bonds to create a three-dimensional open-lattice structure that entraps water molecules to form a gel. Hydrogel-forming materials include polysaccharides such as alginate and salts thereof, peptides, polyphosphazines, and polyacrylates, which are crosslinked ionically, or block polymers such as polyethylene oxide-polypropylene glycol block copolymers which are crosslinked by temperature or pH, respectively. In some embodiments, the hydrogel or matrix is biodegradable.

In some embodiments, the formulation comprises an in situ polymerizable gel (see., e.g., U.S. Patent Application Publication 2002/0022676, the disclosure of which is incorporated herein by reference in its entirety; Anseth et al., *J. Control Release,* 78(1-3):199-209 (2002); Wang et al., *Biomaterials,* 24(22):3969-80 (2003).

In some embodiments, the polymers are at least partially soluble in aqueous solutions, such as water, buffered salt solutions, or aqueous alcohol solutions, that have charged side groups, or a monovalent ionic salt thereof. Examples of polymers having acidic side groups that can be reacted with cations are poly(phosphazenes), poly(acrylic acids), poly (methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups.

The isolated placental cells described herein or co-cultures thereof can be seeded onto a three-dimensional framework or scaffold and implanted in vivo. Such a framework can be implanted in combination with any one or more growth factors, cells, drugs or other components that, e.g., stimulate tissue formation.

Examples of scaffolds that can be used include nonwoven mats, porous foams, or self assembling peptides. Nonwoven mats can be formed using fibers comprised of a synthetic absorbable copolymer of glycolic and lactic acids (e.g., PGA/PLA) (VICRYL, Ethicon, Inc., Somerville, N.J.). Foams, composed of, e.g., poly(ε-caprolactone)/poly(glycolic acid) (PCL/PGA) copolymer, formed by processes such as freeze-drying, or lyophilization (see, e.g., U.S. Pat. No. 6,355,699), can also be used as scaffolds.

In another embodiment, isolated placental cells can be seeded onto, or contacted with, a felt, which can be, e.g., composed of a multifilament yarn made from a bioabsorbable material such as PGA, PLA, PCL copolymers or blends, or hyaluronic acid.

The isolated placental cells provided herein can, in another embodiment, be seeded onto foam scaffolds that may be composite structures. Such foam scaffolds can be molded into a useful shape, such as that of a portion of a specific structure in the body to be repaired, replaced or augmented. In some embodiments, the framework is treated, e.g., with 0.1M acetic acid followed by incubation in polylysine, PBS, and/or collagen, prior to inoculation of the cells in order to enhance cell attachment. External surfaces of a matrix may be modified to improve the attachment or growth of cells and differentiation of tissue, such as by plasma-coating the matrix, or addition of one or more proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate, etc.), a cellular matrix, and/or other materials such as, but not limited to, gelatin, alginates, agar, agarose, and plant gums, and the like.

In some embodiments, the scaffold comprises, or is treated with, materials that render it non-thrombogenic. These treatments and materials may also promote and sustain endothelial growth, migration, and extracellular matrix deposition. Examples of these materials and treatments include but are not limited to natural materials such as basement membrane proteins such as laminin and Type IV collagen, synthetic materials such as EPTFE, and segmented polyurethaneurea silicones, such as PURSPAN (The Polymer Technology Group, Inc., Berkeley, Calif.). The scaffold can also comprise anti-thrombotic agents such as heparin; the scaffolds can also be treated to alter the surface charge (e.g., coating with plasma) prior to seeding with isolated placental cells.

In one embodiment, the isolated placental cells are seeded onto, or contacted with, a suitable scaffold at about $0.5 \times 10^6$ to about $8 \times 10^6$ cells/mL.

5.10 Immortalized Placental Cell Lines

Mammalian placental cells can be conditionally immortalized by transfection with any suitable vector containing a growth-promoting gene, that is, a gene encoding a protein that, under appropriate conditions, promotes growth of the transfected cell, such that the production and/or activity of the growth-promoting protein is regulatable by an external factor. In a preferred embodiment the growth-promoting gene is an oncogene such as, but not limited to, v-myc, N-myc, c-myc, p53, SV40 large T antigen, polyoma large T antigen, E1a adenovirus or E7 protein of human papillomavirus.

External regulation of the growth-promoting protein can be achieved by placing the growth-promoting gene under the control of an externally-regulatable promoter, e.g., a promoter the activity of which can be controlled by, for example, modifying the temperature of the transfected cells or the composition of the medium in contact with the cells. in one embodiment, a tetracycline (tet)-controlled gene expression system can be employed (see Gossen et al., *Proc. Natl. Acad. Sci. USA* 89:5547-5551, 1992; Hoshimaru et al., *Proc. Natl. Acad. Sci. USA* 93:1518-1523, 1996). In the absence of tet, a tet-controlled transactivator (tTA) within this vector strongly activates transcription from $ph_{CMV*-1}$, a minimal promoter from human cytomegalovirus fused to tet operator sequences. tTA is a fusion protein of the repressor (tetR) of the transposon-10-derived tet resistance operon of *Escherichia coli* and the acidic domain of VP16 of herpes simplex virus. Low, non-toxic concentrations of tet (e.g., 0.01-1.0 µg/mL) almost completely abolish transactivation by tTA.

In one embodiment, the vector further contains a gene encoding a selectable marker, e.g., a protein that confers drug resistance. The bacterial neomycin resistance gene (neoR) is one such marker that may be employed within the present methods. Cells carrying neoR may be selected by means known to those of ordinary skill in the art, such as the addition of, e.g., 100-200 µg/mL G418 to the growth medium.

Transfection can be achieved by any of a variety of means known to those of ordinary skill in the art including, but not limited to, retroviral infection. In general, a cell culture may be transfected by incubation with a mixture of conditioned medium collected from the producer cell line for the vector and DMEM/F12 containing N2 supplements. For example, a placental cell culture prepared as described above may be infected after, e.g., five days in vitro by incubation for about 20 hours in one volume of conditioned medium and two volumes of DMEM/F12 containing N2 supplements. Transfected cells carrying a selectable marker may then be selected as described above.

Following transfection, cultures are passaged onto a surface that permits proliferation, e.g., allows at least 30% of the cells to double in a 24 hour period. Preferably, the substrate is a polyornithine/laminin substrate, consisting of tissue culture plastic coated with polyomithine (10 µg/mL) and/or laminin (10 µg/mL), a polylysine/laminin substrate or a surface treated with fibronectin. Cultures are then fed every 3-4 days with growth medium, which may or may not be supplemented with one or more proliferation-enhancing factors. Proliferation-enhancing factors may be added to the growth medium when cultures are less than 50% confluent.

The conditionally-immortalized placental cell lines can be passaged using standard techniques, such as by trypsinization, when 80-95% confluent. Up to approximately the twentieth passage, it is, in some embodiments, beneficial to maintain selection (by, for example, the addition of G418 for cells containing a neomycin resistance gene). Cells may also be frozen in liquid nitrogen for long-term storage.

Clonal cell lines can be isolated from a conditionally-immortalized human placental cell line prepared as described above. In general, such clonal cell lines may be isolated using standard techniques, such as by limit dilution or using cloning rings, and expanded. Clonal cell lines may generally be fed and passaged as described above.

Conditionally-immortalized human placental cell lines, which may, but need not, be clonal, may generally be induced to differentiate by suppressing the production and/or activity of the growth-promoting protein under culture conditions that facilitate differentiation. For example, if the gene encoding the growth-promoting protein is under the control of an externally-regulatable promoter, the conditions, e.g., temperature or composition of medium, may be modified to suppress transcription of the growth-promoting gene. For the tetracycline-controlled gene expression system discussed above, differentiation can be achieved by the addition of tetracycline to suppress transcription of the growth-promoting gene. In general, 1 µg/mL tetracycline for 4-5 days is sufficient to initiate differentiation. To promote further differentiation, additional agents may be included in the growth medium.

5.11 Kits

In another aspect, provided herein are kits, suitable for the treatment of an individual who has had a disruption of blood flow in or around the CNS, e.g., an individual who has had a stroke, comprising, in a container separate from remaining kit contents, tissue culture plastic adherent multipotent placental cells, e.g., placental stem cells or placental multipotent cells, and isolated populations thereof, e.g., the cells described in Section 5.4.2, above, and instructions for use. Preferably, the placental stem cells are provided in a pharmaceutically-acceptable solution, e.g., a solution suitable for intracranial administration or a solution suitable for intravenous administration. In certain embodiments, the placental stem cells or placental multipotent cells are any of the $CD10^+$, $CD34^-$, $CD105^+$ placental cells described herein, e.g., $CD10^+$, $CD34^-$, $CD105^+$, $CD200^+$ placental cells.

In certain embodiments, the kits comprise one or more components that facilitate delivery of the placental cells to the individual. For example, in certain embodiments, the kit comprises components that facilitate intracranial delivery of the placental cells to the individual. In such embodiments, the kit can comprise, e.g., syringes and needles suitable for delivery of cells to the individual; radioactive or non-radioactive compounds that enable visualization of affected CNS tissue (e.g., cobalt 55), and the like. In such embodiments, the placental cells may be contained in the kit in a bag, or in one or more vials. In certain other embodiments, the kit comprises components that facilitate intravenous or intra-arterial delivery of the placental cells to the individual. In such embodiments, the placental cells may be contained, e.g., within a bottle or bag (for example, a blood bag or similar bag able to contain up to about 1.5 L solution comprising the cells), and the kit additionally comprises tubing and needles suitable for the delivery of cells to the individual.

Additionally, the kit may comprise one or more compounds that reduce pain or inflammation in the individual (e.g., an analgesic, steroidal or non-steroidal anti-inflammatory compound, or the like. The kit may also comprise an antibacterial or antiviral compound (e.g., one or more antibiotics), a compound to reduce anxiety in the individual (e.g., alaprazolam), a compound that reduces an immune response in the individual (e.g., cyclosporine A), an antihistamine (diphenhydramine, loratadine, desloratadine, quetiapine, fexofenadine, cetirizine, promethazine, chlorepheniramine, levocetirizine, cimetidine, famotidine, ranitidine, nizatidine, roxatidine, lafutidine, or the like).

Additionally, the kit can comprise disposables, e.g., sterile wipes, disposable paper goods, gloves, or the like, which facilitate preparation of the individual for delivery, or which reduce the likelihood of infection in the individual as a result of the administration of the placental cells.

6. EXAMPLES

6.1 Example 1

Treatment of Stroke Using Isolated Placental Cells Administered Intracranially

This Example demonstrates the efficacy of administration of isolated placental cells, administered, in the treatment of symptoms associated with disruption of blood flow in or around the brain or CNS.

$CD34^-$, $CD10^+$, $CD105^+$, $CD200^+$ tissue culture plastic-adherent placental cells were obtained by enzymatic digestion using collagenase I at about 1 to about 2 mg/ml for, e.g., 30 minutes, followed by digestion with trypsin at a concentration of about 0.25%, for 10 minutes at 37° C. Sprague-Dawley rats were used as a stroke model. Rats are an established model animal in which to study the effects of stroke and the effects of various therapies on stroke symptoms. See, e.g., Chen et al., "A Model of Focal Ischemic Stroke in the Rat: Reproducible Extensive Cortical Infarction," *Stroke* 17(4): 738-743 (1986). 10 animals were used per condition.

MCA Stroke Surgery: All surgical procedures were conducted under aseptic conditions. Animals were anesthetized with equithesin (300 mg/kg, intraperitoneally) and checked for pain reflexes. The MCA occlusion surgery was performed on the animals under deep anesthesia. The MCA suture technique involves insertion of a filament through the carotid artery to reach the junction of the MCA, thus blocking the blood flow from the common carotid artery, as well as from the circle of Willis. The right common carotid artery was identified and isolated through a ventral midline cervical incision. The suture size was 4-0, made of sterile, non-absorbable suture (Ethicon, Inc., Somerville, N.J.), with the diameter of the suture tip tapered to 24 to 26-gauge size using a rubber cement. About 15 to 17 mm of the filament was inserted from the junction of the external and internal carotid arteries to block the MCA. The right MCA was occluded for one hour. Based on published studies, a one-hour occlusion of the MCA results in maximal infarction. See Borlongan et al., *Neurorep.* 9(16):3615-3621 (1998); Borlongan et al., *Pharmacol. Biochem. Behav.* 52(1):225-229 (1995); Borlongan et al., *Physiol Behav.* 58(5):909-917 (1995). A heating pad and a rectal thermometer were used to maintain body temperature within normal limits. To determine successful occlusion and reperfusion, a laser Doppler was used. The laser Doppler probe was placed at the distal end of the MCA to measure cerebral blood flow before, during and after occlusion.

The adherent placental cells were administered by intracranial injection (approximately 400,000 cells in 5 microliters) directly to the ischemic site at 2 days post-ischemia. Rats were administered vehicle (10% dextran and 5% human serum albumin) alone, $4 \times 10^5$ viable cells, $4 \times 10^5$ viable cells in conjunction with 10 mg/kg cyclosporine A, or $4 \times 10^5$ non-viable cells and cyclosporine A.

On days 7 and 14 post-ischemia, the animals were assayed for stroke induced motor asymmetry. Motor asymmetry was assessed using the Elevated Body Swing Test (EBST) or Bederson Test. See Borlongan & Sanberg, *J Neurosci* 15(7): 5372-5378 (1995). In the EBST, the animal was elevated by handling its tail, and the frequency and direction of the swing behavior was recorded. Rats were placed into a Plexiglass box and allowed to habituate for about 2 minutes. Rats were held at approximately 1 inch from the base of the tail, such that the rats' nose was approximately 1 inch from a surface. The rats were held to a vertical axis, or neutral position, defined as no more than 10° swing of the head to the right or left. A swing was recorded whenever the rat moved its head out of the vertical axis to the right or left; right swings or left swings were counted when the head of the animal moved 10° or more from the vertical axis right or left, respectively. Where the rat redoubled its efforts to a particular side, only a single swing was recorded. After a single swing, the animal was placed back in the Plexiglass box and allowed to move freely for 30 seconds prior to retesting. These steps were repeated 20 times for each animal (10 animals per condition).

The total number of swings was counted, as was the number of right and left swings. Swing behavior was deemed to be biased when the number of swings equaled or exceeded 70%. Results were analyzed using a two-way analysis of variance (ANOVA), and post hoc tests were carried out using the Tukey HSD (honestly significant difference) test.

Placental cell-induced repair of neurological deficits in rats was also assessed using the Bederson Neurological Test, which measures sensorimotor tasks. See Bederson et al., *Stroke* 17:472-6 (1986); Altumbabic, *Stroke* 29:1917-22 (1998).

For the Bederson Test, a neurologic score for each rat was obtained using 4 tests that include: (a) observation of spontaneous ipsilateral circling, graded from 0 (no circling) to 3 (continuous circling); (b) contralateral hindlimb retraction, which measures the ability of the animal to replace the hindlimb after it is displaced laterally by 2 to 3 cm, graded from 0 (immediate replacement) to 3 (replacement after minutes or no replacement); (c) beam walking ability, graded 0 for a rat that readily traverses a 2.4-cm-wide, 80-cm-long beam to 3 for a rat unable to stay on the beam for 10 seconds; and (d) bilateral forepaw grasp, which measures the ability to hold onto a 2-mm-diameter steel rod, graded 0 for a rat with normal forepaw grasping behavior to 3 for a rat unable to grasp with the forepaws. The scores from all 4 tests, performed over a period of about 15 minutes on assessment days 7 and 14, were added to give a neurologic deficit score from 0 to 12, with lower scores indicating more neurologically normal rats.

Results

At Day 0, immediately prior to induction of ischemia, all animals displayed approximately normal (unbiased) swing behavior (FIG. 1, Baseline). At day 2 post-ischemia, the day of placental cell administration, all animals displayed nearly 100% ischemia-induced bias in swing behavior (FIG. 1), as expected. At Day 7 and Day 14, animals receiving viable placental cells showed significant improvement, demonstrating approximately 65% and 60% swing bias, respectively (FIG. 1, Day 7 and Day 14). Animals receiving nonviable placental cells and cyclosporine A, or vehicle alone, showed no statistically significant improvement.

Rats evaluated at Day 0, prior to induction of ischemia, were all neurologically normal, and were given a deficit score of zero (FIG. 2, Baseline) in the Bederson test. At day two after induction of ischemia, the day isolated placental cells were administered, rats receiving only vehicle showed an aggregate mean deficit score of approximately 2.5 (FIG. 2, Day 2). By Days 7 and 14, rats receiving placental cells showed statistically significant improvement in the neurological deficit score, improving from a score of approximately 2.5 to a score of about 1.7 and 1.1, respectively. As with the EBST, rats receiving only vehicle or nonviable placental cells and cyclosporine A showed no statistically significant improvement in the neurologic deficit score.

In conclusion, it was demonstrated by two tests of neurological deficit that administration of $4 \times 10^5$ human placental cells at two days after the induction of ischemia in an accepted animal model of ischemia significantly improves neurological function in the model animals. Administration of cyclosporine A, to suppress any host immune reaction to the placental cells, did not appear to be necessary for neurological improvement due to the placental cells.

6.2 Example 2

Treatment of Stroke Using Isolated Placental Cells Administered Intravenously

This Example demonstrates the efficacy of administration of isolated placental cells, administered intravenously, in the treatment of symptoms associated with disruption of blood flow in or around the brain or CNS, e.g., of hypoxic injury or anoxic injury. For example, the results presented herein indicate that intravenous administration of placental cells promotes dose-dependent behavioral recovery in both motor and neurologic tests in animals administered viable human placental cells compared to animals receiving non-viable human placental cells.

Isolated CD34$^-$, CD10$^+$, CD105$^+$, CD200$^+$ tissue culture plastic-adherent placental cells were obtained by enzymatic digestion, as described elsewhere herein. Sprague-Dawley rats were used as a stroke model, and middle artery occlusion was performed as described in Example 1, above. On Day 2 post-occlusion, the subject rats were administered $4 \times 10^5$, $1 \times 10^6$, $4 \times 10^6$ or $8 \times 10^6$ placental cells in approximately 5 µL vehicle (10% dextran and 5% human serum albumin), or nonviable cells in vehicle as a control. Rats were evaluated at day 0 prior to surgery, and at days 2, 14, 28, 56 and 84 post-surgery by the Elevated Body Swing Test (EBST), as described in Example 1, above. A modified Bederson Test was performed, in which the subject rats were evaluated for (1) forelimb retraction, which measured the ability of the animal to replace the forelimb after it was displaced laterally by 2 to 3 cm, graded from 0 (immediate replacement) to 3 (replacement after several seconds or no replacement); (2) beam walking ability, graded 0 for a rat that readily traversed a 2.4-cm-wide, 80-cm-long beam to 3 for a rat unable to stay on the beam for 10 seconds; and (3) bilateral forepaw grasp, which measured the ability to hold onto a 2-mm-diameter steel rod, graded 0 for a rat with normal forepaw grasping behavior to 3 for a rat unable to grasp with the forepaws. The scores from all 3 tests, which were done over a period of about 15 minutes on each assessment day, were added to give a mean neurologic deficit score (maximum possible score, 9 points divided by 3 tests=3). Results of the EBST and Bederson tests were evaluated by two-way analysis of variance (ANOVA) Tukey HSD test as described in Example 1, above.

Rats were killed on Day 84 for necropsy and evaluation of engraftment and differentiation of the placental cells. Briefly, 20 µm cryostat sectioned tissues were examined at 40× magnification and digitized using a PC-based Image Tools computer program. Brain sections were blind-coded. Tissues sections were processed using standard ABC method. Cell engraftment and differentiation indices for human placenta-derived stem cell graft survival were assessed using the human specific antibody HuNu, which does not cross react with rodent cell surface markers or other rodent proteins. To detect expression of neuronal phenotype in cell grafts, immunohistochemical analysis using the neuronal marker MAP2 was used. Additional brain sections were processed for GFAP and O4 to reveal glial and oligodendroglial phenotypic expression of transplanted cells.

Intravenous transplantation of human placenta-derived cells did not require immunosuppression.

All animals included in this study displayed normal behaviors at baseline, and reached the criteria of successful cerebral ischemia induction at day 2 post-stroke prior to transplantation. Starting at the earliest time point of post-transplantation testing at post-stroke day 7, behavioral tests revealed a dose-dependent significant improvement in both locomotor and neurological functions in stroke animals that received viable human placenta-derived cells compared to stroke animals that received non-viable human placenta-derived cells. Over time up to 84 days post-stroke, there was an increasing trend in further improvement in both tasks in stroke animals that received viable human placenta-derived cells. There was no detectable exacerbation of stroke-induced behavioral deficits in any of the transplanted animals, including those that received non-viable cells. During the transplant maturation period, there was a general trend of spontaneous behavioral recovery in those that received non-viable cells, but this non-specific, non-transplant-mediated functional improvement did not reach statistical significance compared to pre-transplantation surgery (i.e., day 2 post-stroke).

Stroke animals that received the high dose of 8 million viable cells clearly exhibited the most robust improvement in both locomotor and neurological task as the early post-transplantation period. However, over time the stroke animals that received lower doses of viable cells also displayed profound attenuation of behavioral deficits which are generally comparable with the high dose of 8 million viable cells.

Rats evaluated at Day 0, prior to induction of ischemia, were all neurologically normal, and were given a deficit score of zero (FIG. 3, Baseline). At day 2 post-ischemia, the day of placental stem cell administration, all animals displayed nearly 100% ischemia-induced bias in swing behavior (FIG. 3), as expected. Animals receiving viable isolated placental cells showed significant, dose-dependent improvement in the EBST for each of Days 7, 14, 28, 56 and 84, as compared to control, and additionally showed significant improvement ($p<0.01$) between doses, with the exception of $4\times10^6$ vs. $8\times10^6$ isolated placental cells for all days, and $4\times10^5\times1\times10^6$ isolated placental cells at Day 7 ($p=0.0454$). See FIG. 3. Animals receiving nonviable isolated placental cells showed no statistically significant improvement compared to controls.

For the Bederson test, rats evaluated at Day 0, prior to induction of ischemia, were all neurologically normal, and were given a deficit score of zero (FIG. 4, Baseline). At day two after induction of ischemia, the day the isolated placental cells were administered, rats receiving only non-viable cells showed an aggregate mean deficit score of approximately 2.5-3.0 (FIG. 2, Day 2). At Days 7, 14, 28, 56 and 84, rats receiving the isolated placental cells showed statistically significant improvement in the neurological deficit score compared to rats receiving nonviable cells ($p<0.01$ in each case). Improvement was additionally significantly ($p<0.01$) dose-dependent at Day 7 ($4\times10^5$ vs. $8\times10^6$ and $1\times10^6$ vs. $8\times10^6$), and Days 14 and 28 ($4\times10^5$ vs. $4\times10^6$ and $4\times10^5$ vs. $8\times10^6$), respectively. As with the EBST, rats receiving only vehicle or nonviable isolated placental cells and cyclosporine A showed no statistically significant improvement in the neurologic deficit score.

Thus, intravenous administration of isolated placental cells promotes dose-dependent behavioral recovery in both motor and neurological tests. Functional improvement was evident as early as 7 days post-administration, with an increasing trend of better recovery over the 3 month post-transplant period. No overt adverse behavioral side effects were observed in any of the subject rats.

Thus, the results presented herein demonstrate the safety and efficacy of intravenous administration of isolated placental cells for treatment of symptoms associated with disruptions of blood flow in or around the brain. For example, none of the transplanted animals show any exacerbation of stroke-induced behavioral abnormalities. Compared to animals receiving non-viable human placenta-derived cells, those that received viable cells displayed significant improvement in stroke-induced behavioral deficits and significant rescue of host cells in the ischemic penumbra. Moreover, no tumors or ectopic tissue formation were detected in any of the transplanted animals.

6.3 Example 3

Treatment of Stroke Using Placental Cells Via Intravenous Route—Assessment by other Neurological Tests This Example demonstrates the effectiveness of treating stroke using placental stem cells, as assessed by neurological tests other than the elevated swing test and Bederson test.

6.3.1 Neurological Tests

Middle cerebral artery occlusion surgery was performed on Wistar rats as follows. Male Wistar rats (270-300 g, 2-3 m) were subjected to 2 h of middle cerebral artery occlusion (MCAo) induced by advancing a surgical nylon filament into the internal carotid artery (ICA) to block the origin of MCA. Briefly, rats were anesthetized with 2% isoflurane in a jar for pre anesthetic, and spontaneously respired with 1.5% isoflurane in 2:1 $N_2O:O_2$ mixture using a facemask connected and regulated with a modified FLUOTEC 3 Vaporizer (Fraser Harlake, Orchard Park, N.Y.). Rectal temperature was maintained at 37° C. throughout the surgical procedure using a feedback regulated water heating system (a recirculating pad and K module and monitored via an intrarectal type T thermocouple). A 1 cm incision was made at the center of the neck, and the right common carotid artery (CCA), external carotid artery (ECA), and internal carotid artery (ICA) were exposed under an operating microscope (Carl Zeiss, Inc., Thormwood, N.Y.). The CCA and ICA were temporarily clamped using microsurgical clips (Codman & Shurtleff, Inc., Randolf, Mass.). A 4-0 nylon suture with its tip rounded by heating near a flame was inserted into the ECA through a small puncture. The microsurgical clips were removed. The length of nylon suture, determined according to the animal's weight, was gently advanced from the ECA into the lumen of the ICA until the suture blocked the origin of the MCA. The nylon filament was retained inside the ICA for 2 hours (h) and the neck incision was closed. The animals were moved to their cage to awake. After 2 h of MCAo, animals were reanesthetized with isoflurane, and restoration of blood flow was performed by withdrawal of the filament until the tip cleared the lumen of the ECA. The incision was then closed.

Adherent $CD10^+$, $CD34^-$, $CD105^+$, $CD200^+$ tissue culture plastic-adherent placental cells were administered by intravenous route (tail vein injection). Animals subjected to MCAo were randomized into one of five groups: (1) human dermal fibroblast as cell control, (2) dextran control, placental cell dose of (3) $1\times10^6$, (4) $4\times10^6$ and (5) $8\times10^6$ cells, administered at day 1 after MCAo. Behavior tests (adhesive test, foot-fault test and mNSS) were performed at day 1 after MCAo before the study treatment (baseline), and at days 7, 14, 21, 28, 42, and 56 after MCAo. The dose-response effects of placental cells on the functional recovery were measured from the three behavior tests described below.

Modified neurological severity score (mNSS Table 1): is graded on a scale of 0 to 18 (normal score 0; maximal deficit score 18, Table 1). One score point is awarded for the inability to perform the test or for the lack of a tested reflex; thus, the higher score, the more severe is the injury.

TABLE 1

Modified neurological severity score scoring criteria.

| Motor Test | Maximum Points |
|---|---|
| Raising the rat by the tail: | 3 |
| 1   Flexion of forelimb | |
| 1   Flexion of hindlimb | |
| 1   Head moved more than 10° to the vertical axis within 30 seconds | |
| Walking on the floor: | 3 |
| 0   Normal walk | |
| 1   Inability to walk straight | |
| 2   Circling toward the paretic side | |
| 3   Fall down to the paretic side | |
| Sensory tests: | 2 |
| 1   Placing test (visual and tactile test) | |
| 1   Proprioceptive test (deep sensation, pushing the paw against the table edge to stimulate limb muscles) | |
| Beam balance tests: | 6 |
| 0   Balances with steady posture | |
| 1   Grasps side of beam | |
| 2   Hugs the beam and one limb falls down from the beam | |
| 3   Hugs the beam and two limbs fall down from the beam, or spins on beam (>60 sec) | |
| 4   Attempts to balance on the beam but fall off (>40 sec) | |
| 5   Attempts to balance on the beam but fall off (>20 sec) | |

TABLE 1-continued

Modified neurological severity score scoring criteria.

| Motor Test | Maximum Points |
|---|---|
| 6  Fall off: No attempt to balance or hang on to the beam (<20 sec) | |
| Reflexes and abnormal movements: | 4 |
| 1  Pinna reflex (a head shake when touching the auditory meatus) | |
| 1  Corneal reflex (an eye blink when lightly touching the cornea with cotton) | |
| 1  Startle reflex (a motor response to a brief noise from clapping hands) | |
| 1  Seizures, myoclonus, myodystony | |
| Maximum Points: | 18 |

Adhesive-removal somatosensory test: All rats were familiarized with the testing environment. In an initial test, two small pieces of adhesive-backed paper dots (of equal size, 113.1 mm$^2$ for test within one month; 56.6 mm$^2$ for test after one month) were used as bilateral tactile stimuli occupying the distal-radial region on the wrist of each forelimb. The rats were then returned to their cages. The time to remove each stimulus from forelimbs was recorded for 5 trials per day.

Foot-fault test: Animals were placed on an elevated grid floor (45 cm by 30 cm), 2.5 cm higher than a solid base floor, with 2.5 cm×2.5 cm diameter openings. Animals tend to move on the grid with their paws placed on the wire frame. When animals inaccurately place a paw, the front limb falls through one of the openings in the grid. When a paw fell or slipped between wires, this was recorded as a foot fault. Total 100 of steps (movement of each forelimb) were counted, and the total number of foot faults for left forelimb was recorded, and the percentage of foot fault of left paw to total steps was determined.

Results:

Modified neurological severity score (mNSS): Animals group treated with 4.0×10$^6$ cells demonstrated improvement in mNSS score compared to vehicle control on days 7-56 ($p<0.05$) (FIG. 5).

Adhesive-removal somatosensory test: Animal group treated with 4.0×10$^6$ cells showed improvement ($p<0.05$) in adhesive-removal somatosensory test compared to vehicle control or cellular control on day 14 post treatment and improvement was sustained throughout the study period (FIG. 6). Additionally, animals treated with 8.0×10$^6$ cells showed improvement ($p<0.05$) at days 42 and 56 post-treatment.

Foot-fault test: Animals group treated with 4.0×10$^6$ cells demonstrated improvement compared to vehicle control or cellular control on day 7 post-treatment and improvement was persistent throughout the study period (FIG. 7).

Based on the above studies, it was determined that treatment of stroke dose-dependently improves functional outcome after stroke in rats compared to fibroblast-control and dextran control. The optimal dose of placental stem cell treatment in the rats used in this study was determined to be 4×10$^6$.

6.3.2 Proliferation and Synaptic Plasticity Studies

To assess whether administration of placental stem cells facilitated neovascularization, 5-bromo-2-deoxyuridine (BrdU; 50 mg/kg in 0.007 N NaOH physiological saline, Sigma, St, Louis Mo.)) was injected into experimental animals starting 24 h after MCAo and daily for 14 days. Experimental animals were sacrificed and brain tissue sections of the occluded area were obtained and stained with BrdU. Experimental animals were reanesthetized with ketamine (80 mg/kg) and xylazine (13 mg/kg i.p. injection) and the depth of anesthesia was monitored by paw pinch reflex. After anesthesia, 2 mL blood was withdrawn from the heart. The serum was prepared and stored at −20° C. Then the animals were subjected to cardiac puncture with saline (about 200 ml for rats) perfusion and then 4% paraformaldehyde (about 50 ml for rats) perfusion using Simon Varistaltic Pump.

The brain was cut down and fixed in 4% paraformaldehyde for 48 h-72 h, followed by embedding in paraffin for immunostaining. Using a rat brain matrix (Activational Systems Inc., Warren, Mich.), each forebrain was cut into 2 mm thick coronal blocks for a total 7 blocks per animal. Brain sections obtained from the optimal dose (4×10$^6$ cells) of placental stem cell treatment, Dextran MCAo control and FBC control groups were used for immunostaining. A standard paraffin block was obtained from the center of the lesion (bregma −1 mm to +1 mm). A series of 6 μm thick sections were cut from the block. Three coronal brain sections were used for each immunohistochemical staining. Antibody against BrdU, a proliferating cell marker (1:100, Boehringer Mannheim, Indianapolis, Ind.), Von Willebrand Factor (vWF, 1:400; Dako, Carpenteria, Calif.), doublecortin (DCX, a marker of migrating neuroblasts) (C-18, goat polyclonal IgG antibody, 1:200 dilution, Santa Cruz) and synaptophysin (Boehringer Mannheim Biochemica, Monoclonal antibody, clone SY 38, 1:40) immunostaining were performed. BrdU immunostained sections were digitized using a 40× objective (Olympus BX40) via an MCID computer imaging analysis system (Imaging Research, St. Catharines, Canada). BrdU positive cells within a total of 10 enlarged and thin walled vessels located in the boundary area of the ischemic lesion were counted in each section.

For semi-quantification of synaptophysin immunoreactivity, the immunostained coronal section and eight fields of view from the ischemic penumbra (cortex and striatum) in each section were digitized under a 20× objective. The positive area was measured. Data was presented as percentage of positive area.

Results:

Administration of 4×10$^6$ placental stem cells was found to significantly increase angiogenesis as measured by increasing endothelial cell proliferation and vascular density in the ischemic brain compared to FBC-control and Dextran control (FIG. 8). Moreover, administration of 4×10$^6$ placental stem cells significantly increases synaptic plasticity as measured by increased synaptophysin expression in the ischemic brain compared to FBC-control.

6.4 Example 4

Treatment of Stroke Using Multipotent Placental Cells

An individual, 62 years old, presents with hemiplegia on the left side; muscle weakness on the left side of the face; and numbness and reduction in sensation on the left side of the body. The symptoms developed over the course of two hours prior to presentation. A diagnosis of stroke is made. The individual, within one hour of diagnosis, is administered 100-200 milliliters of multipotent, tissue culture plastic-adherent placental cells, at a concentration of about 1×10$^7$ cells per milliliter. The multipotent placental cells administered are assayed to be ≥90% CD34$^-$, CD10$^+$, CD105$^+$ and CD200$^+$. The individual is evaluated at 12 hours, 24 hours, 48 hours, 4 days, and 7 days following administration for discernible improvement in muscle strength or numbness on the left side. A second administration is optionally made.

6.5 Example 5

Placental Cell Formulation for Treatment of Stroke, Hypoxic Injury or Anoxic Injury Multipotent $CD34^-$, $CD10^+$, $CD105^+$ and $CD200^+$ placental cells are filtered to remove clumps, and brought to $10\pm3\times 10^6$ cells per milliliter in a solution comprising 5.5% (w/v) dextran-40, 10% (w/v) human serum albumin, and 5% (v/v) dimethylsulfoxide (DMSO) in water. The total number of cells in the formulation is about $4-7\times10^9$ cells.

The cells so formulated are divided into 20 mL aliquots in 50 mL freezing containers and frozen. The aliquoted cells are diluted for use with 10% dextran-40 in sodium chloride into a 1000 mL infusion bag.

EQUIVALENTS

The compositions and methods disclosed herein are not to be limited in scope by the specific embodiments described herein. Indeed, various modifications of the compositions and methods in addition to those described will become apparent to those skilled in the art from the foregoing description and accompanying figures. Such modifications are intended to fall within the scope of the appended claims.

Various publications, patents and patent applications are cited herein, the disclosures of each of which are incorporated by reference in their entireties.

What is claimed is:

1. A method of treating an individual having a disruption in the flow of blood in or around the brain, comprising administering to said individual an effective amount of an isolated population of cells comprising human adherent placental cells that are $CD10^+$, $CD34^-$, $CD105^+$, and $CD200^+$, wherein at least 70% of said placental cells in said population of cells are non-maternal in origin.

2. The method of claim 1, wherein said therapeutically effective amount is an amount that results in elimination of a detectable improvement in, lessening of the severity of, or slowing of the progression of one or more symptoms of disruption in the flow of blood in or around the brain exhibited by said individual.

3. The method of claim 2, wherein said symptom is hemiplegia or hemiparesis.

4. The method of claim 2, wherein said symptom is muscle weakness of the face; numbness; reduction in sensation; altered smell, taste, hearing, or vision; loss of smell, taste, hearing, or vision; drooping of an eyelid (ptosis); detectable weakness of an ocular muscle; decreased gag reflex; decreased ability to swallow; decreased pupil reactivity to light; decreased sensation of the face; decreased balance; nystagmus; altered breathing rate; altered heart rate; weakness in sternocleidomastoid muscle with decreased ability or inability to turn the head to one side; weakness in the tongue; aphasia (inability to speak or understand language); apraxia (altered voluntary movements); a visual field defect; a memory deficit; hemineglect or hemispatial neglect (deficit in attention to the space on the side of the visual field opposite the lesion); disorganized thinking; confusion; development of hypersexual gestures; anosognosia (persistent denial of the existence of a deficit); difficulty walking; altered movement coordination; vertigo; disequilibrium; loss of consciousness; headache; or vomiting, wherein said symptom is caused by disruption in the flow of blood in or around the brain.

5. The method of claim 1, wherein at least 80% of the cells in said population are said isolated human adherent placental cells.

6. The method of claim 1, wherein at least 90% of the cells in said population are said isolated human adherent placental cells.

7. The method of claim 1, wherein said disruption of the flow of blood is stroke.

8. The method of claim 7, wherein said stroke is ischemic stroke.

9. The method of claim 7, wherein said stroke is hemorrhagic stroke.

10. The method of claim 1, wherein said disruption is a hematoma.

11. The method of claim 10, wherein said hematoma is a dural hematoma, a subdural hematoma, or a subarachnoid hematoma.

12. The method of claim 1, wherein said disruption is vasospasm.

13. The method of claim 1, wherein said population of cells is administered by bolus injection.

14. The method of claim 1, wherein said population of cells is administered by intravenous infusion.

15. The method of claim 1, wherein said population of cells is administered intracranially.

16. The method of claim 15, wherein said population of cells is administered within an area of ischemia.

17. The method of claim 15, wherein said population of cells is administered to an area peripheral to an ischemia.

18. The method of claim 1, wherein said population of cells is administered intraperitoneally, intramuscularly, intradermally or intraocularly.

19. The method of claim 1, wherein said population of cells is administered by surgical implantation of a composition comprising said population of cells.

20. The method of claim 19, wherein said composition is a matrix or scaffold.

21. The method of claim 20, wherein said matrix or scaffold is a hydrogel.

22. The method of claim 20, wherein said matrix or scaffold is a decellularized tissue.

23. The method of claim 20, wherein said matrix or scaffold is a synthetic biodegradable composition.

24. The method of claim 1, wherein said population of cells is administered once to said individual.

25. The method of claim 1, wherein said population of cells is administered to said individual a plurality of times.

26. The method of claim 1, wherein said administering comprises administering a population of cells comprising between about $1\times10^4$ and $1\times10^5$ isolated placental cells per kilogram of said individual.

27. The method of claim 1, wherein said administering comprises administering a population of cells comprising between about $1\times10^5$ and $1\times10^6$ isolated placental cells per kilogram of said individual.

28. The method of claim 1, wherein said administering comprises administering a population of cells comprising between about $1\times10^6$ and $1\times10^7$ isolated placental cells per kilogram of said individual.

29. The method of claim 1, wherein said administering comprises administering a population of cells comprising between about $1\times10^7$ and $1\times10^8$ isolated placental cells per kilogram of said individual.

30. The method of claim 1, wherein said administering comprises administering a population of cells comprising between about $5\times10^7$ and $3\times10^9$ isolated placental cells intravenously.

31. The method of claim 30, wherein said administering comprises administering a population of cells comprising about $9 \times 10^8$ isolated placental cells.

32. The method of claim 30, wherein said administering comprises administering a population of cells comprising about $1.8 \times 10^9$ isolated placental cells.

33. The method of claim 1, wherein said administering comprises administering a population of cells comprising between about $5 \times 10^7$ and $1 \times 10^8$ isolated placental cells intracranially.

34. The method of claim 33, wherein said administering comprises administering a population of cells comprising about $9 \times 10^7$ isolated placental cells.

35. The method of claim 1, comprising administering a second therapeutic agent to said individual.

36. The method of claim 35, wherein said second therapeutic agent is a neuroprotective agent.

37. The method of claim 36, wherein said second therapeutic agent is NXY-059 (disuifonyl derivative of phenylbutylnitrone).

38. The method of claim 35, wherein said second therapeutic agent is a thrombolytic agent.

39. The method of claim 38, wherein said thrombolytic agent is tissue plasminogen activator (tPA).

40. The method of claim 1, wherein said population of cells is administered to said individual within 48 hours of development of one or more symptoms of disruption of blood How in or around the brain in said individual.

41. The method of claim 1, wherein said population of cells is administered to said individual within 24 hours of development of one or more symptoms of disruption of blood flow in or around the brain in said individual.

42. The method of claim 1, wherein said population of cells is administered to said individual within 12 hours of development of one or more symptoms of disruption of blood flow in or around the brain in said individual.

43. The method of claim 1, wherein said population of cells is administered to said individual within 3 hours of development of one or more symptoms of disruption of blood flow in or around the brain in said individual.

44. The method of claim 1, wherein said isolated placental cells in said population were cryopreserved prior to said administering.

45. The method of claim 1, wherein said isolated human adherent placental cells in said population are obtained from a placental stem cell bank.

* * * * *